US008673632B2

(12) United States Patent
Crooke et al.

(10) Patent No.: US 8,673,632 B2
(45) Date of Patent: Mar. 18, 2014

(54) MODULATION OF APOLIPOPROTEIN (A) EXPRESSION

(75) Inventors: Rosanne M. Crooke, Carlsbad, CA (US); Mark J. Graham, San Clemente, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 12/726,286

(22) Filed: Mar. 17, 2010

(65) Prior Publication Data

US 2011/0039910 A1 Feb. 17, 2011

Related U.S. Application Data

(63) Continuation of application No. 10/559,647, filed as application No. PCT/US2004/014540 on Jun. 2, 2004, now Pat. No. 7,723,508, which is a continuation of application No. 10/684,440, filed on Oct. 15, 2003, now Pat. No. 7,259,150.

(60) Provisional application No. 60/475,402, filed on Jun. 2, 2003.

(51) Int. Cl.
*C12N 15/85* (2006.01)
*C07H 21/04* (2006.01)
*C07H 21/02* (2006.01)

(52) U.S. Cl.
USPC ...... 435/325; 536/23.1; 536/24.3; 536/24.31; 536/24.33; 536/24.5

(58) Field of Classification Search
None
See application file for complete search history.

(56) References Cited

U.S. PATENT DOCUMENTS

| | | | |
|---|---|---|---|
| 5,721,138 | A | 2/1998 | Lawn |
| 5,801,154 | A | 9/1998 | Baracchini et al. |
| 5,866,551 | A | 2/1999 | Benoit et al. |
| 6,008,344 | A | 12/1999 | Bennett et al. |
| 6,080,580 | A | 6/2000 | Baker et al. |
| 6,512,161 | B1 | 1/2003 | Rouy et al. |
| 6,515,191 | B2 | 2/2003 | Lal et al. |
| 6,525,191 | B1 | 2/2003 | Ramasamy |
| 6,573,050 | B1 | 6/2003 | Ben-David et al. |
| 6,582,908 | B2 | 6/2003 | Fodor et al. |
| 6,613,567 | B1 | 9/2003 | Bennett et al. |
| 6,809,193 | B2 | 10/2004 | McKay et al. |
| 2001/0053519 | A1 | 12/2001 | Fodor et al. |
| 2003/0104410 | A1 | 6/2003 | Mittman |
| 2003/0119766 | A1 | 6/2003 | Crooke et al. |
| 2003/0228597 | A1 | 12/2003 | Cowsert et al. |
| 2004/0242516 | A1 | 12/2004 | Crooke |
| 2006/0281698 | A1 | 12/2006 | Crooke et al. |

FOREIGN PATENT DOCUMENTS

| | | |
|---|---|---|
| WO | WO 96/09392 | 3/1996 |
| WO | WO 97/17371 | 5/1997 |
| WO | WO 99/34016 | 7/1999 |
| WO | WO 99/35241 | 7/1999 |
| WO | WO 03/014307 | 2/2003 |
| WO | WO 2004/031237 | 4/2004 |
| WO | WO 2004/108916 | 12/2004 |
| WO | WO 2005/000201 | 1/2005 |

OTHER PUBLICATIONS

U.S. Appl. No. 60/475,402, Crooke et al.
Agrawal et al., "Antisense oligonucleotides: towards clinical trials" TIBTECH (1996) 14:376-387.
Anderson et al., "A comparison of selected mRNA and protein abundances in human liver" Electrophoresis (1997) 18:533-537.
Berg et al. "Spontaneous Atherosclerosis in the Proximal Aorta of LPA Transgenic Mice on a Normal Diet," Atherosclerosis (2002) vol. 163:99-104.
Braasch et al., "Novel Antisense and Peptide Nucleic Acid Strategies for Controlling Gene Expression" Biochemistry (2002) 41:4503-4510.
Branch, "A Good Antisense Molecule is Hard to Find" TIBS (1998) 23:45-50.
Callow et al., "Expression of human apolipoprotein B and assembly of lipoprotein (a) in transgenic mice" PNAS (1994) 91:2130-2134.
Chiesa et al., "Reconstitution of Lipoprotein (a) by Infusion of Human Low Density Lipoprotein into Transgenic Mice Expressing Human Apolipoprotein (a)" J. of Biological Chem. (1992) 267:24369-24374.
Chin, "On Preparation and Utilization of Isolated and Purified Oligonucleotides" Katherine R. Everett Law Library of the University of North Carolina, Mar. 14, 2002.
Crooke et al., "Basic Principles of Antisense Therapeutics" Antisense Research and Application (1998) Chapter 1:1-50.
Deverre et al., "A competitive enzyme hybridization assay for plasma determination of phosphodiester and phosphorothioate antisense oligonucleotides" Nucleic Acids Res. (1997) 25:3584-3589.
Dias et al., "Potential roles of antisense oligonucleotides in cancer therapy. The example of bcl-2 antisense oligonucleotides." European J. of Pharmaceutics and Biopharmaceutics (2002) 54:263-269.
Elbashir et al., "Functional anatomy of siRNAs for mediating efficient RNAi in *Drosophila melanogaster* embryo lysate" The EMBO Journal (2001) 20(23):6877-6888.

(Continued)

*Primary Examiner* — Amy Bowman
(74) *Attorney, Agent, or Firm* — Jones Day

(57) ABSTRACT

Compounds, compositions and methods are provided for modulating the expression of apolipoprotein(a). The compositions comprise oligonucleotides, targeted to nucleic acid encoding apolipoprotein(a). Methods of using these compounds for modulation of apolipoprotein(a) expression and for diagnosis and treatment of disease associated with expression of apolipoprotein(a) are provided.

4 Claims, No Drawings

(56) References Cited

OTHER PUBLICATIONS

Frank et al., "The apolipoprotein (a) gene resides on human chromosome 6q26-27, in close proximity to the homologous gene for plasminogen" Hum. Genet. (1988) 79:352-356.
Frank et al., "Adenovirus-mediated apo(a)-antisense-RNA expression efficiently inhibits apo(a) synthesis in vitro and in vivo" Gene Therapy (2001) 8:425-430.
Fritz et al., "Cationic Polystyrene Nonoparticles: Preparation and Characterization of a Model Drug Carrier System for Antisense Oligonucleotides" Journal of Colloid and Interface Science (1997) 195:272-288.
Gewirtz et al., "Facilitating oligonucleotide delivery: Helping antisense deliver on its promise" PNAS (1996) 93:3161-3163.
Grainger et al., "Activation of transforming growth factor-beta is inhibited in transgenic apolipoprotein (a) mice" Nature (1994) 370:460-462.
Green et al., "Antisense Oligonucleotides: An Evolving Technology for the Modulation of Gene Expression in Human Disease" J. Am. Coll. Surg. (2000) 191:93-105.
Hajjar et al., "The role of lipoprotein (a) in atherogenesis and thrombosis" Annu. Rev. Med. (1996) 47:423-442.
Holen et al., "Positional effects of short interfering RNAs targeting the human coagulation trigger Tissue Factor" Nucleic Acids Research (2002) 30(8):1757-1766.
Jen, "Suppression of Gene Expression by Targeted Disruption of Messenger RNA: Available Options and Current Strategies" Stem Cells (2000) 18:307-319.
Katan et al., "Characteristics of human hypo-and hyperresponders to dietary cholesterol" Am. J. Epidemiol. (1987) 125:387-399.
Koschinsky, Marlys L., "Lipoprotein(A): On the Cutting Edge of Occam's Razor, website." 8 pages, Jun. 2004.
Kostner et al., "Lipoprotein (a): Still an Enigma?" Current Opinion in Lipidology (2002) 13:391-396.
Lawn et al., "Atherogenesis in transgenic mice expressing human apolipoprotein (a)" Nature (1992) 360:670-672.
McLean et al., "cDNA sequence of human apolipoprotein (a) is homologous to plasminogen" Nature (1987) 330:132-137.
Milligan et al., "Current Concepts in Antisense Drug Design" J. Medicinal Chemistry (1993) 36: 1923-1927.
Morishita et al., "Novel therapeutic strategy for atherosclerosis: ribozyme oligonucleotides against apolipoprotein (a) selectively inhibit apolipoprotein (a) but not plasminogen gene expression" Circulation (1998) 98:1898-1904.
New England Biolabs 1998/99 Catalog (cover page and pp. 121 and 284).
Nowak-Gottl et al., "Lipoprotein (a): its role in childhood thromboembolism" Pediatrics (1997) 99:E11.
Ohmichi et al., "The virtues of self-binding: high sequence specificity for RNA cleavage by self-processed hammerhead ribozymes" Nucleic Acids Res. (2000) 28:776-783.
Olie et al., "Analysis of ribosyl-modified, mixed backbone analogs of a bcl-2/bcl-xL antisense oligonucleotide" Biochimica et Biophysica Acta (2002) 1576:101-109.
Opalinski et al., "Nucleic-Acid Therapeutics: Basic Principles and Recent Applications" Nature Reviews (2002) 1:503-514.
Prosnyak et al., "Substitution of 2-aminoadenine and 5-methylcytosine for adenine and cytosine in hybridization probes increases the sensitivity of DNA fingerprinting" Genomics (1994) 21:490-494.
Rainwater et al., "Lipoprotein Lp (a): effects of allelic variation at the LPA locus" J. Exp. Zool. (1998) 282:54-61.
Reynolds et al., "Rational siRNA design for RNA interference" Nature Biotechnology (2004) 22(3):326-330.
Sandicamp et al., "Lipoprotein (a) is an independent risk factor for myocardial infarction at a young age" Clin. Chem. (1990) 36:20-23.
Sanghvi et al., "Heterocyclic Base Modifications in Nucleic Acids and Their Applications in Antisense Oligonucleotides" Antisense Research and Applications (1993) pp. 273-288.
Seed et al., "Relation of serum lipoprotein (a) concentration and apolipoprotein (a) phenotype to coronary heart disease in patients with familial hypercholesterolemia" N. Engl. J. Med. (1990) 322:1494-1499.
Skerra, "Phosphorothioate primers improve the amplification of DNA sequences by DNA polymerase with proofreading activity" Nucleic Acids Res. (1992) 20:3551-3554.
Tamm et al., "Antisense therapy in oncology: new hope for an old idea?" The Lancet (2001) 358:489-497.
Tuschl et al, 2004, "Selection of siRNA Duplexes from the Target mRNA Sequence," The siRNA user guide, (Rev. 5/04), retrieved Apr. 7, 2009, Max Planck Institute for Biophysical Chemistry, (available at) http://www.rockefeller.edu/labheads/tuschl/sima.html.
Vessby et al., "Diverging Effects of Cholestyramine on Apolipoprotein B and Lipoprotein Lp (a)" Atherosclerosis (1982) 44:61-71.
Weintraub et al., "Antisense RNA and DNA" Scientific American (1990) 40-46.
Yang et al, "Transforming Growth Factor-Bl Inhibits Human Keratinocyte Proliferation by Upregulation of a Receptor-Type Tyrosine Phosphatase R-PTP-K Gene Expression" Biochem. Biophys. Res. Commun. (1996) 228:807-812.
U.S.P.T.O. Office Action from U.S. Appl. No. 09/923,515 dated Aug. 7, 2001.
U.S.P.T.O. Office Action from U.S. Appl. No. 09/923,515 dated Mar. 19, 2003.
U.S.P.T.O. Office Action from U.S. Appl. No. 09/923,515 dated Mar. 9, 2004.
U.S.P.T.O. Office Action from U.S. Appl. No. 09/923,515 dated Nov. 3, 2004.
U.S.P.T.O. Office Action from U.S. Appl. No. 09/923,515 dated Apr. 6, 2005.
U.S.P.T.O. Office Action from U.S. Appl. No. 09/923,515 dated Sep. 22, 2005.
U.S.P.T.O. Final Rejection from U.S. Appl. No. 09/923,515 dated Sep. 18, 2006.
U.S.P.T.O. Office Action from U.S. Appl. No. 10/684,440 dated Oct. 15, 2003.
U.S.P.T.O. Office Action from U.S. Appl. No. 10/684,440 dated Jan. 26, 2005.
U.S.P.T.O. Final Rejection from U.S. Appl. No. 10/684,440 dated Aug. 26, 2005.
U.S.P.T.O. Office Action from U.S. Appl. No. 10/684,440 dated May 30, 2006.
U.S.P.T.O. Office Action from U.S. Appl. No. 10/559,647 dated May 14, 2007.
U.S.P.T.O. Final Rejection from U.S. Appl. No. 10/559,647 dated Nov. 15, 2007.
U.S.P.T.O. Office Action from U.S. Appl. No. 10/559,647 dated Jul. 31, 2008.
U.S.P.T.O. Final Rejection from U.S. Appl. No. 10/559,647 dated Feb. 24, 2009.
EP Search Report from EP 04751768.5 dated Nov. 3, 2006.
EP Search Report from EP 02794670.6 dated Jan. 24, 2005.
International Search Report from PCT/US2002/024920 dated Jul. 16, 2003.
International Search Report from PCT/US2004/014540 dated Jan. 25, 2006.

SEQUENCE LISTING

```
<160> NUMBER OF SEQ ID NOS: 100

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
gtgcgcgcga gcccgaaatc                                              20
```

```
<210> SEQ ID NO 3
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 3
atgcattctg cccccaagga                                                 20

<210> SEQ ID NO 4
<211> LENGTH: 13938
<212> TYPE: DNA
<213> ORGANISM: H. sapiens
<220> FEATURE:
<221> NAME/KEY: CDS
<222> LOCATION: (46)...(13692)

<400> SEQUENCE: 4
```

| | | | | | | |
|---|---|---|---|---|---|---|
| ctgggattgg gacacactt ctggacactg ctggccagtc ccaaa atg gaa cat aag | | | | | | 57 |
| | | | | Met Glu His Lys | | |
| | | | | 1 | | |

| gaa gtg gtt ctt cta ctt ctt tta ttt ctg aaa tca gca gca cct gag | 105 |
|---|---|
| Glu Val Val Leu Leu Leu Leu Leu Phe Leu Lys Ser Ala Ala Pro Glu | |
| 5           10          15          20 | |

| caa agc cat gtg gtc cag gat tgc tac cat ggt gat gga cag agt tat | 153 |
|---|---|
| Gln Ser His Val Val Gln Asp Cys Tyr His Gly Asp Gly Gln Ser Tyr | |
| 25          30          35 | |

| cga ggc acg tac tcc acc act gtc aca gga agg acc tgc caa gct tgg | 201 |
|---|---|
| Arg Gly Thr Tyr Ser Thr Thr Val Thr Gly Arg Thr Cys Gln Ala Trp | |
| 40          45          50 | |

| tca tct atg aca cca cat caa cat aat agg acc aca gaa aac tac cca | 249 |
|---|---|
| Ser Ser Met Thr Pro His Gln His Asn Arg Thr Thr Glu Asn Tyr Pro | |
| 55          60          65 | |

| aat gct ggc ttg atc atg aac tac tgc agg aat cca gat gct gtg gca | 297 |
|---|---|
| Asn Ala Gly Leu Ile Met Asn Tyr Cys Arg Asn Pro Asp Ala Val Ala | |
| 70          75          80 | |

| gct cct tat tgt tat acg agg gat ccc ggt gtc agg tgg gag tac tgc | 345 |
|---|---|
| Ala Pro Tyr Cys Tyr Thr Arg Asp Pro Gly Val Arg Trp Glu Tyr Cys | |
| 85          90          95          100 | |

| aac ctg acg caa tgc tca gac gca gaa ggg act gcc gtc gcg cct ccg | 393 |
|---|---|
| Asn Leu Thr Gln Cys Ser Asp Ala Glu Gly Thr Ala Val Ala Pro Pro | |
| 105         110         115 | |

| act gtt acc ccg gtt cca agc cta gag gct cct tcc gaa caa gca ccg | 441 |
|---|---|
| Thr Val Thr Pro Val Pro Ser Leu Glu Ala Pro Ser Glu Gln Ala Pro | |
| 120         125         130 | |

| act gag caa agg cct ggg gtg cag gag tgc tac cat ggt aat gga cag | 489 |
|---|---|
| Thr Glu Gln Arg Pro Gly Val Gln Glu Cys Tyr His Gly Asn Gly Gln | |
| 135         140         145 | |

| agt tat cga ggc aca tac tcc acc act gtc aca gga aga acc tgc caa | 537 |
|---|---|
| Ser Tyr Arg Gly Thr Tyr Ser Thr Thr Val Thr Gly Arg Thr Cys Gln | |
| 150         155         160 | |

| gct tgg tca tct atg aca cca cac tcg cat agt cgg acc cca gaa tac | 585 |
|---|---|
| Ala Trp Ser Ser Met Thr Pro His Ser His Ser Arg Thr Pro Glu Tyr | |
| 165         170         175         180 | |

| tac cca aat gct ggc ttg atc atg aac tac tgc agg aat cca gat gct | 633 |
|---|---|
| Tyr Pro Asn Ala Gly Leu Ile Met Asn Tyr Cys Arg Asn Pro Asp Ala | |
| 185         190         195 | |

| gtg gca gct cct tat tgt tat acg agg gat ccc ggt gtc agg tgg gag | 681 |
|---|---|
| Val Ala Ala Pro Tyr Cys Tyr Thr Arg Asp Pro Gly Val Arg Trp Glu | |
| 200         205         210 | |

| tac tgc aac ctg acg caa tgc tca gac gca gaa ggg act gcc gtc gcg | 729 |
|---|---|

```
Tyr Cys Asn Leu Thr Gln Cys Ser Asp Ala Glu Gly Thr Ala Val Ala
            215                 220                 225 cct ccg act gtt acc ccg gtt cca agc cta gag gct cct tcc gaa caa       777
Pro Pro Thr Val Thr Pro Val Pro Ser Leu Glu Ala Pro Ser Glu Gln
230                 235                 240 gca ccg act gag caa agg cct ggg gtg cag gag tgc tac cat ggt aat       825
Ala Pro Thr Glu Gln Arg Pro Gly Val Gln Glu Cys Tyr His Gly Asn
245                 250                 255                 260 gga cag agt tat cga ggc aca tac tcc acc act gtc aca gga aga acc       873
Gly Gln Ser Tyr Arg Gly Thr Tyr Ser Thr Thr Val Thr Gly Arg Thr
                265                 270                 275 tgc caa gct tgg tca tct atg aca cca cac tcg cat agt cgg acc cca       921
Cys Gln Ala Trp Ser Ser Met Thr Pro His Ser His Ser Arg Thr Pro
            280                 285                 290 gaa tac tac cca aat gct ggc ttg atc atg aac tac tgc agg aat cca       969
Glu Tyr Tyr Pro Asn Ala Gly Leu Ile Met Asn Tyr Cys Arg Asn Pro
                295                 300                 305 gat gct gtg gca gct cct tat tgt tat acg agg gat ccc ggt gtc agg      1017
Asp Ala Val Ala Ala Pro Tyr Cys Tyr Thr Arg Asp Pro Gly Val Arg
310                 315                 320 tgg gag tac tgc aac ctg acg caa tgc tca gac gca gaa ggg act gcc      1065
Trp Glu Tyr Cys Asn Leu Thr Gln Cys Ser Asp Ala Glu Gly Thr Ala
325                 330                 335                 340 gtc gcg cct ccg act gtt acc ccg gtt cca agc cta gag gct cct tcc      1113
Val Ala Pro Pro Thr Val Thr Pro Val Pro Ser Leu Glu Ala Pro Ser
                345                 350                 355 gaa caa gca ccg act gag caa agg cct ggg gtg cag gag tgc tac cat      1161
Glu Gln Ala Pro Thr Glu Gln Arg Pro Gly Val Gln Glu Cys Tyr His
            360                 365                 370 ggt aat gga cag agt tat cga ggc aca tac tcc acc act gtc aca gga      1209
Gly Asn Gly Gln Ser Tyr Arg Gly Thr Tyr Ser Thr Thr Val Thr Gly
                375                 380                 385 aga acc tgc caa gct tgg tca tct atg aca cca cac tcg cat agt cgg      1257
Arg Thr Cys Gln Ala Trp Ser Ser Met Thr Pro His Ser His Ser Arg
390                 395                 400 acc cca gaa tac tac cca aat gct ggc ttg atc atg aac tac tgc agg      1305
Thr Pro Glu Tyr Tyr Pro Asn Ala Gly Leu Ile Met Asn Tyr Cys Arg
405                 410                 415                 420 aat cca gat gct gtg gca gct cct tat tgt tat acg agg gat ccc ggt      1353
Asn Pro Asp Ala Val Ala Ala Pro Tyr Cys Tyr Thr Arg Asp Pro Gly
                425                 430                 435 gtc agg tgg gag tac tgc aac ctg acg caa tgc tca gac gca gaa ggg      1401
Val Arg Trp Glu Tyr Cys Asn Leu Thr Gln Cys Ser Asp Ala Glu Gly
            440                 445                 450 act gcc gtc gcg cct ccg act gtt acc ccg gtt cca agc cta gag gct      1449
Thr Ala Val Ala Pro Pro Thr Val Thr Pro Val Pro Ser Leu Glu Ala
                455                 460                 465 cct tcc gaa caa gca ccg act gag caa agg cct ggg gtg cag gag tgc      1497
Pro Ser Glu Gln Ala Pro Thr Glu Gln Arg Pro Gly Val Gln Glu Cys
470                 475                 480 tac cat ggt aat gga cag agt tat cga ggc aca tac tcc acc act gtc      1545
Tyr His Gly Asn Gly Gln Ser Tyr Arg Gly Thr Tyr Ser Thr Thr Val
485                 490                 495                 500 aca gga aga acc tgc caa gct tgg tca tct atg aca cca cac tcg cat      1593
Thr Gly Arg Thr Cys Gln Ala Trp Ser Ser Met Thr Pro His Ser His
                505                 510                 515 agt cgg acc cca gaa tac tac cca aat gct ggc ttg atc atg aac tac      1641
Ser Arg Thr Pro Glu Tyr Tyr Pro Asn Ala Gly Leu Ile Met Asn Tyr
            520                 525                 530 tgc agg aat cca gat gct gtg gca gct cct tat tgt tat acg agg gat      1689
```

-continued

| | | | | | | | | | | | | |
|---|---|---|---|---|---|---|---|---|---|---|---|---|
| Cys | Arg | Asn | Pro | Asp | Ala | Val | Ala | Ala | Pro | Tyr | Cys | Tyr | Thr | Arg | Asp |
| | | 535 | | | | 540 | | | | 545 | | |

```
ccc ggt gtc agg tgg gag tac tgc aac ctg acg caa tgc tca gac gca      1737
Pro Gly Val Arg Trp Glu Tyr Cys Asn Leu Thr Gln Cys Ser Asp Ala
    550             555                 560 gaa ggg act gcc gtc gcg cct ccg act gtt acc ccg gtt cca agc cta      1785
Glu Gly Thr Ala Val Ala Pro Pro Thr Val Thr Pro Val Pro Ser Leu
565             570                 575                 580 gag gct cct tcc gaa caa gca ccg act gag caa agg cct ggg gtg cag      1833
Glu Ala Pro Ser Glu Gln Ala Pro Thr Glu Gln Arg Pro Gly Val Gln
            585                 590                 595 gag tgc tac cat ggt aat gga cag agt tat cga ggc aca tac tcc acc      1881
Glu Cys Tyr His Gly Asn Gly Gln Ser Tyr Arg Gly Thr Tyr Ser Thr
                600                 605                 610 act gtc aca gga aga acc tgc caa gct tgg tca tct atg aca cca cac      1929
Thr Val Thr Gly Arg Thr Cys Gln Ala Trp Ser Ser Met Thr Pro His
            615                 620                 625 tcg cat agt cgg acc cca gaa tac tac cca aat gct ggc ttg atc atg      1977
Ser His Ser Arg Thr Pro Glu Tyr Tyr Pro Asn Ala Gly Leu Ile Met
    630                 635                 640 aac tac tgc agg aat cca gat gct gtg gca gct cct tat tgt tat acg      2025
Asn Tyr Cys Arg Asn Pro Asp Ala Val Ala Ala Pro Tyr Cys Tyr Thr
645                 650                 655                 660 agg gat ccc ggt gtc agg tgg gag tac tgc aac ctg acg caa tgc tca      2073
Arg Asp Pro Gly Val Arg Trp Glu Tyr Cys Asn Leu Thr Gln Cys Ser
            665                 670                 675 gac gca gaa ggg act gcc gtc gcg cct ccg act gtt acc ccg gtt cca      2121
Asp Ala Glu Gly Thr Ala Val Ala Pro Pro Thr Val Thr Pro Val Pro
                680                 685                 690 agc cta gag gct cct tcc gaa caa gca ccg act gag caa agg cct ggg      2169
Ser Leu Glu Ala Pro Ser Glu Gln Ala Pro Thr Glu Gln Arg Pro Gly
            695                 700                 705 gtg cag gag tgc tac cat ggt aat gga cag agt tat cga ggc aca tac      2217
Val Gln Glu Cys Tyr His Gly Asn Gly Gln Ser Tyr Arg Gly Thr Tyr
710                 715                 720 tcc acc act gtc aca gga aga acc tgc caa gct tgg tca tct atg aca      2265
Ser Thr Thr Val Thr Gly Arg Thr Cys Gln Ala Trp Ser Ser Met Thr
725                 730                 735                 740 cca cac tcg cat agt cgg acc cca gaa tac tac cca aat gct ggc ttg      2313
Pro His Ser His Ser Arg Thr Pro Glu Tyr Tyr Pro Asn Ala Gly Leu
                745                 750                 755 atc atg aac tac tgc agg aat cca gat gct gtg gca gct cct tat tgt      2361
Ile Met Asn Tyr Cys Arg Asn Pro Asp Ala Val Ala Ala Pro Tyr Cys
            760                 765                 770 tat acg agg gat ccc ggt gtc agg tgg gag tac tgc aac ctg acg caa      2409
Tyr Thr Arg Asp Pro Gly Val Arg Trp Glu Tyr Cys Asn Leu Thr Gln
    775                 780                 785 tgc tca gac gca gaa ggg act gcc gtc gcg cct ccg act gtt acc ccg      2457
Cys Ser Asp Ala Glu Gly Thr Ala Val Ala Pro Pro Thr Val Thr Pro
790                 795                 800 gtt cca agc cta gag gct cct tcc gaa caa gca ccg act gag caa agg      2505
Val Pro Ser Leu Glu Ala Pro Ser Glu Gln Ala Pro Thr Glu Gln Arg
805                 810                 815                 820 cct ggg gtg cag gag tgc tac cat ggt aat gga cag agt tat cga ggc      2553
Pro Gly Val Gln Glu Cys Tyr His Gly Asn Gly Gln Ser Tyr Arg Gly
                825                 830                 835 aca tac tcc acc act gtc aca gga aga acc tgc caa gct tgg tca tct      2601
Thr Tyr Ser Thr Thr Val Thr Gly Arg Thr Cys Gln Ala Trp Ser Ser
            840                 845                 850 atg aca cca cac tcg cat agt cgg acc cca gaa tac tac cca aat gct      2649
```

```
                 Met Thr Pro His Ser His Ser Arg Thr Pro Glu Tyr Tyr Pro Asn Ala
                     855                 860                 865 ggc ttg atc atg aac tac tgc agg aat cca gat gct gtg gca gct cct            2697
Gly Leu Ile Met Asn Tyr Cys Arg Asn Pro Asp Ala Val Ala Ala Pro
        870                 875                 880 tat tgt tat acg agg gat ccc ggt gtc agg tgg gag tac tgc aac ctg            2745
Tyr Cys Tyr Thr Arg Asp Pro Gly Val Arg Trp Glu Tyr Cys Asn Leu
885                 890                 895                 900 acg caa tgc tca gac gca gaa ggg act gcc gtc gcg cct ccg act gtt            2793
Thr Gln Cys Ser Asp Ala Glu Gly Thr Ala Val Ala Pro Pro Thr Val
                905                 910                 915 acc ccg gtt cca agc cta gag gct cct tcc gaa caa gca ccg act gag            2841
Thr Pro Val Pro Ser Leu Glu Ala Pro Ser Glu Gln Ala Pro Thr Glu
        920                 925                 930 caa agg cct ggg gtg cag gag tgc tac cat ggt aat gga cag agt tat            2889
Gln Arg Pro Gly Val Gln Glu Cys Tyr His Gly Asn Gly Gln Ser Tyr
            935                 940                 945 cga ggc aca tac tcc acc act gtc aca gga aga acc tgc caa gct tgg            2937
Arg Gly Thr Tyr Ser Thr Thr Val Thr Gly Arg Thr Cys Gln Ala Trp
950                 955                 960 tca tct atg aca cca cac tcg cat agt cgg acc cca gaa tac tac cca            2985
Ser Ser Met Thr Pro His Ser His Ser Arg Thr Pro Glu Tyr Tyr Pro
965                 970                 975                 980 aat gct ggc ttg atc atg aac tac tgc agg aat cca gat gct gtg gca            3033
Asn Ala Gly Leu Ile Met Asn Tyr Cys Arg Asn Pro Asp Ala Val Ala
                985                 990                 995 gct cct tat tgt tat acg agg gat ccc ggt gtc agg tgg gag tac tgc            3081
Ala Pro Tyr Cys Tyr Thr Arg Asp Pro Gly Val Arg Trp Glu Tyr Cys
        1000                1005                1010 aac ctg acg caa tgc tca gac gca gaa ggg act gcc gtc gcg cct ccg            3129
Asn Leu Thr Gln Cys Ser Asp Ala Glu Gly Thr Ala Val Ala Pro Pro
            1015                1020                1025 act gtt acc ccg gtt cca agc cta gag gct cct tcc gaa caa gca ccg            3177
Thr Val Thr Pro Val Pro Ser Leu Glu Ala Pro Ser Glu Gln Ala Pro
        1030                1035                1040 act gag caa agg cct ggg gtg cag gag tgc tac cat ggt aat gga cag            3225
Thr Glu Gln Arg Pro Gly Val Gln Glu Cys Tyr His Gly Asn Gly Gln
1045                1050                1055                1060 agt tat cga ggc aca tac tcc acc act gtc aca gga aga acc tgc caa            3273
Ser Tyr Arg Gly Thr Tyr Ser Thr Thr Val Thr Gly Arg Thr Cys Gln
                1065                1070                1075 gct tgg tca tct atg aca cca cac tcg cat agt cgg acc cca gaa tac            3321
Ala Trp Ser Ser Met Thr Pro His Ser His Ser Arg Thr Pro Glu Tyr
        1080                1085                1090 tac cca aat gct ggc ttg atc atg aac tac tgc agg aat cca gat gct            3369
Tyr Pro Asn Ala Gly Leu Ile Met Asn Tyr Cys Arg Asn Pro Asp Ala
            1095                1100                1105 gtg gca gct cct tat tgt tat acg agg gat ccc ggt gtc agg tgg gag            3417
Val Ala Ala Pro Tyr Cys Tyr Thr Arg Asp Pro Gly Val Arg Trp Glu
        1110                1115                1120 tac tgc aac ctg acg caa tgc tca gac gca gaa ggg act gcc gtc gcg            3465
Tyr Cys Asn Leu Thr Gln Cys Ser Asp Ala Glu Gly Thr Ala Val Ala
1125                1130                1135                1140 cct ccg act gtt acc ccg gtt cca agc cta gag gct cct tcc gaa caa            3513
Pro Pro Thr Val Thr Pro Val Pro Ser Leu Glu Ala Pro Ser Glu Gln
                1145                1150                1155 gca ccg act gag caa agg cct ggg gtg cag gag tgc tac cat ggt aat            3561
Ala Pro Thr Glu Gln Arg Pro Gly Val Gln Glu Cys Tyr His Gly Asn
        1160                1165                1170 gga cag agt tat cga ggc aca tac tcc acc act gtc aca gga aga acc            3609
```

-continued

| | | | | | | | | | | | | |
|---|---|---|---|---|---|---|---|---|---|---|---|---|
| Gly | Gln | Ser | Tyr | Arg | Gly | Thr | Tyr | Ser | Thr | Thr | Val | Thr | Gly | Arg | Thr |
| | | | 1175 | | | | 1180 | | | | 1185 | | | | |

```
tgc caa gct tgg tca tct atg aca cca cac tcg cat agt cgg acc cca    3657
Cys Gln Ala Trp Ser Ser Met Thr Pro His Ser His Ser Arg Thr Pro
        1190                1195                1200 gaa tac tac cca aat gct ggc ttg atc atg aac tac tgc agg aat cca    3705
Glu Tyr Tyr Pro Asn Ala Gly Leu Ile Met Asn Tyr Cys Arg Asn Pro
1205                1210                1215                1220 gat gct gtg gca gct cct tat tgt tat acg agg gat ccc ggt gtc agg    3753
Asp Ala Val Ala Ala Pro Tyr Cys Tyr Thr Arg Asp Pro Gly Val Arg
                1225                1230                1235 tgg gag tac tgc aac ctg acg caa tgc tca gac gca gaa ggg act gcc    3801
Trp Glu Tyr Cys Asn Leu Thr Gln Cys Ser Asp Ala Glu Gly Thr Ala
        1240                1245                1250 gtc gcg cct ccg act gtt acc ccg gtt cca agc cta gag gct cct tcc    3849
Val Ala Pro Pro Thr Val Thr Pro Val Pro Ser Leu Glu Ala Pro Ser
1255                1260                1265 gaa caa gca ccg act gag caa agg cct ggg gtg cag gag tgc tac cat    3897
Glu Gln Ala Pro Thr Glu Gln Arg Pro Gly Val Gln Glu Cys Tyr His
        1270                1275                1280 ggt aat gga cag agt tat cga ggc aca tac tcc acc act gtc aca gga    3945
Gly Asn Gly Gln Ser Tyr Arg Gly Thr Tyr Ser Thr Thr Val Thr Gly
1285                1290                1295                1300 aga acc tgc caa gct tgg tca tct atg aca cca cac tcg cat agt cgg    3993
Arg Thr Cys Gln Ala Trp Ser Ser Met Thr Pro His Ser His Ser Arg
                1305                1310                1315 acc cca gaa tac tac cca aat gct ggc ttg atc atg aac tac tgc agg    4041
Thr Pro Glu Tyr Tyr Pro Asn Ala Gly Leu Ile Met Asn Tyr Cys Arg
        1320                1325                1330 aat cca gat gct gtg gca gct cct tat tgt tat acg agg gat ccc ggt    4089
Asn Pro Asp Ala Val Ala Ala Pro Tyr Cys Tyr Thr Arg Asp Pro Gly
1335                1340                1345 gtc agg tgg gag tac tgc aac ctg acg caa tgc tca gac gca gaa ggg    4137
Val Arg Trp Glu Tyr Cys Asn Leu Thr Gln Cys Ser Asp Ala Glu Gly
        1350                1355                1360 act gcc gtc gcg cct ccg act gtt acc ccg gtt cca agc cta gag gct    4185
Thr Ala Val Ala Pro Pro Thr Val Thr Pro Val Pro Ser Leu Glu Ala
1365                1370                1375                1380 cct tcc gaa caa gca ccg act gag caa agg cct ggg gtg cag gag tgc    4233
Pro Ser Glu Gln Ala Pro Thr Glu Gln Arg Pro Gly Val Gln Glu Cys
                1385                1390                1395 tac cat ggt aat gga cag agt tat cga ggc aca tac tcc acc act gtc    4281
Tyr His Gly Asn Gly Gln Ser Tyr Arg Gly Thr Tyr Ser Thr Thr Val
        1400                1405                1410 aca gga aga acc tgc caa gct tgg tca tct atg aca cca cac tcg cat    4329
Thr Gly Arg Thr Cys Gln Ala Trp Ser Ser Met Thr Pro His Ser His
1415                1420                1425 agt cgg acc cca gaa tac tac cca aat gct ggc ttg atc atg aac tac    4377
Ser Arg Thr Pro Glu Tyr Tyr Pro Asn Ala Gly Leu Ile Met Asn Tyr
        1430                1435                1440 tgc agg aat cca gat gct gtg gca gct cct tat tgt tat acg agg gat    4425
Cys Arg Asn Pro Asp Ala Val Ala Ala Pro Tyr Cys Tyr Thr Arg Asp
1445                1450                1455                1460 ccc ggt gtc agg tgg gag tac tgc aac ctg acg caa tgc tca gac gca    4473
Pro Gly Val Arg Trp Glu Tyr Cys Asn Leu Thr Gln Cys Ser Asp Ala
        1465                1470                1475 gaa ggg act gcc gtc gcg cct ccg act gtt acc ccg gtt cca agc cta    4521
Glu Gly Thr Ala Val Ala Pro Pro Thr Val Thr Pro Val Pro Ser Leu
1480                1485                1490 gag gct cct tcc gaa caa gca ccg act gag caa agg cct ggg gtg cag    4569
```

```
Glu Ala Pro Ser Glu Gln Ala Pro Thr Glu Gln Arg Pro Gly Val Gln
        1495                1500                1505 gag tgc tac cat ggt aat gga cag agt tat cga ggc aca tac tcc acc    4617
Glu Cys Tyr His Gly Asn Gly Gln Ser Tyr Arg Gly Thr Tyr Ser Thr
1510                1515                1520 act gtc aca gga aga acc tgc caa gct tgg tca tct atg aca cca cac    4665
Thr Val Thr Gly Arg Thr Cys Gln Ala Trp Ser Ser Met Thr Pro His
1525                1530                1535                1540 tcg cat agt cgg acc cca gaa tac tac cca aat gct ggc ttg atc atg    4713
Ser His Ser Arg Thr Pro Glu Tyr Tyr Pro Asn Ala Gly Leu Ile Met
                1545                1550                1555 aac tac tgc agg aat cca gat gct gtg gca gct cct tat tgt tat acg    4761
Asn Tyr Cys Arg Asn Pro Asp Ala Val Ala Ala Pro Tyr Cys Tyr Thr
            1560                1565                1570 agg gat ccc ggt gtc agg tgg gag tac tgc aac ctg acg caa tgc tca    4809
Arg Asp Pro Gly Val Arg Trp Glu Tyr Cys Asn Leu Thr Gln Cys Ser
        1575                1580                1585 gac gca gaa ggg act gcc gtc gcg cct ccg act gtt acc ccg gtt cca    4857
Asp Ala Glu Gly Thr Ala Val Ala Pro Pro Thr Val Thr Pro Val Pro
1590                1595                1600 agc cta gag gct cct tcc gaa caa gca ccg act gag caa agg cct ggg    4905
Ser Leu Glu Ala Pro Ser Glu Gln Ala Pro Thr Glu Gln Arg Pro Gly
1605                1610                1615                1620 gtg cag gag tgc tac cat ggt aat gga cag agt tat cga ggc aca tac    4953
Val Gln Glu Cys Tyr His Gly Asn Gly Gln Ser Tyr Arg Gly Thr Tyr
                1625                1630                1635 tcc acc act gtc aca gga aga acc tgc caa gct tgg tca tct atg aca    5001
Ser Thr Thr Val Thr Gly Arg Thr Cys Gln Ala Trp Ser Ser Met Thr
            1640                1645                1650 cca cac tcg cat agt cgg acc cca gaa tac tac cca aat gct ggc ttg    5049
Pro His Ser His Ser Arg Thr Pro Glu Tyr Tyr Pro Asn Ala Gly Leu
        1655                1660                1665 atc atg aac tac tgc agg aat cca gat gct gtg gca gct cct tat tgt    5097
Ile Met Asn Tyr Cys Arg Asn Pro Asp Ala Val Ala Ala Pro Tyr Cys
1670                1675                1680 tat acg agg gat ccc ggt gtc agg tgg gag tac tgc aac ctg acg caa    5145
Tyr Thr Arg Asp Pro Gly Val Arg Trp Glu Tyr Cys Asn Leu Thr Gln
1685                1690                1695                1700 tgc tca gac gca gaa ggg act gcc gtc gcg cct ccg act gtt acc ccg    5193
Cys Ser Asp Ala Glu Gly Thr Ala Val Ala Pro Pro Thr Val Thr Pro
                1705                1710                1715 gtt cca agc cta gag gct cct tcc gaa caa gca ccg act gag caa agg    5241
Val Pro Ser Leu Glu Ala Pro Ser Glu Gln Ala Pro Thr Glu Gln Arg
            1720                1725                1730 cct ggg gtg cag gag tgc tac cat ggt aat gga cag agt tat cga ggc    5289
Pro Gly Val Gln Glu Cys Tyr His Gly Asn Gly Gln Ser Tyr Arg Gly
        1735                1740                1745 aca tac tcc acc act gtc aca gga aga acc tgc caa gct tgg tca tct    5337
Thr Tyr Ser Thr Thr Val Thr Gly Arg Thr Cys Gln Ala Trp Ser Ser
1750                1755                1760 atg aca cca cac tcg cat agt cgg acc cca gaa tac tac cca aat gct    5385
Met Thr Pro His Ser His Ser Arg Thr Pro Glu Tyr Tyr Pro Asn Ala
1765                1770                1775                1780 ggc ttg atc atg aac tac tgc agg aat cca gat gct gtg gca gct cct    5433
Gly Leu Ile Met Asn Tyr Cys Arg Asn Pro Asp Ala Val Ala Ala Pro
                1785                1790                1795 tat tgt tat acg agg gat ccc ggt gtc agg tgg gag tac tgc aac ctg    5481
Tyr Cys Tyr Thr Arg Asp Pro Gly Val Arg Trp Glu Tyr Cys Asn Leu
            1800                1805                1810 acg caa tgc tca gac gca gaa ggg act gcc gtc gcg cct ccg act gtt    5529
```

```
            Thr Gln Cys Ser Asp Ala Glu Gly Thr Ala Val Ala Pro Pro Thr Val
                    1815                1820                1825 acc ccg gtt cca agc cta gag gct cct tcc gaa caa gca ccg act gag          5577
Thr Pro Val Pro Ser Leu Glu Ala Pro Ser Glu Gln Ala Pro Thr Glu
1830                1835                1840 caa agg cct ggg gtg cag gag tgc tac cat ggt aat gga cag agt tat          5625
Gln Arg Pro Gly Val Gln Glu Cys Tyr His Gly Asn Gly Gln Ser Tyr
1845                1850                1855                1860 cga ggc aca tac tcc acc act gtc aca gga aga acc tgc caa gct tgg          5673
Arg Gly Thr Tyr Ser Thr Thr Val Thr Gly Arg Thr Cys Gln Ala Trp
        1865                1870                1875 tca tct atg aca cca cac tcg cat agt cgg acc cca gaa tac tac cca          5721
Ser Ser Met Thr Pro His Ser His Ser Arg Thr Pro Glu Tyr Tyr Pro
            1880                1885                1890 aat gct ggc ttg atc atg aac tac tgc agg aat cca gat gct gtg gca          5769
Asn Ala Gly Leu Ile Met Asn Tyr Cys Arg Asn Pro Asp Ala Val Ala
                1895                1900                1905 gct cct tat tgt tat acg agg gat ccc ggt gtc agg tgg gag tac tgc          5817
Ala Pro Tyr Cys Tyr Thr Arg Asp Pro Gly Val Arg Trp Glu Tyr Cys
1910                1915                1920 aac ctg acg caa tgc tca gac gca gaa ggg act gcc gtc gcg cct ccg          5865
Asn Leu Thr Gln Cys Ser Asp Ala Glu Gly Thr Ala Val Ala Pro Pro
1925                1930                1935                1940 act gtt acc ccg gtt cca agc cta gag gct cct tcc gaa caa gca ccg          5913
Thr Val Thr Pro Val Pro Ser Leu Glu Ala Pro Ser Glu Gln Ala Pro
            1945                1950                1955 act gag caa agg cct ggg gtg cag gag tgc tac cat ggt aat gga cag          5961
Thr Glu Gln Arg Pro Gly Val Gln Glu Cys Tyr His Gly Asn Gly Gln
                1960                1965                1970 agt tat cga ggc aca tac tcc acc act gtc aca gga aga acc tgc caa          6009
Ser Tyr Arg Gly Thr Tyr Ser Thr Thr Val Thr Gly Arg Thr Cys Gln
1975                1980                1985 gct tgg tca tct atg aca cca cac tcg cat agt cgg acc cca gaa tac          6057
Ala Trp Ser Ser Met Thr Pro His Ser His Ser Arg Thr Pro Glu Tyr
        1990                1995                2000 tac cca aat gct ggc ttg atc atg aac tac tgc agg aat cca gat gct          6105
Tyr Pro Asn Ala Gly Leu Ile Met Asn Tyr Cys Arg Asn Pro Asp Ala
2005                2010                2015                2020 gtg gca gct cct tat tgt tat acg agg gat ccc ggt gtc agg tgg gag          6153
Val Ala Ala Pro Tyr Cys Tyr Thr Arg Asp Pro Gly Val Arg Trp Glu
            2025                2030                2035 tac tgc aac ctg acg caa tgc tca gac gca gaa ggg act gcc gtc gcg          6201
Tyr Cys Asn Leu Thr Gln Cys Ser Asp Ala Glu Gly Thr Ala Val Ala
                2040                2045                2050 cct ccg act gtt acc ccg gtt cca agc cta gag gct cct tcc gaa caa          6249
Pro Pro Thr Val Thr Pro Val Pro Ser Leu Glu Ala Pro Ser Glu Gln
2055                2060                2065 gca ccg act gag caa agg cct ggg gtg cag gag tgc tac cat ggt aat          6297
Ala Pro Thr Glu Gln Arg Pro Gly Val Gln Glu Cys Tyr His Gly Asn
2070                2075                2080 gga cag agt tat cga ggc aca tac tcc acc act gtc aca gga aga acc          6345
Gly Gln Ser Tyr Arg Gly Thr Tyr Ser Thr Thr Val Thr Gly Arg Thr
2085                2090                2095                2100 tgc caa gct tgg tca tct atg aca cca cac tcg cat agt cgg acc cca          6393
Cys Gln Ala Trp Ser Ser Met Thr Pro His Ser His Ser Arg Thr Pro
            2105                2110                2115 gaa tac tac cca aat gct ggc ttg atc atg aac tac tgc agg aat cca          6441
Glu Tyr Tyr Pro Asn Ala Gly Leu Ile Met Asn Tyr Cys Arg Asn Pro
                2120                2125                2130 gat gct gtg gca gct cct tat tgt tat acg agg gat ccc ggt gtc agg          6489
```

-continued

| | | |
|---|---|---|
| Asp Ala Val Ala Ala Pro Tyr Cys Tyr Thr Arg Asp Pro Gly Val Arg<br>              2135                         2140                         2145 | |

```
tgg gag tac tgc aac ctg acg caa tgc tca gac gca gaa ggg act gcc      6537
Trp Glu Tyr Cys Asn Leu Thr Gln Cys Ser Asp Ala Glu Gly Thr Ala
             2150                2155                2160 gtc gcg cct ccg act gtt acc ccg gtt cca agc cta gag gct cct tcc      6585
Val Ala Pro Pro Thr Val Thr Pro Val Pro Ser Leu Glu Ala Pro Ser
2165                2170                2175                2180 gaa caa gca ccg act gag caa agg cct ggg gtg cag gag tgc tac cat      6633
Glu Gln Ala Pro Thr Glu Gln Arg Pro Gly Val Gln Glu Cys Tyr His
             2185                2190                2195 ggt aat gga cag agt tat cga ggc aca tac tcc acc act gtc aca gga      6681
Gly Asn Gly Gln Ser Tyr Arg Gly Thr Tyr Ser Thr Thr Val Thr Gly
             2200                2205                2210 aga acc tgc caa gct tgg tca tct atg aca cca cac tcg cat agt cgg      6729
Arg Thr Cys Gln Ala Trp Ser Ser Met Thr Pro His Ser His Ser Arg
             2215                2220                2225 acc cca gaa tac tac cca aat gct ggc ttg atc atg aac tac tgc agg      6777
Thr Pro Glu Tyr Tyr Pro Asn Ala Gly Leu Ile Met Asn Tyr Cys Arg
             2230                2235                2240 aat cca gat gct gtg gca gct cct tat tgt tat acg agg gat ccc ggt      6825
Asn Pro Asp Ala Val Ala Ala Pro Tyr Cys Tyr Thr Arg Asp Pro Gly
2245                2250                2255                2260 gtc agg tgg gag tac tgc aac ctg acg caa tgc tca gac gca gaa ggg      6873
Val Arg Trp Glu Tyr Cys Asn Leu Thr Gln Cys Ser Asp Ala Glu Gly
             2265                2270                2275 act gcc gtc gcg cct ccg act gtt acc ccg gtt cca agc cta gag gct      6921
Thr Ala Val Ala Pro Pro Thr Val Thr Pro Val Pro Ser Leu Glu Ala
             2280                2285                2290 cct tcc gaa caa gca ccg act gag caa agg cct ggg gtg cag gag tgc      6969
Pro Ser Glu Gln Ala Pro Thr Glu Gln Arg Pro Gly Val Gln Glu Cys
             2295                2300                2305 tac cat ggt aat gga cag agt tat cga ggc aca tac tcc acc act gtc      7017
Tyr His Gly Asn Gly Gln Ser Tyr Arg Gly Thr Tyr Ser Thr Thr Val
             2310                2315                2320 aca gga aga acc tgc caa gct tgg tca tct atg aca cca cac tcg cat      7065
Thr Gly Arg Thr Cys Gln Ala Trp Ser Ser Met Thr Pro His Ser His
2325                2330                2335                2340 agt cgg acc cca gaa tac tac cca aat gct ggc ttg atc atg aac tac      7113
Ser Arg Thr Pro Glu Tyr Tyr Pro Asn Ala Gly Leu Ile Met Asn Tyr
             2345                2350                2355 tgc agg aat cca gat gct gtg gca gct cct tat tgt tat acg agg gat      7161
Cys Arg Asn Pro Asp Ala Val Ala Ala Pro Tyr Cys Tyr Thr Arg Asp
             2360                2365                2370 ccc ggt gtc agg tgg gag tac tgc aac ctg acg caa tgc tca gac gca      7209
Pro Gly Val Arg Trp Glu Tyr Cys Asn Leu Thr Gln Cys Ser Asp Ala
             2375                2380                2385 gaa ggg act gcc gtc gcg cct ccg act gtt acc ccg gtt cca agc cta      7257
Glu Gly Thr Ala Val Ala Pro Pro Thr Val Thr Pro Val Pro Ser Leu
             2390                2395                2400 gag gct cct tcc gaa caa gca ccg act gag caa agg cct ggg gtg cag      7305
Glu Ala Pro Ser Glu Gln Ala Pro Thr Glu Gln Arg Pro Gly Val Gln
2405                2410                2415                2420 gag tgc tac cat ggt aat gga cag agt tat cga ggc aca tac tcc acc      7353
Glu Cys Tyr His Gly Asn Gly Gln Ser Tyr Arg Gly Thr Tyr Ser Thr
             2425                2430                2435 act gtc aca gga aga acc tgc caa gct tgg tca tct atg aca cca cac      7401
Thr Val Thr Gly Arg Thr Cys Gln Ala Trp Ser Ser Met Thr Pro His
             2440                2445                2450 tcg cat agt cgg acc cca gaa tac tac cca aat gct ggc ttg atc atg      7449
```

```
                                                                -continued

Ser His Ser Arg Thr Pro Glu Tyr Tyr Pro Asn Ala Gly Leu Ile Met
    2455                2460                2465 aac tac tgc agg aat cca gat gct gtg gca gct cct tat tgt tat acg       7497
Asn Tyr Cys Arg Asn Pro Asp Ala Val Ala Ala Pro Tyr Cys Tyr Thr
2470                2475                2480 agg gat ccc ggt gtc agg tgg gag tac tgc aac ctg acg caa tgc tca       7545
Arg Asp Pro Gly Val Arg Trp Glu Tyr Cys Asn Leu Thr Gln Cys Ser
2485                2490                2495                2500 gac gca gaa ggg act gcc gtc gcg cct ccg act gtt acc ccg gtt cca       7593
Asp Ala Glu Gly Thr Ala Val Ala Pro Pro Thr Val Thr Pro Val Pro
        2505                2510                2515 agc cta gag gct cct tcc gaa caa gca ccg act gag caa agg cct ggg       7641
Ser Leu Glu Ala Pro Ser Glu Gln Ala Pro Thr Glu Gln Arg Pro Gly
    2520                2525                2530 gtg cag gag tgc tac cat ggt aat gga cag agt tat cga ggc aca tac       7689
Val Gln Glu Cys Tyr His Gly Asn Gly Gln Ser Tyr Arg Gly Thr Tyr
        2535                2540                2545 tcc acc act gtc aca gga aga acc tgc caa gct tgg tca tct atg aca       7737
Ser Thr Thr Val Thr Gly Arg Thr Cys Gln Ala Trp Ser Ser Met Thr
    2550                2555                2560 cca cac tcg cat agt cgg acc cca gaa tac tac cca aat gct ggc ttg       7785
Pro His Ser His Ser Arg Thr Pro Glu Tyr Tyr Pro Asn Ala Gly Leu
2565                2570                2575                2580 atc atg aac tac tgc agg aat cca gat gct gtg gca gct cct tat tgt       7833
Ile Met Asn Tyr Cys Arg Asn Pro Asp Ala Val Ala Ala Pro Tyr Cys
        2585                2590                2595 tat acg agg gat ccc ggt gtc agg tgg gag tac tgc aac ctg acg caa       7881
Tyr Thr Arg Asp Pro Gly Val Arg Trp Glu Tyr Cys Asn Leu Thr Gln
    2600                2605                2610 tgc tca gac gca gaa ggg act gcc gtc gcg cct ccg act gtt acc ccg       7929
Cys Ser Asp Ala Glu Gly Thr Ala Val Ala Pro Pro Thr Val Thr Pro
        2615                2620                2625 gtt cca agc cta gag gct cct tcc gaa caa gca ccg act gag cag agg       7977
Val Pro Ser Leu Glu Ala Pro Ser Glu Gln Ala Pro Thr Glu Gln Arg
    2630                2635                2640 cct ggg gtg cag gag tgc tac cac ggt aat gga cag agt tat cga ggc       8025
Pro Gly Val Gln Glu Cys Tyr His Gly Asn Gly Gln Ser Tyr Arg Gly
2645                2650                2655                2660 aca tac tcc acc act gtc act gga aga acc tgc caa gct tgg tca tct       8073
Thr Tyr Ser Thr Thr Val Thr Gly Arg Thr Cys Gln Ala Trp Ser Ser
        2665                2670                2675 atg aca cca cac tcg cat agt cgg acc cca gaa tac tac cca aat gct       8121
Met Thr Pro His Ser His Ser Arg Thr Pro Glu Tyr Tyr Pro Asn Ala
            2680                2685                2690 ggc ttg atc atg aac tac tgc agg aat cca gat gct gtg gca gct cct       8169
Gly Leu Ile Met Asn Tyr Cys Arg Asn Pro Asp Ala Val Ala Ala Pro
        2695                2700                2705 tat tgt tat acg agg gat ccc ggt gtc agg tgg gag tac tgc aac ctg       8217
Tyr Cys Tyr Thr Arg Asp Pro Gly Val Arg Trp Glu Tyr Cys Asn Leu
    2710                2715                2720 acg caa tgc tca gac gca gaa ggg act gcc gtc gcg cct ccg act gtt       8265
Thr Gln Cys Ser Asp Ala Glu Gly Thr Ala Val Ala Pro Pro Thr Val
2725                2730                2735                2740 acc ccg gtt cca agc cta gag gct cct tcc gaa caa gca ccg act gag       8313
Thr Pro Val Pro Ser Leu Glu Ala Pro Ser Glu Gln Ala Pro Thr Glu
        2745                2750                2755 caa agg cct ggg gtg cag gag tgc tac cat ggt aat gga cag agt tat       8361
Gln Arg Pro Gly Val Gln Glu Cys Tyr His Gly Asn Gly Gln Ser Tyr
        2760                2765                2770 cga ggc aca tac tcc acc act gtc aca gga aga acc tgc caa gct tgg       8409
```

-continued

```
Arg Gly Thr Tyr Ser Thr Thr Val Thr Gly Arg Thr Cys Gln Ala Trp
        2775                2780                2785 tca tct atg aca cca cac tcg cat agt cgg acc cca gaa tac tac cca         8457
Ser Ser Met Thr Pro His Ser His Ser Arg Thr Pro Glu Tyr Tyr Pro
2790                2795                2800 aat gct ggc ttg atc atg aac tac tgc agg aat cca gat gct gtg gca         8505
Asn Ala Gly Leu Ile Met Asn Tyr Cys Arg Asn Pro Asp Ala Val Ala
2805                2810                2815                2820 gct cct tat tgt tat acg agg gat ccc ggt gtc agg tgg gag tac tgc         8553
Ala Pro Tyr Cys Tyr Thr Arg Asp Pro Gly Val Arg Trp Glu Tyr Cys
            2825                2830                2835 aac ctg acg caa tgc tca gac gca gaa ggg act gcc gtc gcg cct ccg         8601
Asn Leu Thr Gln Cys Ser Asp Ala Glu Gly Thr Ala Val Ala Pro Pro
        2840                2845                2850 act gtt acc ccg gtt cca agc cta gag gct cct tcc gaa caa gca ccg         8649
Thr Val Thr Pro Val Pro Ser Leu Glu Ala Pro Ser Glu Gln Ala Pro
                2855                2860                2865 act gag caa agg cct ggg gtg cag gag tgc tac cat ggt aat gga cag         8697
Thr Glu Gln Arg Pro Gly Val Gln Glu Cys Tyr His Gly Asn Gly Gln
2870                2875                2880 agt tat cga ggc aca tac tcc acc act gtc aca gga aga acc tgc caa         8745
Ser Tyr Arg Gly Thr Tyr Ser Thr Thr Val Thr Gly Arg Thr Cys Gln
2885                2890                2895                2900 gct tgg tca tct atg aca cca cac tcg cat agt cgg acc cca gaa tac         8793
Ala Trp Ser Ser Met Thr Pro His Ser His Ser Arg Thr Pro Glu Tyr
            2905                2910                2915 tac cca aat gct ggc ttg atc atg aac tac tgc agg aat cca gat gct         8841
Tyr Pro Asn Ala Gly Leu Ile Met Asn Tyr Cys Arg Asn Pro Asp Ala
        2920                2925                2930 gtg gca gct cct tat tgt tat acg agg gat ccc ggt gtc agg tgg gag         8889
Val Ala Ala Pro Tyr Cys Tyr Thr Arg Asp Pro Gly Val Arg Trp Glu
                2935                2940                2945 tac tgc aac ctg acg caa tgc tca gac gca gaa ggg act gcc gtc gcg         8937
Tyr Cys Asn Leu Thr Gln Cys Ser Asp Ala Glu Gly Thr Ala Val Ala
2950                2955                2960 cct ccg act gtt acc ccg gtt cca agc cta gag gct cct tcc gaa caa         8985
Pro Pro Thr Val Thr Pro Val Pro Ser Leu Glu Ala Pro Ser Glu Gln
2965                2970                2975                2980 gca ccg act gag cag agg cct ggg gtg cag gag tgc tac cac ggt aat         9033
Ala Pro Thr Glu Gln Arg Pro Gly Val Gln Glu Cys Tyr His Gly Asn
            2985                2990                2995 gga cag agt tat cga ggc aca tac tcc acc act gtc act gga aga acc         9081
Gly Gln Ser Tyr Arg Gly Thr Tyr Ser Thr Thr Val Thr Gly Arg Thr
        3000                3005                3010 tgc caa gct tgg tca tct atg aca cca cac tcg cat agt cgg acc cca         9129
Cys Gln Ala Trp Ser Ser Met Thr Pro His Ser His Ser Arg Thr Pro
                3015                3020                3025 gaa tac tac cca aat gct ggc ttg atc atg aac tac tgc agg aat cca         9177
Glu Tyr Tyr Pro Asn Ala Gly Leu Ile Met Asn Tyr Cys Arg Asn Pro
3030                3035                3040 gat gct gtg gca gct cct tat tgt tat acg agg gat ccc ggt gtc agg         9225
Asp Ala Val Ala Ala Pro Tyr Cys Tyr Thr Arg Asp Pro Gly Val Arg
3045                3050                3055                3060 tgg gag tac tgc aac ctg acg caa tgc tca gac gca gaa ggg act gcc         9273
Trp Glu Tyr Cys Asn Leu Thr Gln Cys Ser Asp Ala Glu Gly Thr Ala
            3065                3070                3075 gtc gcg cct ccg act gtt acc ccg gtt cca agc cta gag gct cct tcc         9321
Val Ala Pro Pro Thr Val Thr Pro Val Pro Ser Leu Glu Ala Pro Ser
        3080                3085                3090 gaa caa gca ccg act gag cag agg cct ggg gtg cag gag tgc tac cac         9369
```

```
Glu Gln Ala Pro Thr Glu Gln Arg Pro Gly Val Gln Glu Cys Tyr His
        3095                3100                3105 ggt aat gga cag agt tat cga ggc aca tac tcc acc act gtc act gga       9417
Gly Asn Gly Gln Ser Tyr Arg Gly Thr Tyr Ser Thr Thr Val Thr Gly
    3110                3115                3120 aga acc tgc caa gct tgg tca tct atg aca cca cac tcg cat agt cgg       9465
Arg Thr Cys Gln Ala Trp Ser Ser Met Thr Pro His Ser His Ser Arg
3125                3130                3135                3140 acc cca gaa tac tac cca aat gct ggc ttg atc atg aac tac tgc agg       9513
Thr Pro Glu Tyr Tyr Pro Asn Ala Gly Leu Ile Met Asn Tyr Cys Arg
            3145                3150                3155 aat cca gat gct gtg gca gct cct tat tgt tat acg agg gat ccc ggt       9561
Asn Pro Asp Ala Val Ala Ala Pro Tyr Cys Tyr Thr Arg Asp Pro Gly
        3160                3165                3170 gtc agg tgg gag tac tgc aac ctg acg caa tgc tca gac gca gaa ggg       9609
Val Arg Trp Glu Tyr Cys Asn Leu Thr Gln Cys Ser Asp Ala Glu Gly
    3175                3180                3185 act gcc gtc gcg cct ccg act gtt acc ccg gtt cca agc cta gag gct       9657
Thr Ala Val Ala Pro Pro Thr Val Thr Pro Val Pro Ser Leu Glu Ala
3190                3195                3200 cct tcc gaa caa gca ccg act gag cag agg cct ggg gtg cag gag tgc       9705
Pro Ser Glu Gln Ala Pro Thr Glu Gln Arg Pro Gly Val Gln Glu Cys
3205                3210                3215                3220 tac cac ggt aat gga cag agt tat cga ggc aca tac tcc acc act gtc       9753
Tyr His Gly Asn Gly Gln Ser Tyr Arg Gly Thr Tyr Ser Thr Thr Val
            3225                3230                3235 act gga aga acc tgc caa gct tgg tca tct atg aca cca cac tcg cat       9801
Thr Gly Arg Thr Cys Gln Ala Trp Ser Ser Met Thr Pro His Ser His
        3240                3245                3250 agt cgg acc cca gaa tac tac cca aat gct ggc ttg atc atg aac tac       9849
Ser Arg Thr Pro Glu Tyr Tyr Pro Asn Ala Gly Leu Ile Met Asn Tyr
    3255                3260                3265 tgc agg aat cca gat gct gtg gca gct cct tat tgt tat acg agg gat       9897
Cys Arg Asn Pro Asp Ala Val Ala Ala Pro Tyr Cys Tyr Thr Arg Asp
3270                3275                3280 ccc ggt gtc agg tgg gag tac tgc aac ctg acg caa tgc tca gac gca       9945
Pro Gly Val Arg Trp Glu Tyr Cys Asn Leu Thr Gln Cys Ser Asp Ala
3285                3290                3295                3300 gaa ggg act gcc gtc gcg cct ccg act gtt acc ccg gtt cca agc cta       9993
Glu Gly Thr Ala Val Ala Pro Pro Thr Val Thr Pro Val Pro Ser Leu
            3305                3310                3315 gag gct cct tcc gaa caa gca ccg act gag cag agg cct ggg gtg cag      10041
Glu Ala Pro Ser Glu Gln Ala Pro Thr Glu Gln Arg Pro Gly Val Gln
        3320                3325                3330 gag tgc tac cac ggt aat gga cag agt tat cga ggc aca tac tcc acc      10089
Glu Cys Tyr His Gly Asn Gly Gln Ser Tyr Arg Gly Thr Tyr Ser Thr
    3335                3340                3345 act gtc act gga aga acc tgc caa gct tgg tca tct atg aca cca cac      10137
Thr Val Thr Gly Arg Thr Cys Gln Ala Trp Ser Ser Met Thr Pro His
3350                3355                3360 tcg cat agt cgg acc cca gaa tac tac cca aat gct ggc ttg atc atg      10185
Ser His Ser Arg Thr Pro Glu Tyr Tyr Pro Asn Ala Gly Leu Ile Met
3365                3370                3375                3380 aac tac tgc agg aat cca gat cct gtg gca gcc cct tat tgt tat acg      10233
Asn Tyr Cys Arg Asn Pro Asp Pro Val Ala Ala Pro Tyr Cys Tyr Thr
            3385                3390                3395 agg gat ccc agt gtc agg tgg gag tac tgc aac ctg aca caa tgc tca      10281
Arg Asp Pro Ser Val Arg Trp Glu Tyr Cys Asn Leu Thr Gln Cys Ser
        3400                3405                3410 gac gca gaa ggg act gcc gtc gcg cct cca act att acc ccg att cca      10329
```

```
                    -continued

Asp Ala Glu Gly Thr Ala Val Ala Pro Pro Thr Ile Thr Pro Ile Pro
        3415                3420                3425 agc cta gag gct cct tct gaa caa gca cca act gag caa agg cct ggg    10377
Ser Leu Glu Ala Pro Ser Glu Gln Ala Pro Thr Glu Gln Arg Pro Gly
    3430                3435                3440 gtg cag gag tgc tac cac gga aat gga cag agt tat caa ggc aca tac    10425
Val Gln Glu Cys Tyr His Gly Asn Gly Gln Ser Tyr Gln Gly Thr Tyr
3445                3450                3455                3460 ttc att act gtc aca gga aga acc tgc caa gct tgg tca tct atg aca    10473
Phe Ile Thr Val Thr Gly Arg Thr Cys Gln Ala Trp Ser Ser Met Thr
                3465                3470                3475 cca cac tcg cat agt cgg acc cca gca tac tac cca aat gct ggc ttg    10521
Pro His Ser His Ser Arg Thr Pro Ala Tyr Tyr Pro Asn Ala Gly Leu
            3480                3485                3490 atc aag aac tac tgc cga aat cca gat cct gtg gca gcc cct tgg tgt    10569
Ile Lys Asn Tyr Cys Arg Asn Pro Asp Pro Val Ala Ala Pro Trp Cys
        3495                3500                3505 tat aca aca gat ccc agt gtc agg tgg gag tac tgc aac ctg aca cga    10617
Tyr Thr Thr Asp Pro Ser Val Arg Trp Glu Tyr Cys Asn Leu Thr Arg
    3510                3515                3520 tgc tca gat gca gaa tgg act gcc ttc gtc cct ccg aat gtt att ctg    10665
Cys Ser Asp Ala Glu Trp Thr Ala Phe Val Pro Pro Asn Val Ile Leu
3525                3530                3535                3540 gct cca agc cta gag gct ttt ttt gaa caa gca ctg act gag gaa acc    10713
Ala Pro Ser Leu Glu Ala Phe Phe Glu Gln Ala Leu Thr Glu Glu Thr
                3545                3550                3555 ccc ggg gta cag gac tgc tac tac cat tat gga cag agt tac cga ggc    10761
Pro Gly Val Gln Asp Cys Tyr Tyr His Tyr Gly Gln Ser Tyr Arg Gly
            3560                3565                3570 aca tac tcc acc act gtc aca gga aga act tgc caa gct tgg tca tct    10809
Thr Tyr Ser Thr Thr Val Thr Gly Arg Thr Cys Gln Ala Trp Ser Ser
        3575                3580                3585 atg aca cca cac cag cat agt cgg acc cca gaa aac tac cca aat gct    10857
Met Thr Pro His Gln His Ser Arg Thr Pro Glu Asn Tyr Pro Asn Ala
    3590                3595                3600 ggc ctg acc agg aac tac tgc agg aat cca gat gct gag att cgc cct    10905
Gly Leu Thr Arg Asn Tyr Cys Arg Asn Pro Asp Ala Glu Ile Arg Pro
3605                3610                3615                3620 tgg tgt tac acc atg gat ccc agt gtc agg tgg gag tac tgc aac ctg    10953
Trp Cys Tyr Thr Met Asp Pro Ser Val Arg Trp Glu Tyr Cys Asn Leu
                3625                3630                3635 aca caa tgc ctg gtg aca gaa tca agt gtc ctt gca act ctc acg gtg    11001
Thr Gln Cys Leu Val Thr Glu Ser Ser Val Leu Ala Thr Leu Thr Val
            3640                3645                3650 gtc cca gat cca agc aca gag gct tct tct gaa gaa gca cca acg gag    11049
Val Pro Asp Pro Ser Thr Glu Ala Ser Ser Glu Glu Ala Pro Thr Glu
        3655                3660                3665 caa agc ccc ggg gtc cag gat tgc tac cat ggt gat gga cag agt tat    11097
Gln Ser Pro Gly Val Gln Asp Cys Tyr His Gly Asp Gly Gln Ser Tyr
    3670                3675                3680 cga ggc tca ttc tct acc act gtc aca gga agg aca tgt cag tct tgg    11145
Arg Gly Ser Phe Ser Thr Thr Val Thr Gly Arg Thr Cys Gln Ser Trp
3685                3690                3695                3700 tcc tct atg aca cca cac tgg cat cag agg aca aca gaa tat tat cca    11193
Ser Ser Met Thr Pro His Trp His Gln Arg Thr Thr Glu Tyr Tyr Pro
                3705                3710                3715 aat ggt ggc ctg acc agg aac tac tgc agg aat cca gat gct gag att    11241
Asn Gly Gly Leu Thr Arg Asn Tyr Cys Arg Asn Pro Asp Ala Glu Ile
            3720                3725                3730 agt cct tgg tgt tat acc atg gat ccc aat gtc aga tgg gag tac tgc    11289
```

```
              Ser Pro Trp Cys Tyr Thr Met Asp Pro Asn Val Arg Trp Glu Tyr Cys
                      3735                3740                3745 aac ctg aca caa tgt cca gtg aca gaa tca agt gtc ctt gcg acg tcc              11337
Asn Leu Thr Gln Cys Pro Val Thr Glu Ser Ser Val Leu Ala Thr Ser
3750                3755                3760 acg gct gtt tct gaa caa gca cca acg gag caa agc ccc aca gtc cag              11385
Thr Ala Val Ser Glu Gln Ala Pro Thr Glu Gln Ser Pro Thr Val Gln
3765                3770                3775                3780 gac tgc tac cat ggt gat gga cag agt tat cga ggc tca ttc tcc acc              11433
Asp Cys Tyr His Gly Asp Gly Gln Ser Tyr Arg Gly Ser Phe Ser Thr
                3785                3790                3795 act gtt aca gga agg aca tgt cag tct tgg tcc tct atg aca cca cac              11481
Thr Val Thr Gly Arg Thr Cys Gln Ser Trp Ser Ser Met Thr Pro His
            3800                3805                3810 tgg cat cag aga acc aca gaa tac tac cca aat ggt ggc ctg acc agg              11529
Trp His Gln Arg Thr Thr Glu Tyr Tyr Pro Asn Gly Gly Leu Thr Arg
            3815                3820                3825 aac tac tgc agg aat cca gat gct gag att cgc cct tgg tgt tat acc              11577
Asn Tyr Cys Arg Asn Pro Asp Ala Glu Ile Arg Pro Trp Cys Tyr Thr
            3830                3835                3840 atg gat ccc agt gtc aga tgg gag tac tgc aac ctg acg caa tgt cca              11625
Met Asp Pro Ser Val Arg Trp Glu Tyr Cys Asn Leu Thr Gln Cys Pro
3845                3850                3855                3860 gtg atg gaa tca act ctc ctc aca act ccc acg gtg gtc cca gtt cca              11673
Val Met Glu Ser Thr Leu Leu Thr Thr Pro Thr Val Val Pro Val Pro
                3865                3870                3875 agc aca gag ctt cct tct gaa gaa gca cca act gaa aac agc act ggg              11721
Ser Thr Glu Leu Pro Ser Glu Glu Ala Pro Thr Glu Asn Ser Thr Gly
            3880                3885                3890 gtc cag gac tgc tac cga ggt gat gga cag agt tat cga ggc aca ctc              11769
Val Gln Asp Cys Tyr Arg Gly Asp Gly Gln Ser Tyr Arg Gly Thr Leu
            3895                3900                3905 tcc acc act atc aca gga aga aca tgt cag tct tgg tcg tct atg aca              11817
Ser Thr Thr Ile Thr Gly Arg Thr Cys Gln Ser Trp Ser Ser Met Thr
            3910                3915                3920 cca cat tgg cat cgg agg atc cca tta tac tat cca aat gct ggc ctg              11865
Pro His Trp His Arg Arg Ile Pro Leu Tyr Tyr Pro Asn Ala Gly Leu
3925                3930                3935                3940 acc agg aac tac tgc agg aat cca gat gct gag att cgc cct tgg tgt              11913
Thr Arg Asn Tyr Cys Arg Asn Pro Asp Ala Glu Ile Arg Pro Trp Cys
                3945                3950                3955 tac acc atg gat ccc agt gtc agg tgg gag tac tgc aac ctg aca cga              11961
Tyr Thr Met Asp Pro Ser Val Arg Trp Glu Tyr Cys Asn Leu Thr Arg
            3960                3965                3970 tgt cca gtg aca gaa tcg agt gtc ctc aca act ccc aca gtg gcc ccg              12009
Cys Pro Val Thr Glu Ser Ser Val Leu Thr Thr Pro Thr Val Ala Pro
            3975                3980                3985 gtt cca agc aca gag gct cct tct gaa caa gca cca cct gag aaa agc              12057
Val Pro Ser Thr Glu Ala Pro Ser Glu Gln Ala Pro Pro Glu Lys Ser
3990                3995                4000 cct gtg gtc cag gat tgc tac cat ggt gat gga cgg agt tat cga ggc              12105
Pro Val Val Gln Asp Cys Tyr His Gly Asp Gly Arg Ser Tyr Arg Gly
4005                4010                4015                4020 ata tcc tcc acc act gtc aca gga agg acc tgt caa tct tgg tca tct              12153
Ile Ser Ser Thr Thr Val Thr Gly Arg Thr Cys Gln Ser Trp Ser Ser
            4025                4030                4035 atg ata cca cac tgg cat cag agg acc cca gaa aac tac cca aat gct              12201
Met Ile Pro His Trp His Gln Arg Thr Pro Glu Asn Tyr Pro Asn Ala
            4040                4045                4050 ggc ctg acc gag aac tac tgc agg aat cca gat tct ggg aaa caa ccc              12249
```

|  |  |
|---|---|
| Gly Leu Thr Glu Asn Tyr Cys Arg Asn Pro Asp Ser Gly Lys Gln Pro<br>            4055                      4060                  4065 |  |
| tgg tgt tac aca acc gat ccg tgt gtg agg tgg gag tac tgc aat ctg<br>Trp Cys Tyr Thr Thr Asp Pro Cys Val Arg Trp Glu Tyr Cys Asn Leu<br>4070                    4075                    4080 | 12297 |
| aca caa tgc tca gaa aca gaa tca ggt gtc cta gag act ccc act gtt<br>Thr Gln Cys Ser Glu Thr Glu Ser Gly Val Leu Glu Thr Pro Thr Val<br>4085                    4090                    4095                    4100 | 12345 |
| gtt cca gtt cca agc atg gag gct cat tct gaa gca gca cca act gag<br>Val Pro Val Pro Ser Met Glu Ala His Ser Glu Ala Ala Pro Thr Glu<br>                    4105                    4110                    4115 | 12393 |
| caa acc cct gtg gtc cgg cag tgc tac cat ggt aat ggc cag agt tat<br>Gln Thr Pro Val Val Arg Gln Cys Tyr His Gly Asn Gly Gln Ser Tyr<br>                4120                    4125                    4130 | 12441 |
| cga ggc aca ttc tcc acc act gtc aca gga agg aca tgt caa tct tgg<br>Arg Gly Thr Phe Ser Thr Thr Val Thr Gly Arg Thr Cys Gln Ser Trp<br>                4135                    4140                    4145 | 12489 |
| tca tcc atg aca cca cac cgg cat cag agg acc cca gaa aac tac cca<br>Ser Ser Met Thr Pro His Arg His Gln Arg Thr Pro Glu Asn Tyr Pro<br>                4150                    4155                    4160 | 12537 |
| aat gat ggc ctg aca atg aac tac tgc agg aat cca gat gcc gat aca<br>Asn Asp Gly Leu Thr Met Asn Tyr Cys Arg Asn Pro Asp Ala Asp Thr<br>4165                    4170                    4175                    4180 | 12585 |
| ggc cct tgg tgt ttt acc atg gac ccc agc atc agg tgg gag tac tgc<br>Gly Pro Trp Cys Phe Thr Met Asp Pro Ser Ile Arg Trp Glu Tyr Cys<br>                4185                    4190                    4195 | 12633 |
| aac ctg acg cga tgc tca gac aca gaa ggg act gtg gtc gct cct ccg<br>Asn Leu Thr Arg Cys Ser Asp Thr Glu Gly Thr Val Val Ala Pro Pro<br>                4200                    4205                    4210 | 12681 |
| act gtc atc cag gtt cca agc cta ggg cct cct tct gaa caa gac tgt<br>Thr Val Ile Gln Val Pro Ser Leu Gly Pro Pro Ser Glu Gln Asp Cys<br>            4215                    4220                    4225 | 12729 |
| atg ttt ggg aat ggg aaa gga tac cgg ggc aag aag gca acc act gtt<br>Met Phe Gly Asn Gly Lys Gly Tyr Arg Gly Lys Lys Ala Thr Thr Val<br>            4230                    4235                    4240 | 12777 |
| act ggg acg cca tgc cag gaa tgg gct gcc cag gag ccc cat aga cac<br>Thr Gly Thr Pro Cys Gln Glu Trp Ala Ala Gln Glu Pro His Arg His<br>4245                    4250                    4255                    4260 | 12825 |
| agc acg ttc att cca ggg aca aat aaa tgg gca ggt ctg gaa aaa aat<br>Ser Thr Phe Ile Pro Gly Thr Asn Lys Trp Ala Gly Leu Glu Lys Asn<br>                4265                    4270                    4275 | 12873 |
| tac tgc cgt aac cct gat ggt gac atc aat ggt ccc tgg tgc tac aca<br>Tyr Cys Arg Asn Pro Asp Gly Asp Ile Asn Gly Pro Trp Cys Tyr Thr<br>                    4280                    4285                    4290 | 12921 |
| atg aat cca aga aaa ctt ttt gac tac tgt gat atc cct ctc tgt gca<br>Met Asn Pro Arg Lys Leu Phe Asp Tyr Cys Asp Ile Pro Leu Cys Ala<br>                4295                    4300                    4305 | 12969 |
| tcc tct tca ttt gat tgt ggg aag cct caa gtg gag ccg aag aaa tgt<br>Ser Ser Ser Phe Asp Cys Gly Lys Pro Gln Val Glu Pro Lys Lys Cys<br>            4310                    4315                    4320 | 13017 |
| cct gga agc att gta ggg ggg tgt gtg gcc cac cca cat tcc tgg ccc<br>Pro Gly Ser Ile Val Gly Gly Cys Val Ala His Pro His Ser Trp Pro<br>4325                    4330                    4335                    4340 | 13065 |
| tgg caa gtc agt ctc aga aca agg ttt gga aag cac ttc tgt gga ggc<br>Trp Gln Val Ser Leu Arg Thr Arg Phe Gly Lys His Phe Cys Gly Gly<br>                4345                    4350                    4355 | 13113 |
| acc tta ata tcc cca gag tgg gtg ctg act gct gct cac tgc ttg aag<br>Thr Leu Ile Ser Pro Glu Trp Val Leu Thr Ala Ala His Cys Leu Lys<br>                4360                    4365                    4370 | 13161 |
| aag tcc tca agg cct tca tcc tac aag gtc atc ctg ggt gca cac caa | 13209 |

```
                 Lys Ser Ser Arg Pro Ser Ser Tyr Lys Val Ile Leu Gly Ala His Gln
                     4375                4380                4385 gaa gtg aac ctc gaa tct cat gtt cag gaa ata gaa gtg tct agg ctg       13257
Glu Val Asn Leu Glu Ser His Val Gln Glu Ile Glu Val Ser Arg Leu
    4390                4395                4400 ttc ttg gag ccc aca caa gca gat att gcc ttg cta aag cta agc agg       13305
Phe Leu Glu Pro Thr Gln Ala Asp Ile Ala Leu Leu Lys Leu Ser Arg
4405                4410                4415                4420 cct gcc gtc atc act gac aaa gta atg cca gct tgt ctg cca tcc cca       13353
Pro Ala Val Ile Thr Asp Lys Val Met Pro Ala Cys Leu Pro Ser Pro
                4425                4430                4435 gac tac atg gtc acc gcc agg act gaa tgt tac atc act ggc tgg gga       13401
Asp Tyr Met Val Thr Ala Arg Thr Glu Cys Tyr Ile Thr Gly Trp Gly
            4440                4445                4450 gaa acc caa ggt acc ttt ggg act ggc ctt ctc aag gaa gcc cag ctc       13449
Glu Thr Gln Gly Thr Phe Gly Thr Gly Leu Leu Lys Glu Ala Gln Leu
                4455                4460                4465 ctt gtt att gag aat gaa gtg tgc aat cac tat aag tat att tgt gct       13497
Leu Val Ile Glu Asn Glu Val Cys Asn His Tyr Lys Tyr Ile Cys Ala
    4470                4475                4480 gag cat ttg gcc aga ggc act gac agt tgc cag ggt gac agt gga ggg       13545
Glu His Leu Ala Arg Gly Thr Asp Ser Cys Gln Gly Asp Ser Gly Gly
4485                4490                4495                4500 cct ctg gtt tgc ttc gag aag gac aaa tac att tta caa gga gtc act       13593
Pro Leu Val Cys Phe Glu Lys Asp Lys Tyr Ile Leu Gln Gly Val Thr
                4505                4510                4515 tct tgg ggt ctt ggc tgt gca cgc ccc aat aag cct ggt gtc tat gct       13641
Ser Trp Gly Leu Gly Cys Ala Arg Pro Asn Lys Pro Gly Val Tyr Ala
            4520                4525                4530 cgt gtt tca agg ttt gtt act tgg att gag gga atg atg aga aat aat       13689
Arg Val Ser Arg Phe Val Thr Trp Ile Glu Gly Met Met Arg Asn Asn
                4535                4540                4545 taa ttggacggga gacagagtga agcatcaacc tacttagaag ctgaaacgtg            13742
* ggtaaggatt tagcatgctg gaaataatag acagcaatca aacgaagaca ctgttcccag     13802
ctaccagcta tgccaaacct tggcattttt ggtattttg tgtataagct tttaaggtct     13862
gactgacaaa ttctgtatta aggtgtcata gctatgacat ttgttaaaaa taaactctgc     13922
acttattttg atttga                                                     13938

<210> SEQ ID NO 5
<211> LENGTH: 25
<212> TYPE: DNA
<213> ORGANISM: Artificial Sequence
<220> FEATURE:
<223> OTHER INFORMATION: PCR Primer

<400> SEQUENCE: 5
cagctcctta ttgttatacg aggga                                           25

<210> SEQ ID NO 6
<211> LENGTH: 18
<212> TYPE: DNA
<213> ORGANISM: Artificial Sequence
<220> FEATURE:
<223> OTHER INFORMATION: PCR Primer

<400> SEQUENCE: 6
tgcgtctgag cattgcgt                                                   18

<210> SEQ ID NO 7
```

```
<211> LENGTH: 24
<212> TYPE: DNA
<213> ORGANISM: Artificial Sequence
<220> FEATURE:
<223> OTHER INFORMATION: PCR Probe

<400> SEQUENCE: 7
cccggtgtca ggtgggagta ctgc                                          24

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
ggcaaattca acggcacagt                                               20

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gggtctcgct cctggaagat                                               20

<210> SEQ ID NO 10
<211> LENGTH: 27
<212> TYPE: DNA
<213> ORGANISM: Artificial Sequence
<220> FEATURE:
<223> OTHER INFORMATION: PCR Probe

<400> SEQUENCE: 10
aaggccgaga atgggaagct tgtcatc                                       27

<210> SEQ ID NO 11
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 11
ggcaggtcct tcctgtgaca                                               20

<210> SEQ ID NO 12
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 12
tctgcgtctg agcattgcgt                                               20

<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13
```

-continued aagcttggca ggttcttcct 20

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
tcggaggcgc gacggcagtc 20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
cggaggcgcg acggcagtcc 20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
ggcaggttct tcctgtgaca 20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
ataacaataa ggagctgcca 20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
gaccaagctt ggcaggttct 20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
taacaataag gagctgccac 20

<210> SEQ ID NO 20
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 20
tgaccaagct tggcaggttc                                                    20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
ttctgcgtct gagcattgcg                                                    20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
aacaataagg agctgccaca                                                    20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
acctgacacc gggatccctc                                                    20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
ctgagcattg cgtcaggttg                                                    20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
agtagttcat gatcaagcca                                                    20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
gacggcagtc ccttctgcgt                                                    20

<210> SEQ ID NO 27
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
ggcaggttct tccagtgaca                                                    20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
tgaccaagct tggcaagttc                                                    20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
tataacacca aggactaatc                                                    20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
ccatctgaca ttgggatcca                                                    20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
tgtggtgtca tagaggacca                                                    20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
atgggatcct ccgatgccaa                                                    20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
```

```
acaccaaggg cgaatctcag                                         20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
ttctgtcact ggacatcgtg                                         20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
cacacggatc ggttgtgtaa                                         20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
acatgtcctt cctgtgacag                                         20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
cagaaggagg ccctaggctt                                         20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
ctggcggtga ccatgtagtc                                         20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
tctaagtagg ttgatgcttc                                         20

<210> SEQ ID NO 40
<211> LENGTH: 20
<212> TYPE: DNA
<213> ORGANISM: Artificial Sequence
<220> FEATURE:
```

```
<223> OTHER INFORMATION: Antisense Oligonucleotide

<400> SEQUENCE: 40
tccttaccca cgtttcagct                                               20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
ggaacagtgt cttcgtttga                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
gtttggcata gctggtagct                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
accttaaaag cttatacaca                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
atacagaatt tgtcagtcag                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
gtcatagcta tgacacctta                                               20

<210> SEQ ID NO 46
<211> LENGTH: 20
<212> TYPE: DNA
<213> ORGANISM: H. sapiens
<220> FEATURE:

<400> SEQUENCE: 46
tgtcacagga aggacctgcc                                               20

<210> SEQ ID NO 47
<211> LENGTH: 20
```

```
<212> TYPE: DNA
<213> ORGANISM: H. sapiens
<220> FEATURE:

<400> SEQUENCE: 47
acgcaatgct cagacgcaga                                              20

<210> SEQ ID NO 48
<211> LENGTH: 20
<212> TYPE: DNA
<213> ORGANISM: H. sapiens
<220> FEATURE:

<400> SEQUENCE: 48
gactgccgtc gcgcctccga                                              20

<210> SEQ ID NO 49
<211> LENGTH: 20
<212> TYPE: DNA
<213> ORGANISM: H. sapiens
<220> FEATURE:

<400> SEQUENCE: 49
tgtcacagga agaacctgcc                                              20

<210> SEQ ID NO 50
<211> LENGTH: 20
<212> TYPE: DNA
<213> ORGANISM: H. sapiens
<220> FEATURE:

<400> SEQUENCE: 50
tggcagctcc ttattgttat                                              20

<210> SEQ ID NO 51
<211> LENGTH: 20
<212> TYPE: DNA
<213> ORGANISM: H. sapiens
<220> FEATURE:

<400> SEQUENCE: 51
agaacctgcc aagcttggtc                                              20

<210> SEQ ID NO 52
<211> LENGTH: 20
<212> TYPE: DNA
<213> ORGANISM: H. sapiens
<220> FEATURE:

<400> SEQUENCE: 52
gtggcagctc cttattgtta                                              20

<210> SEQ ID NO 53
<211> LENGTH: 20
<212> TYPE: DNA
<213> ORGANISM: H. sapiens
<220> FEATURE:

<400> SEQUENCE: 53
cgcaatgctc agacgcagaa                                              20

<210> SEQ ID NO 54
<211> LENGTH: 20
<212> TYPE: DNA
<213> ORGANISM: H. sapiens
<220> FEATURE:
```

```
<400> SEQUENCE: 54
gagggatccc ggtgtcaggt                                              20

<210> SEQ ID NO 55
<211> LENGTH: 20
<212> TYPE: DNA
<213> ORGANISM: H. sapiens
<220> FEATURE:

<400> SEQUENCE: 55
tggcttgatc atgaactact                                              20

<210> SEQ ID NO 56
<211> LENGTH: 20
<212> TYPE: DNA
<213> ORGANISM: H. sapiens
<220> FEATURE:

<400> SEQUENCE: 56
tggatcccaa tgtcagatgg                                              20

<210> SEQ ID NO 57
<211> LENGTH: 20
<212> TYPE: DNA
<213> ORGANISM: H. sapiens
<220> FEATURE:

<400> SEQUENCE: 57
tggtcctcta tgacaccaca                                              20

<210> SEQ ID NO 58
<211> LENGTH: 20
<212> TYPE: DNA
<213> ORGANISM: H. sapiens
<220> FEATURE:

<400> SEQUENCE: 58
ttggcatcgg aggatcccat                                              20

<210> SEQ ID NO 59
<211> LENGTH: 20
<212> TYPE: DNA
<213> ORGANISM: H. sapiens
<220> FEATURE:

<400> SEQUENCE: 59
ctgagattcg cccttggtgt                                              20

<210> SEQ ID NO 60
<211> LENGTH: 20
<212> TYPE: DNA
<213> ORGANISM: H. sapiens
<220> FEATURE:

<400> SEQUENCE: 60
cacgatgtcc agtgacagaa                                              20

<210> SEQ ID NO 61
<211> LENGTH: 20
<212> TYPE: DNA
<213> ORGANISM: H. sapiens
<220> FEATURE:

<400> SEQUENCE: 61
```
ttacacaacc gatccgtgtg					20

<210> SEQ ID NO 62
<211> LENGTH: 20
<212> TYPE: DNA
<213> ORGANISM: H. sapiens
<220> FEATURE:

<400> SEQUENCE: 62
ctgtcacagg aaggacatgt					20

<210> SEQ ID NO 63
<211> LENGTH: 20
<212> TYPE: DNA
<213> ORGANISM: H. sapiens
<220> FEATURE:

<400> SEQUENCE: 63
gactacatgg tcaccgccag					20

<210> SEQ ID NO 64
<211> LENGTH: 20
<212> TYPE: DNA
<213> ORGANISM: H. sapiens
<220> FEATURE:

<400> SEQUENCE: 64
gaagcatcaa cctacttaga					20

<210> SEQ ID NO 65
<211> LENGTH: 20
<212> TYPE: DNA
<213> ORGANISM: H. sapiens
<220> FEATURE:

<400> SEQUENCE: 65
agctgaaacg tgggtaagga					20

<210> SEQ ID NO 66
<211> LENGTH: 20
<212> TYPE: DNA
<213> ORGANISM: H. sapiens
<220> FEATURE:

<400> SEQUENCE: 66
tcaaacgaag acactgttcc					20

<210> SEQ ID NO 67
<211> LENGTH: 20
<212> TYPE: DNA
<213> ORGANISM: H. sapiens
<220> FEATURE:

<400> SEQUENCE: 67
agctaccagc tatgccaaac					20

<210> SEQ ID NO 68
<211> LENGTH: 20
<212> TYPE: DNA
<213> ORGANISM: H. sapiens
<220> FEATURE:

<400> SEQUENCE: 68
tgtgtataag cttttaaggt					20

```
<210> SEQ ID NO 69
<211> LENGTH: 20
<212> TYPE: DNA
<213> ORGANISM: H. sapiens
<220> FEATURE:

<400> SEQUENCE: 69
taaggtgtca tagctatgac                                               20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
ctcttactgt gctgtggaca                                               20

<210> SEQ ID NO 71
<211> LENGTH: 16
<212> TYPE: DNA
<213> ORGANISM: Artificial Sequence
<220> FEATURE:
<223> OTHER INFORMATION: PCR Primer

<400> SEQUENCE: 71
ccacagtggc cccggt                                                   16

<210> SEQ ID NO 72
<211> LENGTH: 21
<212> TYPE: DNA
<213> ORGANISM: Artificial Sequence
<220> FEATURE:
<223> OTHER INFORMATION: PCR Primer

<400> SEQUENCE: 72
acagggcttt tctcaggtgg t                                             21

<210> SEQ ID NO 73
<211> LENGTH: 28
<212> TYPE: DNA
<213> ORGANISM: Artificial Sequence
<220> FEATURE:
<223> OTHER INFORMATION: PCR Probe

<400> SEQUENCE: 73
ccaagcacag aggctccttc tgaacaag                                      28

<210> SEQ ID NO 74
<211> LENGTH: 19
<212> TYPE: DNA
<213> ORGANISM: Artificial Sequence
<220> FEATURE:
<223> OTHER INFORMATION: PCR Primer

<400> SEQUENCE: 74
gaaggtgaag gtcggagtc                                                19

<210> SEQ ID NO 75
<211> LENGTH: 20
<212> TYPE: DNA
<213> ORGANISM: Artificial Sequence
<220> FEATURE:
<223> OTHER INFORMATION: PCR Primer

<400> SEQUENCE: 75
```

```
gaagatggtg atgggatttc                                                20
```

<210> SEQ ID NO 76
<211> LENGTH: 20
<212> TYPE: DNA
<213> ORGANISM: Artificial Sequence
<220> FEATURE:
<223> OTHER INFORMATION: PCR Probe

<400> SEQUENCE: 76

```
caagcttccc gttctcagcc                                                20
```

<210> SEQ ID NO 77
<211> LENGTH: 2732
<212> TYPE: DNA
<213> ORGANISM: H. sapiens

<400> SEQUENCE: 77

```
aacaacatcc tgggattggg acccactttc tgggcactgc tggccagtcc caaaatggaa    60
cataaggaag tggttcttct acttcttta tttctgaaat caggtcaagg agagcctctg   120
gatgactatg tgaataccca gggggcttca ctgttcagtg tcactaagaa gcagctggga   180
gcaggaagta tagaagaatg tgcagcaaaa tgtgaggagg acgaagaatt cacctgcagg   240
gcattccaat atcacagtaa agagcaacaa tgtgtgataa tggctgaaaa caggaagtcc   300
tccataatca ttaggatgag agatgtagtt ttatttgaaa agaaagtgta tctctcagag   360
tgcaagactg ggaatggaaa gaactacaga gggacgatgt ccaaaacaaa aaatggcatc   420
acctgtcaaa aatggagttc cacttctccc cacagaccta gattctcacc tgctacacac   480
ccctcagagg gactggagga gaactactgc aggaatccag acaacgatcc gcaggggccc   540
tggtgctata ctactgatcc agaaaagaga tatgactact gcgacattct tgagtgtgaa   600
gaggaatgta tgcattgcag tggagaaaac tatgacggca aaatttccaa gaccatgtct   660
ggactggaat gccaggcctg ggactctcag agcccacacg ctcatggata cattccttcc   720
aaatttccaa acaagaacct gaagaagaat tactgtcgta accccgatag ggagctgcgg   780
ccttggtgtt tcaccaccga ccccaacaag cgctgggaac tttgcgacat cccccgctgc   840
acaacacctc caccatcttc tggtcccacc taccagtgtc tgaagggaac aggtgaaaac   900
tatcgcggga atgtggctgt taccgttttcc gggcacacct gtcagcactg gagtgcacag   960
accccctcaca cacataacag gacaccagaa aacttcccct gcaaaaattt ggatgaaaac  1020
tactgccgca atcctgacgg aaaaagggcc ccatggtgcc atacaaccaa cagccaagtg  1080
cggtgggagt actgtaagat accgtcctgt gactcctccc cagtatccac ggaacaattg  1140
gctcccacag caccacctga ctaaccccct gtggtccagg actgctacca tggtgatgga  1200
cagagctacc gaggcacatc ctccaccacc accacaggaa agaagtgtca gtcttggtca  1260
tctatgacac cacccggca ccagaagacc ccagaaaact acccaaatgc tggcctgaca  1320
atgaactact gcaggaatcc agatgccgat aaaggcccct ggtgttttac cacagacccc  1380
agcgtcaggt gggagtactg caacctgaaa aaatgctcag gaacagaagc gagtgttgta  1440
gcacctccgc ctgttgtcct gcttccagat gtagagactc cttccgaaga agactgtatg  1500
tttgggaatg gaaaggata ccgaggcaag agggcgacca ctgttactgg gacgccatgc  1560
caggactggg ctgcccagga gccccataga cacagcattt tcactccaga gacaaatcca  1620
cgggcgggtc tggaaaaaaa ttactgccgt aaccctgatg gtgatgtagg tggtccctgg  1680
tgctacacga caaatccaag aaaactttac gactactgtg atgtccctca gtgtgcggcc  1740
```

```
ccttcatttg attgtgggaa gcctcaagtg gagccgaaga aatgtcctgg aagggttgtg    1800
ggggggtgtg tggcccaccc acattcctgg ccctggcaag tcagtcttag aacaaggttt    1860
ggaatgcact tctgtggagg caccttgata tccccagagt gggtgttgac tgctgcccac    1920
tgcttggaga agtccccaag gccttcatcc tacaaggtca tcctgggtgc acaccaagaa    1980
gtgaatctcg aaccgcatgt tcaggaaata gaagtgtcta ggctgttctt ggagcccaca    2040
cgaaaagata ttgccttgct aaagctaagc agtcctgccg tcatcactga caaagtaatc    2100
ccagcttgtc tgccatcccc aaattatgtg gtcgctgacc ggaccgaatg tttcatcact    2160
ggctggggag aaacccaagg tactttggga gctggccttc tcaaggaagc ccagctccct    2220
gtgattgaga ataaagtgtg caatcgctat gagtttctga atggaagagt ccaatccacc    2280
gaactctgtg ctgggcattt ggccggaggc actgacagtt gccagggtga cagtggaggt    2340
cctctggttt gcttcgagaa ggacaaatac attttacaag gagtcacttc ttggggtctt    2400
ggctgtgcac gccccaataa gcctggtgtc tatgttcgtg tttcaaggtt tgttacttgg    2460
attgagggag tgatgagaaa taattaattg gacgggagac agagtgacgc actgactcac    2520
ctagaggctg ggacgtgggt agggatttag catgctggaa ataactggca gtaatcaaac    2580
gaagacactg tccccagcta ccagctacgc caaacctcgg catttttgt gttattttct     2640 gactgctgga ttctgtagta aggtgacata gctatgacat ttgttaaaaa taaactctgt    2700
acttaacttt gatttgagta aattttggtt tt                                  2732

<210> SEQ ID NO 78
<211> LENGTH: 21
<212> TYPE: DNA
<213> ORGANISM: Artificial Sequence
<220> FEATURE:
<223> OTHER INFORMATION: PCR Primer

<400> SEQUENCE: 78
cgctgggaac tttgtgacat c                                                21

<210> SEQ ID NO 79
<211> LENGTH: 22
<212> TYPE: DNA
<213> ORGANISM: Artificial Sequence
<220> FEATURE:
<223> OTHER INFORMATION: PCR Primer

<400> SEQUENCE: 79
cccgctgcac aacacctcca cc                                               22

<210> SEQ ID NO 80
<211> LENGTH: 21
<212> TYPE: DNA
<213> ORGANISM: Artificial Sequence
<220> FEATURE:
<223> OTHER INFORMATION: PCR Probe

<400> SEQUENCE: 80
cactggtagg tgggaccaga a                                                21

<210> SEQ ID NO 81
<211> LENGTH: 14121
<212> TYPE: DNA
<213> ORGANISM: H. Sapiens

<400> SEQUENCE: 81
attcccaccg ggacctgcgg ggctgagtgc ccttctcggt tgctgccgct gaggagcccg    60
```

-continued

```
cccagccagc cagggccgcg aggccgaggc caggccgcag cccaggagcc gccccaccgc    120
agctggcgat ggacccgccg aggcccgcgc tgctggcgct gctggcgctg cctgcgctgc    180
tgctgctgct gctggcgggc gccagggccg aagaggaaat gctggaaaat gtcagcctgg    240
tctgtccaaa agatgcgacc cgattcaagc acctccggaa gtacacatac aactatgagg    300
ctgagagttc cagtggagtc cctgggactg ctgattcaag aagtgccacc aggatcaact    360
gcaaggttga gctggaggtt ccccagctct gcagcttcat cctgaagacc agccagtgca    420
ccctgaaaga ggtgtatggc ttcaaccctg agggcaaagc cttgctgaag aaaaccaaga    480
actctgagga gtttgctgca gccatgtcca ggtatgagct caagctggcc attccagaag    540
ggaagcaggt tttcctttac ccggagaaag atgaacctac ttacatcctg aacatcaaga    600
ggggcatcat ttctgccctc ctggttcccc agagacaga agaagccaag caagtgttgt    660
ttctggatac cgtgtatgga aactgctcca ctcactttac cgtcaagacg aggaagggca    720
atgtggcaac agaaatatcc actgaaagag acctggggca gtgtgatcgc ttcaagccca    780
tccgcacagg catcagccca cttgctctca tcaaaggcat gacccgcccc ttgtcaactc    840
tgatcagcag cagccagtcc tgtcagtaca cactggacgc taagaggaag catgtggcag    900
aagccatctg caaggagcaa cacctcttcc tgcctttctc ctacaacaat aagtatggga    960
tggtagcaca agtgacacag actttgaaac ttgaagacac accaaagatc aacagccgct   1020
tctttggtga aggtactaag aagatgggcc tcgcatttga gagcaccaaa tccacatcac   1080
ctccaaagca ggccgaagct gttttgaaga ctctccagga actgaaaaaa ctaaccatct   1140
ctgagcaaaa tatccagaga gctaatctct tcaataagct ggttactgag ctgagaggcc   1200
tcagtgatga agcagtcaca tctctctttg cacagctgat tgaggtgtcc agccccatca   1260
ctttacaagc cttggttcag tgtggacagc ctcagtgctc cactcacatc ctccagtggc   1320
tgaaacgtgt gcatgccaac ccccttctga tagatgtggt cacctacctg gtggccctga   1380
tccccgagcc ctcagcacag cagctgcgag agatcttcaa catggcgagg gatcagcgca   1440
gccgagccac cttgtatgcg ctgagccacg cggtcaacaa ctatcataag acaaacccta   1500
cagggaccca ggagctgctg gacattgcta attacctgat ggaacagatt caagatgact   1560
gcactgggga tgaagattac acctatttga ttctgcgggt cattggaaat atgggccaaa   1620
ccatggcagc gttaactcca gaactcaagt cttcaatcct caaatgtgtc caaagtacaa   1680
agccatcact gatgatccag aaagctgcca tccaggctct gcggaaaatg agcctaaag    1740 acaaggacca ggaggttctt cttcagactt tccttgatga tgcttctccg ggagataagc   1800
gactggctgc ctatcttatg ttgatgagga gtccttcaca ggcagatatt aacaaaattg   1860
tccaaattct accatgggaa cagaatgagc aagtgaagaa ctttgtggct cccatattg    1920 ccaatatctt gaactcagaa gaattggata ccaagatct gaaaaagtta gtgaaagaag    1980
ctctgaaaga atctcaactt ccaactgtca tggacttcag aaaattctct cggaactatc   2040
aactctacaa atctgtttct cttccatcac ttgacccagc ctcagccaaa atagaaggga   2100
atcttatatt tgatccaaat aactaccttc ctaaagaaag catgctgaaa actaccctca   2160
ctgcctttgg atttgcttca gctgacctca tcgagattgg cttggaagga aaaggctttg   2220
agccaacatt ggaagctctt tttgggaagc aaggattttt cccagacagt gtcaacaaag   2280
ctttgtactg ggttaatggt caagttcctg atggtgtctc taaggtctta gtggaccact   2340
ttggctatac caaagatgat aaacatgagc aggatatggc aaatggaata atgctcagtg   2400
ttgagaagct gattaaagat ttgaaatcca aagaagtccc ggaagccaga gcctacctcc   2460
```

```
gcatcttggg agaggagctt ggttttgcca gtctccatga cctccagctc ctgggaaagc    2520
tgcttctgat gggtgcccgc actctgcagg ggatccccca gatgattgga gaggtcatca    2580
ggaagggctc aaagaatgac ttttttcttc actacatctt catggagaat gcctttgaac    2640
tccccactgg agctggatta cagttgcaaa tatcttcatc tggagtcatt gctcccggag    2700
ccaaggctgg agtaaaactg aagtagcca acatgcaggc tgaactggtg gcaaaaccct    2760
ccgtgtctgt ggagtttgtg acaaatatgg gcatcatcat tccggacttc gctaggagtg    2820
gggtccagat gaacaccaac ttcttccacg agtcgggtct ggaggctcat gttgccctaa    2880
aagctgggaa gctgaagttt atcattcctt ccccaaagag accagtcaag ctgctcagtg    2940
gaggcaacac attacatttg gtctctacca ccaaaacgga ggtgatccca cctctcattg    3000
agaacaggca gtcctggtca gtttgcaagc aagtctttcc tggcctgaat tactgcacct    3060
caggcgctta ctccaacgcc agctccacag actccgcctc ctactatccg ctgaccgggg    3120
acaccagatt agagctggaa ctgaggccta caggagagat tgagcagtat tctgtcagcg    3180
caacctatga gctccagaga gaggacagag ccttggtgga taccctgaag tttgtaactc    3240
aagcagaagg tgcgaagcag actgaggcta ccatgacatt caaatataat cggcagagta    3300
tgaccttgtc cagtgaagtc caaattccgg attttgatgt tgacctcgga acaatcctca    3360
gagttaatga tgaatctact gagggcaaaa cgtcttacag actcaccctg gacattcaga    3420
acaagaaaat tactgaggtc gccctcatgg gccacctaag ttgtgacaca aaggaagaaa    3480
gaaaaatcaa gggtgttatt tccatacccc gtttgcaagc agaagccaga agtgagatcc    3540
tcgcccactg gtcgcctgcc aaactgcttc tccaaatgga ctcatctgct acagcttatg    3600
gctccacagt ttccaagagg gtggcatggc attatgatga agagaagatt gaatttgaat    3660
ggaacacagg caccaatgta gataccaaaa aaatgacttc caatttccct gtggatctct    3720
ccgattatcc taagagcttg catatgtatg ctaatagact cctggatcac agagtccctg    3780
aaacagacat gactttccgg cacgtgggtt ccaaattaat agttgcaatg agctcatggc    3840
ttcagaaggc atctgggagt cttccttata cccagacttt gcaagaccac ctcaatagcc    3900
tgaaggagtt caacctccag aacatgggat tgccagactt ccacatccca gaaaacctct    3960
tcttaaaaag cgatggccgg gtcaaatata ccttgaacaa gaacagtttg aaaattgaga    4020
ttcctttgcc ttttggtggc aaatcctcca gagatctaaa gatgttagag actgttagga    4080
caccagccct ccacttcaag tctgtgggat tccatctgcc atctcgagag ttccaagtcc    4140
ctacttttac cattcccaag ttgtatcaac tgcaagtgcc tctcctgggt gttctagacc    4200
tctccacgaa tgtctacagc aacttgtaca actggtccgc ctcctacagt ggtggcaaca    4260
ccagcacaga ccatttcagc cttcgggctc gttaccacat gaaggctgac tctgtggttg    4320
acctgctttc ctacaatgtg caaggatctg gagaaacaac atatgaccac aagaatacgt    4380
tcacactatc atgtgatggg tctctacgcc acaaatttct agattcgaat atcaaattca    4440
gtcatgtaga aaaacttgga aacaacccag tctcaaaagg tttactaata ttcgatgcat    4500
ctagttcctg gggaccacag atgtctgctt cagttcattt ggactccaaa agaaacagc     4560 atttgtttgt caaagaagtc aagattgatg ggcagttcag agtctcttcg ttctatgcta    4620
aaggcacata tggcctgtct tgtcagaggg atcctaacac tggccggctc aatgcgagagt   4680 ccaacctgag gtttaactcc tcctacctcc aaggcaccaa ccagataaca ggaagatatg    4740
aagatggaac cctctccctc acctccacct ctgatctgca aagtggcatc attaaaaata    4800
ctgcttccct aaagtatgag aactacgagc tgactttaaa atctgacacc aatgggaagt    4860
```

```
ataagaactt tgccacttct aacaagatgg atatgacctt ctctaagcaa aatgcactgc    4920
tgcgttctga atatcaggct gattacgagt cattgaggtt cttcagcctg ctttctggat    4980
cactaaattc ccatggtctt gagttaaatg ctgacatctt aggcactgac aaaattaata    5040
gtggtgctca caaggcgaca ctaaggattg gccaagatgg aatatctacc agtgcaacga    5100
ccaacttgaa gtgtagtctc ctggtgctgg agaatgagct gaatgcagag cttggcctct    5160
ctggggcatc tatgaaatta acaacaaatg gccgcttcag ggaacacaat gcaaaattca    5220
gtctggatgg gaaagccgcc ctcacagagc tatcactggg aagtgcttat caggccatga    5280
ttctgggtgt cgacagcaaa aacattttca acttcaaggt cagtcaagaa ggacttaagc    5340
tctcaaatga catgatgggc tcatatgctg aaatgaaatt tgaccacaca aacagtctga    5400
acattgcagg cttatcactg gacttctctt caaaacttga caacatttac agctctgaca    5460
agttttataa gcaaactgtt aatttacagc tacagcccta ttctctggta actactttaa    5520
acagtgacct gaaatacaat gctctggatc tcaccaacaa tgggaaacta cggctagaac    5580
ccctgaagct gcatgtggct ggtaacctaa aaggagccta ccaaaataat gaaataaaac    5640
acatctatgc catctcttct gctgccttat cagcaagcta taaagcagac actgttgcta    5700
aggttcaggg tgtggagttt agccatcggc tcaacacaga catcgctggg ctggcttcag    5760
ccattgacat gagcacaaac tataattcag actcactgca tttcagcaat gtcttccgtt    5820
ctgtaatggc cccgtttacc atgaccatcg atgcacatac aaatggcaat gggaaactcg    5880
ctctctgggg agaacatact gggcagctgt atagcaaatt cctgttgaaa gcagaacctc    5940
tggcatttac tttctctcat gattacaaag gctccacaag tcatcatctc gtgtctagga    6000
aaagcatcag tgcagctctt gaacacaaag tcagtgccct gcttactcca gctgagcaga    6060
caggcacctg gaaactcaag acccaattta caacaatga atacagccag gacttggatg    6120
cttacaacac taaagataaa attggcgtgg agcttactgg acgaactctg gctgacctaa    6180
ctctactaga ctccccaatt aaagtgccac ttttactcag tgagcccatc aatatcattg    6240
atgctttaga gatgagagat gccgttgaga agccccaaga atttacaatt gttgcttttg    6300
taaagtatga taaaaaccaa gatgttcact ccattaacct cccatttttt gagaccttgc    6360
aagaatattt tgagaggaat cgacaaacca ttatagttgt agtggaaaac gtacagagaa    6420
acctgaagca catcaatatt gatcaatttg taagaaaata cagagcagcc ctgggaaaac    6480
tcccacagca agctaatgat tatctgaatt cattcaattg ggagagacaa gtttcacatg    6540
ccaaggagaa actgactgct ctcacaaaaa agtatagaat tacagaaaat gatatacaaa    6600
ttgcattaga tgatgccaaa atcaacttta tgaaaaaact atctcaactg cagacatata    6660
tgatacaatt tgatcagtat attaaagata gttatgattt acatgatttg aaaatagcta    6720
ttgctaatat tattgatgaa atcattgaaa aattaaaaag tcttgatgag cactatcata    6780
tccgtgtaaa tttagtaaaa acaatccatg atctacattt gtttattgaa atatttgatt    6840
ttaacaaaag tggaagtagt actgcatcct ggattcaaaa tgtggatact aagtaccaaa    6900
tcagaatcca gatacaagaa aaactgcagc agcttaagag acacatacag aatatagaca    6960
tccagcacct agctggaaag ttaaaacaac acattgaggc tattgatgtt agagtgcttt    7020
tagatcaatt gggaactaca atttcatttg aaagaataaa tgatgttctt gagcatgtca    7080
aacactttgt tataaatctt attggggatt ttgaagtagc tgagaaaatc aatgccttca    7140
gagccaaagt cctatgagtta atcgagaggt atgaagtaga ccaacaaatc caggttttaa    7200
tggataaatt agtagagttg acccaccaat acaagttgaa ggagactatt cagaagctaa    7260
```

-continued

```
gcaatgtcct acaacaagtt aagataaaag attactttga gaaattggtt ggatttattg    7320
atgatgctgt gaagaagctt aatgaattat cttttaaaac attcattgaa gatgttaaca    7380
aattccttga catgttgata aagaaattaa agtcatttga ttaccaccag tttgtagatg    7440
aaaccaatga caaaatccgt gaggtgactc agagactcaa tggtgaaatt caggctctgg    7500
aactaccaca aaaagctgaa gcattaaaac tgttttttaga ggaaaccaag gccacagttg    7560
cagtgtatct ggaaagccta caggacacca aaataacctt aatcatcaat tggttacagg    7620
aggctttaag ttcagcatct ttggctcaca tgaaggccaa attccgagag actctagaag    7680
atacacgaga ccgaatgtat caaatggaca ttcagcagga acttcaacga tacctgtctc    7740
tggtaggcca ggtttatagc acacttgtca cctacatttc tgattggtgg actcttgctg    7800
ctaagaacct tactgacttt gcagagcaat attctatcca agattgggct aaacgtatga    7860
aagcattggt agagcaaggg ttcactgttc ctgaaatcaa gaccatcctt gggaccatgc    7920
ctgcctttga agtcagtctt caggctcttc agaaagctac cttccagaca cctgattttta    7980 tagtccccct aacagatttg aggattccat cagttcagat aaacttcaaa gacttaaaaa    8040
atataaaaat cccatccagg ttttccacac cagaatttac catccttaac accttccaca    8100
ttccttcctt tacaattgac tttgtcgaaa tgaaagtaaa gatcatcaga accattgacc    8160
agatgcagaa cagtgagctg cagtggcccg ttccagatat atatctcagg gatctgaagg    8220
tggaggacat tcctctagcg agaatcaccc tgccagactt ccgtttacca gaaatcgcaa    8280
ttccagaatt cataatccca actctcaacc ttaatgattt tcaagttcct gaccttcaca    8340
taccagaatt ccagcttccc cacatctcac acacaattga agtacctact tttggcaagc    8400
tatacagtat tctgaaaatc caatctcctc ttttcacatt agatgcaaat gctgacatag    8460
ggaatggaac cacctcagca aacgaagcag gtatcgcagc ttccatcact gccaaaggag    8520
agtccaaatt agaagttctc aattttgatt ttcaagcaaa tgcacaactc tcaaacccta    8580
agattaatcc gctggctctg aaggagtcag tgaagttctc cagcaagtac ctgagaacgg    8640
agcatgggag tgaaatgctg tttttttggaa atgctattga gggaaaatca aacacagtgg    8700
caagtttaca cacagaaaaa aatacactgg agcttagtaa tggagtgatt gtcaagataa    8760
acaatcagct taccctggat agcaacacta atacttcca caaattgaac atccccaaac    8820
tggacttctc tagtcaggct gacctgcgca acgagatcaa gacactgttg aaagctggcc    8880
acatagcatg gacttcttct ggaaaagggt catggaaatg ggcctgcccc agattctcag    8940
atgagggaac acatgaatca caaattagtt tcaccataga aggacccctc acttcctttg    9000
gactgtccaa taagatcaat agcaaacacc taagagtaaa ccaaaacttg gtttatgaat    9060
ctggctccct caacttttct aaacttgaaa ttcaatcaca agtcgattcc cagcatgtgg    9120
gccacagtgt tctaactgct aaaggcatgg cactgtttgg agaagggaag gcagagttta    9180
ctgggaggca tgatgctcat ttaaatggaa aggttattgg aactttgaaa aattctcttt    9240
tcttttcagc ccagccattt gagatcacgg catccacaaa caatgaaggg aatttgaaag    9300 ttcgtttttcc attaaggtta acagggaaga tagacttcct gaataactat gcactgtttc    9360
tgagtcccag tgcccagcaa gcaagttggc aagtaagtgc taggttcaat cagtataagt    9420
acaaccaaaa tttctctgct ggaaacaacg agaacattat ggaggcccat gtaggaataa    9480
atggagaagc aaatctggat ttcttaaaca ttccttttaac aattcctgaa atgcgtctac    9540
cttacacaat aatcacaact cctccactga aagatttctc tctatgggaa aaaacaggct    9600
tgaaggaatt cttgaaaacg acaaagcaat catttgattt aagtgtaaaa gctcagtata    9660
```

```
agaaaaacaa acacaggcat tccatcacaa atcctttggc tgtgctttgt gagtttatca    9720
gtcagagcat caaatccttt gacaggcatt ttgaaaaaaa cagaaacaat gcattagatt    9780
ttgtcaccaa atcctataat gaaacaaaaa ttaagtttga taagtacaaa gctgaaaaat    9840
ctcacgacga gctccccagg accttttcaaa ttcctggata cactgttcca gttgtcaatg   9900
```

```
agaaaaacaa acacaggcat tccatcacaa atcctttggc tgtgctttgt gagtttatca    9720
gtcagagcat caaatccttt gacaggcatt ttgaaaaaaa cagaaacaat gcattagatt    9780
ttgtcaccaa atcctataat gaaacaaaaa ttaagtttga taagtacaaa gctgaaaaat    9840
ctcacgacga gctccccagg accttttcaa ttcctggata cactgttcca gttgtcaatg    9900
ttgaagtgtc tccattcacc atagagatgt cggcattcgg ctatgtgttc ccaaaagcag    9960
tcagcatgcc tagtttctcc atcctaggtt ctgacgtccg tgtgccttca tacacattaa   10020
tcctgccatc attagagctg ccagtccttc atgtccctag aaatctcaag ctttctcttc   10080
cacatttcaa ggaattgtgt accataagcc atattttat tcctgccatg gcaatatta    10140
cctatgattt ctcctttaaa tcaagtgtca tcacactgaa taccaatgct gaactttta    10200
accagtcaga tattgttgct catctccttt cttcatcttc atctgtcatt gatgcactgc   10260
agtacaaatt agagggcacc acaagattga caagaaaaag gggattgaag ttagccacag   10320
ctctgtctct gagcaacaaa tttgtggagg tagtcataa cagtactgtg agcttaacca    10380
cgaaaaatat ggaagtgtca gtggcaaaaa ccacaaaagc cgaaattcca attttgagaa   10440
tgaatttcaa gcaagaactt aatggaaata ccaagtcaaa acctactgtc tcttcctcca   10500
tggaatttaa gtatgatttc aattcttcaa tgctgtactc taccgctaaa ggagcagttg   10560
accacaagct tagcttggaa agcctcacct cttactttc cattgagtca tctaccaaag    10620
gagatgtcaa gggttcggtt cttctcggg aatattcagg aactattgct agtgaggcca    10680
acacttactt gaattccaag agcacacggt cttcagtgaa gctgcagggc acttccaaaa   10740
ttgatgatat ctggaacctt gaagtaaaag aaaattttgc tggagaagcc acactccaac   10800
gcatatattc cctctgggag cacagtacga aaaccacttt acagctagag ggcctctttt   10860
tcaccaacgg agaacataca agcaaagcca ccctggaact ctctccatgg caaatgtcag   10920
ctcttgttca ggtccatgca agtcagccca gttccttcca tgatttccct gaccttggcc   10980
aggaagtggc cctgaatgct aacactaaga accagaagat cagatggaaa aatgaagtcc   11040
ggattcattc tgggtctttc cagagccagg tcgagctttc caatgaccaa gaaaaggcac   11100
accttgacat tgcaggatcc ttagaaggac acctaaggtt cctcaaaaat atcatcctac   11160
cagtctatga caagagctta tgggattcc taaagctgga tgtaaccacc agcattggta   11220
ggagacagca tcttcgtgtt tcaactgcct ttgtgtacac caaaaacccc aatggctatt   11280
cattctccat ccctgtaaaa gttttggctg ataaattcat tactcctggg ctgaaactaa   11340
atgatctaaa ttcagttctt gtcatgccta cgttccatgt cccatttaca gatcttcagg   11400
ttccatcgtg caaacttgac ttcagagaaa tacaaatcta taagaagctg agaacttcat   11460
catttgccct caacctacca acactccccg aggtaaaatt ccctgaagtt gatgtgttaa   11520
caaaatattc tcaaccagaa gactccttga ttcccttttt tgagataacc gtgcctgaat   11580
ctcagttaac tgtgtcccag ttcacgcttc caaaaagtgt ttcagatggc attgctgctt   11640
tggatctaaa tgcagtagcc aacaagatcg cagactttga gttgcccacc atcatcgtgc   11700
ctgagcagac cattgagatt ccctccatta agttctctgt acctgctgga attgtcattc   11760
cttcctttca agcactgact gcacgctttg aggtagactc tcccgtgtat aatgccactt   11820
ggagtgccag tttgaaaaac aaagcagatt atgttgaaac agtcctggat tccacatgca   11880
gctcaaccgt acagttccta gaatatgaac taaatgtttt gggaacacac aaaatcgaag   11940
atggtacgtt agcctctaag actaaaggaa cacttgcaca ccgtgacttc agtgcagaat   12000
atgaagaaga tggcaaattt gaaggacttc aggaatggga aggaaaagcg caccctcaata  12060
```

-continued

```
tcaaaagccc agcgttcacc gatctccatc tgcgctacca gaaagacaag aaaggcatct    12120
ccacctcagc agcctcccca gccgtaggca ccgtgggcat ggatatggat gaagatgacg    12180
acttttctaa atggaacttc tactacagcc ctcagtcctc tccagataaa aaactcacca    12240
tattcaaaac tgagttgagg gtccgggaat ctgatgagga aactcagatc aaagttaatt    12300
gggaagaaga ggcagcttct ggcttgctaa cctctctgaa agacaacgtg cccaaggcca    12360
caggggtcct ttatgattat gtcaacaagt accactggga acacacaggg ctcaccctga    12420
gagaagtgtc ttcaaagctg agaagaaatc tgcagaacaa tgctgagtgg gtttatcaag    12480
gggccattag gcaaattgat gatatcgacg tgaggttcca gaaagcagcc agtggcacca    12540
ctgggaccta ccaagagtgg aaggacaagg cccagaatct gtaccaggaa ctgttgactc    12600
aggaaggcca agccagtttc cagggactca aggataacgt gtttgatggc ttggtacgag    12660
ttactcaaaa attccatatg aaagtcaagc atctgattga ctcactcatt gattttctga    12720
acttccccag attccagttt ccggggaaac ctgggatata cactagggag gaactttgca    12780
ctatgttcat aagggaggta gggacggtac tgtcccaggt atattcgaaa gtccataatg    12840
gttcagaaat actgttttcc tatttccaag acctagtgat tacacttcct ttcgagttaa    12900
ggaaacataa actaatagat gtaatctcga tgtataggga actgttgaaa gatttatcaa    12960
aagaagccca agaggtattt aaagccattc agtctctcaa gaccacagag gtgctacgta    13020
atcttcagga cctttacaa ttcatttttcc aactaataga agataacatt aaacagctga    13080
aagagatgaa atttacttat cttattaatt atatccaaga tgagatcaac acaatcttca    13140
atgattatat cccatatgtt tttaaattgt tgaaagaaaa cctatgcctt aatcttcata    13200
agttcaatga atttattcaa aacgagcttc aggaagcttc tcaagagtta cagcagatcc    13260
atcaatacat tatggcccctt cgtgaagaat attttgatcc aagtatagtt ggctggacag    13320
tgaaatatta tgaacttgaa gaaaagatag tcagtctgat caagaacctg ttagttgctc    13380
ttaaggactt ccattctgaa tatattgtca gtgcctctaa ctttacttcc caactctcaa    13440
gtcaagttga gcaatttctg cacagaaata ttcaggaata tcttagcatc cttaccgatc    13500
cagatggaaa agggaaagag aagattgcag agctttctgc cactgctcag gaaataatta    13560
aaagccaggc cattgcgacg aagaaaataa tttctgatta ccaccagcag tttagatata    13620
aactgcaaga ttttttcagac caactctctg attactatga aaaatttatt gctgaatcca    13680
aaagattgat tgacctgtcc attcaaaact accacacatt tctgatatac atcacggagt    13740
tactgaaaaa gctgcaatca accacagtca tgaaccccta catgaagctt gctccaggag    13800
aacttactat catcctctaa ttttttaaaa gaaatcttca tttattcttc ttttccaatt    13860
gaactttcac atagcacaga aaaaattcaa actgcctata ttgataaaac catacagtga    13920
gccagccttg cagtaggcag tagactataa gcagaagcac atatgaactg gacctgcacc    13980
aaagctggca ccagggctcg gaaggtctct gaactcagaa ggatggcatt ttttgcaagt    14040
taaagaaaat caggatctga gttatttgc taaacttggg ggaggaggaa caaataaatg    14100
gagtctttat tgtgtatcat a                                              14121
```

<210> SEQ ID NO 82
<211> LENGTH: 21
<212> TYPE: DNA
<213> ORGANISM: Artificial Sequence
<220> FEATURE:
<223> OTHER INFORMATION: PCR Primer

<400> SEQUENCE: 82

```
tgctaaaggc acatatggcc t                                              21

<210> SEQ ID NO 83
<211> LENGTH: 23
<212> TYPE: DNA
<213> ORGANISM: Artificial Sequence
<220> FEATURE:
<223> OTHER INFORMATION: PCR Primer

<400> SEQUENCE: 83
ctcaggttgg actctccatt gag                                            23

<210> SEQ ID NO 84
<211> LENGTH: 28
<212> TYPE: DNA
<213> ORGANISM: Artificial Sequence
<220> FEATURE:
<223> OTHER INFORMATION: PCR Probe

<400> SEQUENCE: 84
cttgtcagag ggatcctaac actggccg                                       28

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
cagtgtccag aaagtgtgtc                                                20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
ggtttgctca gttggtgctg                                                20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
ttaccatggt agcactgccg                                                20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
actctggcca ttaccatggt                                                20

<210> SEQ ID NO 89
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 89
tgtgacagtg gtggagaatg                                                20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
tgacagtcgg aggagcgacc                                                20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
tgcccattta tttgtccctg                                                20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
agttttcttg gattcattgt                                                20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
gagagggata tcacagtagt                                                20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
cagtcctggc ggtgaccatg                                                20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
cttatagtga ttgcacactt                                                20

<210> SEQ ID NO 96

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
tctggccaaa tgctcagcac                                                   20

<210> SEQ ID NO 97
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 97
cgagaggcgg acgggaccg                                                    19

<210> SEQ ID NO 98
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 98
cgagaggcgg acgggaccgt t                                                 21

<210> SEQ ID NO 99
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 99
ttgctctccg cctgccctgg c                                                 21

<210> SEQ ID NO 100
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 100
gctctccgcc tgccctggc                                                    19
```

MODULATION OF APOLIPOPROTEIN (A) EXPRESSION

RELATED APPLICATIONS

This application is a Continuation of U.S. patent application Ser. No. 10/559,647, filed Jul. 31, 2006, which is a US National Phase Application under 35 USC 371 of PCT/US2004/014540 filed on Jun. 2, 2004, which claims priority to U.S. provisional patent application No. 60/475,402, filed Jun. 2, 2003 and U.S. patent application Ser. No. 10/684,440, filed Oct. 15, 2003, each of which is incorporated by reference in its entirety.

SEQUENCE LISTING

The present application is being filed along with a Sequence Listing in electronic format. The Sequence Listing is provided as a file entitled ISPH0595USD1 SEQ.txt, created on Aug. 6, 2007 which is 64 Kb in size. The information in the electronic format of the sequence listing is incorporated herein by reference in its entirety.

BACKGROUND OF THE INVENTION

The present invention provides compositions and methods for modulating the expression of apolipoprotein(a).

Lipoproteins are globular, micelle-like particles that consist of a non-polar core of acylglycerols and cholesteryl esters, surrounded by an amphiphilic coating consisting of protein, phospholipid and cholesterol. Lipoproteins have been classified into five broad categories on the basis of their functional and physical properties: chylomicrons (which transport dietary lipids from intestine to tissues), very low density lipoproteins (VLDL), intermediate density lipoproteins (IDL). Low density lipoproteins (LDL), (all of which transport triacylglycerols and cholesterol from the liver to tissues), and high density lipoproteins (HDL) (which transport endogenous cholesterol from tissues to the liver). Lipoprotein particles undergo continuous metabolic processing and have variable properties and compositions. Lipoprotein densities increase without decreasing particle diameter because the density of their outer coatings is less than that of the inner core. The protein components of lipoproteins are known as apolipoproteins. At least nine apolipoproteins are distributed in significant amounts among the various human lipoproteins.

Lipoprotein (a) (also known as Lp(a)) is a cholesterol rich particle of the pro-atherogenic LDL class. Since Lp(a) is found only in Old World primates and European hedgehogs, it has been suggested that it does not play an essential role in lipid and lipoprotein metabolism. Most studies have shown that high concentrations of Lp(a) are strongly associated with increased risk of cardiovascular disease (Rainwater and Kammerer, *J. Exp. Zool.*, 1998, 282, 54-61). These observations have stimulated numerous studies in humans and other primates to investigate the factors that control Lp(a) concentrations and physiological properties (Rainwater and Kammerer, *J. Exp. Zool.*, 1998, 282, 54-61).

Lp(a) contains two disulfide-linked distinct proteins, apolipoprotein(a) (or ApoA) and apolipoprotein B (or ApoB) (Rainwater and Kammerer, *J. Exp. Zool.*, 1998, 282, 54-61). Apolipoprotein(a) is a unique apolipoprotein encoded by the LPA gene which has been shown to exclusively control the physiological concentrations of Lp(a) (Rainwater and Kammerer, *J. Exp. Zool.*, 1998, 282, 54-61). It varies in size due to interallelic differences in the number of tandemly repeated Kringle-4-encoding 5.5 kb sequences in the LPA gene (Rainwater and Kammerer, *J. Exp. Zool.*, 1998, 282, 54-61).

Cloning of human apolipoprotein(a) in 1987 revealed homology to human plasminogen (McLean et al., *Nature*, 1987, 330, 132-137). The gene locus LPA encoding apolipoprotein(a) was localized to chromosome 6q26-27, in close proximity to the homologous gene for plasminogen (Frank et al., *Hum. Genet.*, 1988, 79, 352-356).

Transgenic mice expressing human apolipoprotein(a) were found to be more susceptible than control mice to the development of lipid-staining lesions in the aorta. Consequently, apolipoprotein(a) is co-localized with lipid deposition in the artery walls (Lawn et al., *Nature*, 1992, 360, 670-672). As an extension of these studies, it was established that the major in vivo action of apolipoprotein(a) is inhibition of the conversion of plasminogen to plasmin which causes decreased activation of latent transforming growth factor-beta. Since transforming growth factor-beta is a negative regulator of smooth muscle cell migration and proliferation, inhibition of plasminogen activation indicates a possible mechanism for apolipoprotein(a) induction of atherosclerotic lesions (Grainger et al., *Nature*, 1994, 370, 460-462).

Elevated plasma levels of Lp(a), caused by increased expression of apolipoprotein(a), are associated with increased risk for atherosclerosis and its manifestations, which include hypercholesterolemia (Seed et al., *N. Engl. J. Med.*, 1990, 322, 1494-1499), myocardial infarction (Sandkamp et al., *Clin. Chem.*, 1990, 36, 20-23), and thrombosis (Nowak-Gottl et al., *Pediatrics*, 1997, 99, E11).

Moreover, the plasma concentration of Lp(a) is strongly influenced by heritable factors and is refractory to most drug and dietary manipulation (Katan and Beynen, *Am. J. Epidemiol.*, 1987, 125, 387-399; Vessby et al., *Atherosclerosis*, 1982, 44, 61-71.).

Pharmacologic therapy of elevated Lp(a) levels has been only moderately successful and apheresis remains the most effective therapeutic modality (Hajjar and Nachman, *Annu. Rev. Med.*, 1996, 47, 423-442).

Morishita et al. reported the use of three ribozyme oligonucleotides against apolipoprotein(a) for inhibition of apolipoprotein(a) expression in HepG2 cells (Morishita et al., *Circulation*, 1998, 98, 1898-1904).

U.S. Pat. No. 5,721,138 refers to nucleotide sequences encoding the human apolipoprotein(a) gene 5'-regulatory region and isolated nucleotide sequences comprising at least thirty consecutive complementary nucleotides from human apolipoprotein(a) from nucleotide positions 208 to 1448 (Lawn, 1998).

To date, investigative and therapeutic strategies aimed at inhibiting apolipoprotein(a) function have involved the previously cited use of Lp(a) apheresis and ribozyme oligonucleotides. No existing drugs are available to specifically lower lipoprotein(a) levels in humans, and only limited models exist in which to perform drug discovery. Consequently, there remains a long-felt need for additional agents and methods capable of effectively modulating, e.g., inhibiting, apolipoprotein(a) function, and particularly a need for agents capable of safe and efficacious administration to lower alipoprotein(a) levels in patients at risk for the development of coronary artery disease.

SUMMARY OF THE INVENTION

The present invention provides compositions and methods for modulating the expression of apolipoprotein(a). Such novel compositions and methods enable research into the pathways of plasminogen and apolipoprotein(a), as well as other lipid metabolic processes. Such novel compositions and methods are useful in assessing the toxicity of chemical and pharmaceutical compounds on apolipoprotein(a) function, plasminogen or other lipid metabolic processes. Such novel compositions and methods are useful for drug discovery and for the treatment of cardiovascular conditions, including myocardial infarction and atherosclerosis, among others.

Antisense technology is emerging as an effective means for reducing the expression of specific gene products, and is uniquely useful in a number of therapeutic, diagnostic, and research applications for the modulation of apolipoprotein(a) expression.

In particular, this invention relates to compounds, particularly oligonucleotide compounds, which, in preferred embodiments, hybridize with nucleic acid molecules or sequences encoding apolipoprotein(a). Such compounds are shown herein to modulate the expression of apolipoprotein (a). Additionally disclosed are embodiments of oligonucleotide compounds that hybridize with nucleic acid molecules encoding apolipoprotein(a) in preference to nucleic acid molecules or sequences encoding plasminogen.

The present invention is directed to compounds, especially nucleic acid and nucleic acid-like oligomers, which are targeted to a nucleic acid encoding apolipoprotein(a), and which modulate the expression of apolipoprotein(a). Pharmaceutical and other compositions comprising the compounds of the invention are also provided.

Further provided are methods of screening for modulators of apolipoprotein(a) and methods of modulating the expression of apolipoprotein(a) in cells, tissues or animals comprising contacting said cells, tissues or animals with one or more of the compounds or compositions of the invention. In these methods, the cells or tissues may be contacted in vivo. Alternatively, the cells or tissues may be contacted ex vivo.

Methods of treating an animal, particularly a human, having, suspected of having, or being prone to a disease or condition associated with expression of apolipoprotein(a) are also set forth herein. Such methods comprise administering a therapeutically or prophylactically effective amount of one or more of the compounds or compositions of the invention to the person in need of treatment.

In one aspect, the invention provides the use of a compound or composition of the invention in the manufacture of a medicament for the treatment of any and all conditions disclosed herein.

DETAILED DESCRIPTION OF THE INVENTION

A. Overview of the Invention

The present invention employs compounds, preferably oligonucleotides and similar species, for use in modulating the function or effect of nucleic acid molecules encoding apolipoprotein(a). This is accomplished by providing oligonucleotides that specifically hybridize with one or more nucleic acid molecules encoding apolipoprotein(a). As used herein, the terms "target nucleic acid" and "nucleic acid molecule encoding apolipoprotein(a)" have been used for convenience to encompass DNA encoding apolipoprotein(a), RNA (including pre-mRNA and mRNA or portions thereof) transcribed from such DNA, and also cDNA derived from such RNA. The hybridization of a compound of this invention with its target nucleic acid is generally referred to as "antisense". Antisense technology is emerging as an effective means of reducing the expression of specific gene products and is uniquely useful in a number of therapeutic, diagnostic and research applications involving modulation of apolipoprotein (a) expression.

Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments, such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA, which may be engaged in or facilitated by the RNA. One preferred result of such interference with target nucleic acid function is modulation of the expression of apolipoprotein(a). In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases that pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired. Such conditions include, e.g., physiological conditions in the case of in vivo assays or therapeutic treatment, and conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances. In the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound) is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position.

The oligonucleotide and the further DNA, RNA, or oligonucleotide molecule are complementary to each other when a sufficient number of complementary positions in each molecule are occupied by nucleobases that can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

The sequence of an antisense compound can be, but need not necessarily be, 100% complementary to that of its target nucleic acid to be specifically hybridizable. Moreover, an oligonucleotide may hybridize over one or more segments such that intervening or adjacent segments are not involved in the hybridization event. In one embodiment of this invention, the antisense compounds of the present invention comprise at least 70%, or at least 75%, or at least 80%, or at least 85% sequence complementarity to a target region within the target nucleic acid. In other embodiments, the antisense compounds of the present invention comprise at least 90% sequence complementarity and even comprise at least 95% or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases, and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.,* 1990, 215, 403-410; Zhang and Madden, *Genome Res.,* 1997, 7, 649-656).

Percent homology, sequence identity, or complementarity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.,* 1981, 2, 482-489). In some embodiments, homology, sequence identity, or complementarity between the oligomeric and target is between about 50% to about 60%. In some embodiments, homology, sequence identity, or complementarity is between about 60% to about 70%. In other embodiments, homology, sequence identity, or complementarity is between about 70% and about 80%. In still other embodiments, homology, sequence identity, or complementarity is between about 80% and about 90%. In yet other embodiments, homology, sequence identity, or complementarity is about 90%, about 92%, about 94%, about 95%, about 96%, about 97%, about 98%, about 99%, or about 100%.

B. Compounds of the Invention

According to the present invention, "compounds" include antisense oligomeric compounds, antisense oligonucleotides, siRNAs, external guide sequence (EGS) oligonucleotides, alternate splicers, and other oligomeric compounds that hybridize to at least a portion of the target nucleic acid. As such, these compounds may be introduced in the form of single-stranded, double-stranded, partially single-stranded, or circular oligomeric compounds. Specifically excluded from the definition of "compounds" herein are ribozymes that contain internal or external "bulges" that do not hybridize to the target sequence. Once introduced to a system, the compounds of the invention may elicit the action of one or more enzymes or structural proteins to effect modification of the target nucleic acid.

One non-limiting example of such an enzyme is RNase H, a cellular endonuclease which cleaves the RNA strand of an RNA:DNA duplex. It is known in the art that single-stranded antisense compounds that are "DNA-like" elicit RNase H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell,* 1995, 81, 611-620). The primary interference effects of dsRNA are posttranscriptional (Montgomery et al., *Proc. Natl. Acad. Sci. USA,* 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature,* 1998, 391, 806-811). Recently, the single-stranded RNA oligomers of antisense polarity of the dsRNAs have been reported to be the potent inducers of RNAi (Tijsterman et al., *Science,* 2002, 295, 694-697).

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA), or mimetics, chimeras, analogs and homologs thereof. This term includes oligonucleotides composed of naturally occurring nucleobases, sugars, and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid, and increased stability in the presence of nucleases.

The oligonucleotides of the present invention also include modified oligonucleotides in which a different base is present at one or more of the nucleotide positions in the oligonucleotide. For example, if the first nucleotide is an adenosine, modified oligonucleotides may be produced that contain thymidine, guanosine or cytidine at this position. This may be done at any of the positions of the oligonucleotide. These oligonucleotides are then tested using the methods described herein to determine their ability to inhibit expression of apolipoprotein(a) mRNA.

While oligonucleotides are a preferred form of the compounds of this invention, the present invention comprehends other families of compounds as well, including but not limited to, oligonucleotide analogs and mimetics such as those described herein.

The compounds in accordance with this invention comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one embodiment, the compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another embodiment, the compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

In another embodiment, compounds of this invention are oligonucleotides from about 12 to about 50 nucleobases. In another embodiment, compounds of this invention comprise from about 15 to about 30 nucleobases.

In another embodiment, the antisense compounds comprise at least 8 contiguous nucleobases of an antisense compound disclosed herein.

Antisense compounds 8-80 nucleobases in length comprising a stretch of at least eight (8) consecutive nucleobases selected from within the illustrative antisense compounds are considered to be suitable antisense compounds as well.

Exemplary compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound that is specifically hybridizable to the target nucleic acid, and continuing until the oligonucleotide contains about 8 to about 80 nucleobases). Similarly, exemplary antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound that is specifically hybridizable to the target nucleic acid and continuing until the oligonucleotide contains about 8 to about 80 nucleobases).

Exemplary compounds of this invention may be found identified in the Examples and listed in Tables 1 and 7. In addition to oligonucleotide compounds that bind to target sequences of apolipoprotein(a) in general, there are also exemplified oligonucleotide compounds of this invention that bind to target nucleotide sequences of apolipoprotein(a), but do not bind to, or do not bind preferentially to, sequences of plasminogen due to lack of homology between the two nucleic acid molecules or a sufficient number of mismatches in the target sequences. These latter compounds are also useful in various therapeutic methods of this invention.

Examples of antisense compounds to such 'mismatched' target sequences as described above include SEQ ID NO: 12 and SEQ ID NO: 23 of Table 1 below. See, also, the discussion of target regions below.

One having skill in the art armed with the exemplary antisense compounds illustrated herein will be able, without undue experimentation, to identify further useful antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes apolipoprotein(a).

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes having translation initiation codons with the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding apolipoprotein(a), regardless of the sequence(s) of such codons. A translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Another target region includes the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. Another target region for this invention is the 5' cap region.

Accordingly, the present invention provides antisense compounds that target a portion of nucleotides 1-2480 as set forth in SEQ ID NO: 4. In another embodiment, the antisense compounds target at least an 8-nucleobase portion of nucleotides 1-45, comprising the 5'UTR as set forth in SEQ ID NO: 4. In another embodiment, the antisense compounds target at least an 8-nucleobase portion of nucleotides 13593-13938, comprising the 3'UTR as set forth in SEQ ID NO: 4. In another embodiment, the antisense compounds target at least an 8-nucleobase portion of nucleotides 46-13592, comprising the coding region as set forth in SEQ ID NO: 4. In still other embodiments, the antisense compounds target at least an 8-nucleobase portion of a "preferred target segment" (as defined herein) as set forth in Table 2.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the sites where exons are joined. Targeting exon-exon junctions can be useful in situations where the overproduction of a normal splice product is implicated in disease, or where the overproduction of an aberrant splice product is implicated in disease. In one embodiment, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources known as "fusion transcripts" are also suitable target sites. Introns can be effectively targeted using antisense compounds targeted to, for example, DNA or pre-mRNA.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants, and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid that are accessible for hybridization.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). One having skill in the art armed with the target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

In various embodiments of this invention, the oligomeric compounds are targeted to regions of a target apolipoprotein (a) nucleobase sequence, such as those disclosed herein. All regions of the target nucleobase sequence to which an oligomeric antisense compound can be targeted, wherein the regions are greater than or equal to 8 and less than or equal to 80 nucleobases, are described as follows:

Let R(m, n+m−1) be a region from a target nucleobase sequence, where "n" is the 5'-most nucleobase position of the region, where "n+m−1" is the 3'-most nucleobase position of the region and where "m" is the length of the region. A set "S(m)", of regions of length "m" is defined as the regions where n ranges from 1 to L−m+1, where L is the length of the target nucleobase sequence and L>m. A set, "A", of all regions can be constructed as a union of the sets of regions for each length from where m is greater than or equal to 8 and is less than or equal to 80.

This set of regions can be represented using the following mathematical notation:

$$A = \bigcup_m S(m)$$

where m∈N|8≤m≤80
and $$S(m)=\{R_{n,n+m-1}|n \in \{1, 2, 3, \ldots, L-m+1\}\}$$

where the mathematical operator | indicates "such that",
where the mathematical operator ∈ indicates "a member of a set" (e.g. y ∈ Z indicates that element y is a member of set Z),
where x is a variable,
where N indicates all natural numbers, defined as positive integers,
and where the mathematical operator ∪ indicates "the union of sets".

For example, the set of regions for m equal to 8, 9 and 80 can be constructed in the following manner. The set of regions, each 8 nucleobases in length, S(m=8), in a target nucleobase sequence 100 nucleobases in length (L=100), beginning at position 1 (n=1) of the target nucleobase sequence, can be created using the following expression:

$$S(8)=\{R_{1,8}|n \in \{1, 2, 3, \ldots, 93\}\}$$

and describes the set of regions comprising nucleobases 1-8, 2-9, 3-10, 4-11, 5-12, 6-13, 7-14, 8-15, 9-16, 10-17, 11-18, 12-19, 13-20, 14-21, 15-22, 16-23, 17-24, 18-25, 19-26, 20-27, 21-28, 22-29, 23-30, 24-31, 25-32, 26-33, 27-34, 28-35, 29-36, 30-37, 31-38, 32-39, 33-40, 34-41, 35-42, 36-43, 37-44, 38-45, 39-46, 40-47, 41-48, 42-49, 43-50, 44-51, 45-52, 46-53, 47-54, 48-55, 49-56, 50-57, 51-58, 52-59, 53-60, 54-61, 55-62, 56-63, 57-64, 58-65, 59-66, 60-67, 61-68, 62-69, 63-70, 64-71, 65-72, 66-73, 67-74, 68-75, 69-76, 70-77, 71-78, 72-79, 73-80, 74-81, 75-82, 76-83, 77-84, 78-85, 79-86, 80-87, 81-88, 82-89, 83-90, 84-91, 85-92, 86-93, 87-94, 88-95, 89-96, 90-97, 91-98, 92-99, 93-100.

An additional set for regions 20 nucleobases in length, in a target sequence 100 nucleobases in length, beginning at position 1 of the target nucleobase sequence, can be described using the following expression:

$$S(20)=\{R_{1,20}|n \in \{1, 2, 3, \ldots, 81\}\}$$

and describes the set of regions comprising nucleobases 1-20, 2-21, 3-22, 4-23, 5-24, 6-25, 7-26, 8-27, 9-28, 10-29, 11-30, 12-31, 13-32, 14-33, 15-34, 16-35, 17-36, 18-37, 19-38, 20-39, 21-40, 22-41, 23-42, 24-43, 25-44, 26-45, 27-46, 28-47, 29-48, 30-49, 31-50, 32-51, 33-52, 34-53, 35-54, 36-55, 37-56, 38-57, 39-58, 40-59, 41-60, 42-61, 43-62, 44-63, 45-64, 46-65, 47-66, 48-67, 49-68, 50-69, 51-70, 52-71, 53-72, 54-73, 55-74, 56-75, 57-76, 58-77, 59-78, 60-79, 61-80, 62-81, 63-82, 64-83, 65-84, 66-85, 67-86, 68-87, 69-88, 70-89, 71-90, 72-91, 73-92, 74-93, 75-94, 76-95, 77-96, 78-97, 79-98, 80-99, 81-100.

An additional set for regions 80 nucleobases in length, in a target sequence 100 nucleobases in length, beginning at position 1 of the target nucleobase sequence, can be described using the following expression:

$$S(80)=\{R_{1,80}|n \in \{1, 2, 3, \ldots, 21\}\}$$

and describes the set of regions comprising nucleobases 1-80, 2-81, 3-82, 4-83, 5-84, 6-85, 7-86, 8-87, 9-88, 10-89, 11-90, 12-91, 13-92, 14-93, 15-94, 16-95, 17-96, 18-97, 19-98, 20-99, 21-100.

Thus, in this example, A would include regions 1-8, 2-9, 3-10 . . . 93-100, 1-20, 2-21, 3-22 . . . 81-100, 1-80, 2-81, 3-82 . . . 21-100.

The union of these aforementioned example sets and other sets for lengths from 10 to 19 and 21 to 79 can be described using the mathematical expression:

$$A = \bigcup_m S(m)$$

where ∪ represents the union of the sets obtained by combining all members of all sets.

The mathematical expressions described herein define all possible target regions in a target nucleobase sequence of any length L, where the region is of length m, and where m is greater than or equal to 8 and less than or equal to 80 nucleobases, and where m is less than L, and where n is less than L−m+1.

In one embodiment, the oligonucleotide compounds of this invention are 100% complementary to these sequences or to small sequences found within each of the above listed sequences. In another embodiment the oligonucleotide compounds have from at least 3 or 5 mismatches per 20 consecutive nucleobases in individual nucleobase positions to these target regions. Still other compounds of the invention are targeted to overlapping regions of the above-identified portions of the apolipoprotein(a) sequence.

In still another embodiment, target regions include those portions of the apolipoprotion(a) sequence that do not overlap with plasminogen sequences. For example, among such apolipoprotein(a) target sequences are included those found within the following nucleobase sequences: 10624-10702, 10963-11036, 11325-11354, 11615-11716, 11985-12038, 12319-12379, 13487-13491, and 13833-13871. As a further example, target sequences of apolipoprotein(a) that have at least 6 mismatches with the sequence of plasminogen over at least 20 consecutive nucleotides are desirable targets for antisense compounds that bind preferentially to apolipoprotein (a) rather than to plasminogen. Such target sequences can readily be identified by a BLAST comparison of the two GENBANK® sequences of plasminogen (e.g., GENBANK® Accession No. NM_000301) and apolipoprotein(a) (e.g., GENBANK® Accession No. NM_005577.1).

In still another embodiment, the target regions include portions of the apolipoprotein (a) sequence that overlap with portions of the plasminogen or apolipoprotein B sequence, but to which antisense compounds bind to inhibit apolipoprotein (a) but do not inhibit, to any appreciable degree, plasminogen and/or apolipoprotein B. Such targets may be obtained from the target regions of SEQ ID NOs: 46, 54, 56, 57, 59, 60, 61, 62, 64, 67, 68 and 69 of Table 2. These target regions are bound by antisense oligonucleotides of SEQ ID Nos: 11, 23, 28, 30, 31, 33, 34, 35, 36, 39, 42, 43, and 45, for example, which inhibit apolipoprotein(a) but not a second protein, which is plasminogen (see Example 22) or apolipoprotein B (see Example 23).

D. Screening and Target Validation

In a further embodiment, the "preferred target segments" identified herein may be employed in a screen for additional compounds that modulate the expression of apolipoprotein (a). "Modulators" are those compounds that decrease or increase the expression of a nucleic acid molecule encoding apolipoprotein(a) and which comprise at least an 8-nucleobase portion that is complementary to a preferred target segment. The screening method comprises the steps of contacting a preferred target segment of a nucleic acid molecule encoding apolipoprotein(a) with one or more candidate modulators, and selecting for one or more candidate modulators which decrease or increase the expression of a nucleic acid molecule encoding apolipoprotein(a). Once it is shown that the candidate modulator or modulators are capable of modulating (e.g. either decreasing or increasing) the expression of a nucleic acid molecule encoding apolipoprotein(a), the modulator may then be employed in further investigative studies of the function of apolipoprotein(a), or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processsing via an antisense mechanism. Moreover, the double-stranded moieties may be subject to chemical modifications (Fire et al., *Nature,* 1998, 391, 806-811; Timmons and Fire, *Nature* 1998, 395, 854; Timmons et al., *Gene,* 2001, 263, 103-112; Tabara et al., *Science,* 1998, 282, 430-431; Montgomery et al., *Proc. Natl. Acad. Sci. USA,* 1998, 95, 15502-15507; Tuschl et al., *Genes Dev.,* 1999, 13, 3191-3197; Elbashir et al., *Nature,* 2001, 411, 494-498; Elbashir et al., *Genes Dev.* 2001, 15, 188-200). For example, such double-stranded moieties have been shown to inhibit the target by the classical hybridization of the antisense strand of the duplex to the target, thereby triggering enzymatic degradation of the target (Tijsterman et al., *Science,* 2002, 295, 694-697).

The compounds of the present invention can also be applied in the areas of drug discovery and target validation. The present invention comprehends the use of the compounds and preferred target segments identified herein in drug discovery efforts to elucidate relationships that exist between apolipoprotein(a) and a disease state, phenotype, or condition. These methods include detecting or modulating apolipoprotein(a) comprising contacting a sample, tissue, cell, or organism with the compounds of the present invention, measuring the nucleic acid or protein level of apolipoprotein(a) and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The compounds of the present invention are utilized for diagnostics, therapeutics, and prophylaxis, and as research reagents and components of kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are used as tools in differential and/or combinatorial analyses to elucidate expression patterns of a portion or the entire complement of genes expressed within cells and tissues.

As used herein the term "biological system" or "system" is defined as any organism, cell, cell culture or tissue that expresses, or is made competent to express products of the LPA gene. These include, but are not limited to, humans, transgenic animals, cells, cell cultures, tissues, xenografts, transplants and combinations thereof.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, *FEBS Lett.,* 2000 480, 17-24; Celis, et al., *FEBS Lett.,* 2000 480, 2-16), SAGE (serial analysis of gene expression) (Madden, et al., *Drug Discov. Today,* 2000, 5, 415-425), READS (restriction enzyme amplification of digested cDNAs) (Prashar and Weissman, *Methods Enzymol.,* 1999, 303, 258-72), TOGA (total gene expression analysis) (Sutcliffe, et al., *Proc. Natl. Acad. Sci. U.S.A.,* 2000, 97, 1976-81), protein arrays and proteomics (Celis, et al., *FEBS Lett.,* 2000, 480, 2-16; Jungblut, et al., *Electrophoresis,* 1999, 20, 2100-10), expressed sequence tag (EST) sequencing (Celis, et al., *FEBS Lett.,* 2000, 480, 2-16; Larsson, et al., *J. Biotechnol.,* 2000, 80, 143-57), subtractive RNA fingerprinting (SuRF) (Fuchs, et al., *Anal. Biochem.,* 2000, 286, 91-98; Larson, et al., *Cytometry,* 2000, 41, 203-208), subtractive cloning, differential display (DD) (Jurecic and Belmont, *Curr. Opin. Microbiol.,* 2000, 3, 316-21), comparative genomic hybridization (Carulli, et al., *J. Cell Biochem. Suppl.,* 1998, 31, 286-96), FISH (fluorescent in situ hybridization) techniques (Going and Gusterson, *Eur. J. Cancer,* 1999, 35, 1895-904) and mass spectrometry methods (To, *Comb. Chem. High Throughput Screen,* 2000, 3, 235-41).

The compounds of the invention are useful for research and diagnostics, because these compounds hybridize to nucleic acids encoding apolipoprotein(a). Primers and probes disclosed herein are useful in methods requiring the specific detection of nucleic acid molecules encoding apolipoprotein (a) and in the amplification of said nucleic acid molecules for detection or for use in further studies of apolipoprotein(a). Hybridization of the primers and probes with a nucleic acid encoding apolipoprotein(a) can be detected by means known in the art. Such means may include conjugation of an enzyme to the primers and probes, radiolabelling of the primers and probes, or any other suitable detection means. Kits using such detection means for detecting the level of apolipoprotein(a) in a sample may also be prepared.

The invention further provides for the use of a compound or composition of the invention in the manufacture of a medicament for the treatment of any and all conditions disclosed herein.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of apolipoprotein(a) is treated by administering antisense compounds in accordance with this invention. For example, in one non-limiting embodiment, the methods comprise the step of administering to the animal in need of treatment, a therapeutically effective amount of a apolipoprotein(a) inhibitor. The apolipoprotein(a) inhibitors of the present invention effectively inhibit the activity of the apolipoprotein(a) protein or inhibit the expression of the apolipoprotein(a) protein. In one embodiment, the activity or expression of apolipoprotein(a) in an animal is inhibited by about 10%. Preferably, the activity or expression of apolipoprotein(a) in an animal is inhibited by about 30%. More preferably, the activity or expression of apolipoprotein(a) in an animal is inhibited by 50% or more. Thus, the oligomeric compounds modulate expression of apolipoprotein(a) mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of apolipoprotein(a) may be measured in serum, adipose tissue, liver or any other body fluid, tissue or organ of the animal. Preferably, the cells contained within said fluids, tissues or organs being analyzed contain a nucleic acid molecule encoding apolipoprotein(a) protein and/or the apolipoprotein(a) protein itself. For example, apolipoprotein(a) is produced in the liver, and can be found in normal and atherosclerotic vessel walls.

The compounds of the invention can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444;

5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In other preferred oligonucleotide mimetics, both the sugar and the internucleoside linkage (i.e. the backbone) of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497-1500.

Further embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified oligonucleotides may also contain one or more substituted sugar moieties. Preferred oligonucleotides comprise one of the following at the 2' position: OH; F; O-, S-, or N-alkyl; O-, S-, or N-alkenyl; O—, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$ONH$_2$, and O($CH_2$)$_n$ON[($CH_2$)$_n$$CH_3$]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, S$CH_3$, OCN, Cl, Br, CN, $CF_3$, O$CF_3$, SO$CH_3$, S$O_2$$CH_3$, ON$O_2$, N$O_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-β-methoxyethyl (2'-O—$CH_2$$CH_2$O$CH_3$, also known as 2'-O-(2-methoxyethyl) or 2'-methoxyethoxy or 2'-MOE) (Martin et al., *Helv. Chim. Acta*, 1995, 78, 486-504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylamino-ethoxyethoxy (also known in the art as 2', —O-dimethyl-amino-ethoxy-ethyl or 2'-DMAEOE), i.e., 2'-O—$CH_2$—O—$CH_2$—N($CH_3$)$_2$, also described in examples herein below.

Other modifications include 2'-methoxy (2'-O—$CH_3$), 2'-aminopropoxy (2'-O$CH_2$$CH_2$$CH_2$$NH_2$), 2'-allyl (2'—O—$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920; certain of which are commonly owned with the instant application, and each of which is herein incorporated by reference in its entirety.

A further modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in International Patent Publication Nos. WO 98/39352 and WO 99/14226.

Natural and Modified Nucleobases

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cyto-sines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b] [1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941; certain of which are commonly owned with the instant application, and each of which is herein incorporated by reference, and U.S. Pat. No. 5,750,692, which is commonly owned with the instant application and also herein incorporated by reference.

Conjugates

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, the entire disclosures of which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999), which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; and 5,688,941; certain of which are commonly owned with the instant application, and each of which is herein incorporated by reference.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., International Patent Publication No. WO 97/26270, incorporated by reference herein). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or at both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International Patent Publication No. WO 97/26270, incorporated by reference herein).

Particularly preferred 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-di-amino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide;

3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate; bridging or non bridging methylphosphonate and 5'-mercapto moieties (for more details see Beaucage and Tyer, 1993, Tetrahedron 49, 1925; incorporated by reference herein).

Further 3' and 5'-stabilizing groups that can be used to cap one or both ends of an oligomeric compound to impart nuclease stability include those disclosed in International Patent Publication No. WO 03/004602, published Jan. 16, 2003.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds that are chimeric compounds. "Chimeric" antisense compounds, or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases such as RNaseL, which cleaves both cellular and viral RNA. Cleavage of the RNA target can be routinely detected by gel electrophoresis and, if necessary, associated nucleic acid hybridization techniques known in the art.

Preferred chimeric oligonucleotides are those disclosed in the Examples herein. Particularly preferred chimeric oligonucleotidesare those referred to as ISIS 144367, ISIS 144368, ISIS 144379, ISIS 144381, and ISIS 144396.

Chimeric antisense compounds of the invention may be formed as composite structures of two or more oligonucleotides, modified oligonucleotides, oligonucleosides and/or oligonucleotide mimetics as described above. Chimeric antisense compounds of the invention may be formed as composite structures of two or more oligonucleotides, modified oligonucleotides, oligonucleosides and/or oligonucleotide mimetics as described above. Chimeric antisense compounds can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

Such compounds have also been referred to in the art as hybrids. In a gapmer that is 20 nucleotides in length, a gap or wing can be 1, 2, 3, 4, 5, 6, 7, 8, 9, 10, 11, 12, 13, 14, 15, 16, 17 or 18 nucleotides in length. In one embodiment, a 20-nucleotide gapmer is comprised of a gap 8 nucleotides in length, flanked on both the 5' and 3' sides by wings 6 nucleotides in length. In another embodiment, a 20-nucleotide gapmer is comprised of a gap 10 nucleotides in length, flanked on both the 5' and 3' sides by wings 5 nucleotides in length. In another embodiment, a 20-nucleotide gapmer is comprised of a gap 12 nucleotides in length flanked on both the 5' and 3' sides by wings 4 nucleotides in length. In a further embodiment, a 20-nucleotide gapmer is comprised of a gap 14 nucleotides in length flanked on both the 5' and 3' sides by wings 3 nucleotides in length. In another embodiment, a 20-nucleotide gapmer is comprised of a gap 16 nucleotides in length flanked on both the 5' and 3' sides by wings 2 nucleotides in length. In a further embodiment, a 20-nucleotide gapmer is comprised of a gap 18 nucleotides in length flanked on both the 5' and 3' ends by wings 1 nucleotide in length. Alternatively, the wings are of different lengths, for example, a 20-nucleotide gapmer may be comprised of a gap 10 nucleotides in length, flanked by a 6-nucleotide wing on one side (5' or 3') and a 4-nucleotide wing on the other side (5' or 3').

In a hemimer, an "open end" chimeric antisense compound, 20 nucleotides in length, a gap segment, located at either the 5' or 3' terminus of the oligomeric compound, can be 1, 2, 3, 4, 5, 6, 7, 8, 9, 10, 11, 12, 13, 14, 15, 16, 17, 18 or 19 nucleotides in length. For example, a 20-nucleotide hemimer can have a gap segment of 10 nucleotides at the 5' end and a second segment of 10 nucleotides at the 3' end. Alternatively, a 20-nucleotide hemimer can have a gap segment of 10 nucleotides at the 3' end and a second segment of 10 nucleotides at the 5' end.

Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922; certain of which are commonly owned with the instant application, and each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756; each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to affect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e., route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoyl-phosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoyl-phosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298, filed May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. Published Patent Application No. 2003/0040497 (Feb. 27, 2003) and its parent applications; U.S. Published Patent Application No. 2003/0027780 (Feb. 6, 2003) and its parent applications; and U.S. patent application Ser. No. 10/071,822, filed Feb. 8, 2002, each of which is incorporated herein by reference in their entirety.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Oligonucleotides may be formulated for delivery in vivo in an acceptable dosage form, e.g. as parenteral or non-parenteral formulations. Parenteral formulations include intravenous (IV), subcutaneous (SC), intraperitoneal (IP), intravitreal and intramuscular (IM) formulations, as well as formulations for delivery via pulmonary inhalation, intranasal administration, topical administration, etc. Non-parenteral formulations include formulations for delivery via the alimentary canal, e.g. oral administration, rectal administration, intrajejunal instillation, etc. Rectal administration includes administration as an enema or a suppository. Oral administration includes administration as a capsule, a gel capsule, a pill, an elixir, etc.

In some embodiments, an oligonucleotide may be administered to a subject via an oral route of administration. The subject may be an animal or a human (man). An animal subject may be a mammal, such as a mouse, rat, mouse, a rat, a dog, a guinea pig, a monkey, a non-human primate, a cat or a pig. Non-human primates include monkeys and chimpanzees. A suitable animal subject may be an experimental animal, such as a mouse, a rat, a dog, a monkey, a non-human primate, a cat or a pig.

In some embodiments, the subject may be a human. In certain embodiments, the subject may be a human patient in need of therapeutic treatment as discussed in more detail herein. In certain embodiments, the subject may be in need of modulation of expression of one or more genes as discussed in more detail herein. In some particular embodiments, the subject may be in need of inhibition of expression of one or more genes as discussed in more detail herein. In particular embodiments, the subject may be in need of modulation, i.e. inhibition or enhancement, of apolipoprotein(a) in order to obtain therapeutic indications discussed in more detail herein.

In some embodiments, non-parenteral (e.g. oral) oligonucleotide formulations according to the present invention result in enhanced bioavailability of the oligonucleotide. In this context, the term "bioavailability" refers to a measurement of that portion of an administered drug which reaches the circulatory system (e.g. blood, especially blood plasma) when a particular mode of administration is used to deliver the drug. Enhanced bioavailability refers to a particular mode of administration's ability to deliver oligonucleotide to the peripheral blood plasma of a subject relative to another mode of administration. For example, when a non-parenteral mode of administration (e.g. an oral mode) is used to introduce the drug into a subject, the bioavailability for that mode of administration may be compared to a different mode of administration, e.g. an IV mode of administration. In some embodiments, the area under a compound's blood plasma concentration curve ($AUC_0$) after non-parenteral (e.g. oral, rectal, intrajejunal) administration may be divided by the area under the drug's plasma concentration curve after intravenous (i.v.) administration ($AUC_{iv}$) to provide a dimensionless quotient (relative bioavailability, RB) that represents fraction of compound absorbed via the non-parenteral route as compared to the IV route. A composition's bioavailability is said to be enhanced in comparison to another composition's bioavailability when the first composition's relative bioavailability ($RB_1$) is greater than the second composition's relative bioavailability ($RB_2$).

In general, bioavailability correlates with therapeutic efficacy when a compound's therapeutic efficacy is related to the blood concentration achieved, even if the drug's ultimate site of action is intracellular (van Berge-Henegouwen et al., *Gastroenterol.*, 1977, 73, 300). Bioavailability studies have been used to determine the degree of intestinal absorption of a drug by measuring the change in peripheral blood levels of the drug after an oral dose (DiSanto, Chapter 76 *In: Remington's Pharmaceutical Sciences*, 18th Ed., Gennaro, ed., Mack Publishing Co., Easton, Pa., 1990, pages 1451-1458).

In general, an oral composition's bioavailability is said to be "enhanced" when its relative bioavailability is greater than the bioavailability of a composition substantially consisting of pure oligonucleotide, i.e. oligonucleotide in the absence of a penetration enhancer.

Organ bioavailability refers to the concentration of compound in an organ. Organ bioavailability may be measured in test subjects by a number of means, such as by whole-body radiography. Organ bioavailability may be modified, e.g. enhanced, by one or more modifications to the oligonucleotide, by use of one or more carrier compounds or excipients, etc. as discussed in more detail herein. In general, an increase in bioavailability will result in an increase in organ bioavailability.

Oral oligonucleotide compositions according to the present invention may comprise one or more "mucosal penetration enhancers," also known as "absorption enhancers" or simply as "penetration enhancers." Accordingly, some embodiments of the invention comprise at least one oligonucleotide in combination with at least one penetration enhancer. In general, a penetration enhancer is a substance that facilitates the transport of a drug across mucous membrane(s) associated with the desired mode of administration, e.g. intestinal epithelial membranes. Accordingly, it is desirable to select one or more penetration enhancers that facilitate the uptake of an oligonucleotide, without interfering with the activity of the oligonucleotide, and in such a manner the oligonucleotide may be introduced into the body of an animal without unacceptable side-effects such as toxicity, irritation or allergic response.

Embodiments of the present invention provide compositions comprising one or more pharmaceutically acceptable penetration enhancers, and methods of using such compositions, which result in the improved bioavailability of oligonucleotides administered via non-parenteral modes of administration. Heretofore, certain penetration enhancers have been used to improve the bioavailability of certain drugs. See Muranishi, *Crit. Rev. Ther. Drug Carrier Systems,* 1990, 7, 1 and Lee et al., *Crit. Rev. Ther. Drug Carrier Systems,* 1991, 8, 91. It has been found that the uptake and delivery of oligonucleotides, relatively complex molecules which are known to be difficult to administer to animals and man, can be greatly improved even when administered by non-parenteral means through the use of a number of different classes of penetration enhancers.

In some embodiments, compositions for non-parenteral administration include one or more modifications from naturally-occurring oligonucleotides (i.e. full-phosphodiester deoxyribosyl or full-phosphodiester ribosyl oligonucleotides). Such modifications may increase binding affinity, nuclease stability, cell or tissue permeability, tissue distribution, or other biological or pharmacokinetic property. Modifications may be made to the base, the linker, or the sugar, in general, as discussed in more detail herein with regards to oligonucleotide chemistry. In some embodiments of the invention, compositions for administration to a subject, and in particular oral compositions for administration to an animal or human subject, will comprise modified oligonucleotides having one or more modifications for enhancing affinity, stability, tissue distribution, or another biological property.

Suitable modified linkers include phosphorothioate linkers. In some embodiments according to the invention, the oligonucleotide has at least one phosphorothioate linker. Phosphorothioate linkers provide nuclease stability as well as plasma protein binding characteristics to the oligonucleotide. Nuclease stability is useful for increasing the in vivo lifetime of oligonucleotides, while plasma protein binding decreases the rate of first pass clearance of oligonucleotide via renal excretion. In some embodiments according to the present invention, the oligonucleotide has at least two phosphorothioate linkers. In some embodiments, wherein the oligonucleotide has exactly n nucleosides, the oligonucleotide has from one to n−1 phosphorothioate linkages. In some embodiments, wherein the oligonucleotide has exactly n nucleosides, the oligonucleotide has n−1 phosphorothioate linkages. In other embodiments wherein the oligonucleotide has exactly n nucleoside, and n is even, the oligonucleotide has from 1 to n/2 phosphorothioate linkages, or, when n is odd, from 1 to (n−1)/2 phosphorothioate linkages. In some embodiments, the oligonucleotide has alternating phosphodiester (PO) and phosphorothioate (PS) linkages. In other embodiments, the oligonucleotide has at least one stretch of two or more consecutive PO linkages and at least one stretch of two or more PS linkages. In other embodiments, the oligonucleotide has at least two stretches of PO linkages interrupted by at least on PS linkage.

In some embodiments, at least one of the nucleosides is modified on the ribosyl sugar unit by a modification that imparts nuclease stability, binding affinity or some other beneficial biological property to the sugar. In some cases the sugar modification includes a 2'-modification, e.g. the 2'-OH of the ribosyl sugar is replaced or substituted. Suitable replacements for 2'-OH include 2'-F and 2'-arabino-F. Suitable substitutions for OH include 2'-O-alkyl, e.g. 2-O-methyl, and 2'-O-substituted alkyl, e.g. 2'-O-methoxyethyl, 2'-O-aminopropyl, etc. In some embodiments, the oligonucleotide contains at least one 2'-modification. In some embodiments, the oligonucleotide contains at least 2 2'-modifications. In some embodiments, the oligonucleotide has at least one 2'-modification at each of the termini (i.e. the 3'- and 5'-terminal nucleosides each have the same or different 2'-modifications). In some embodiments, the oligonucleotide has at least two sequential 2'-modifications at each end of the oligonucleotide. In some embodiments, oligonucleotides further comprise at least one deoxynucleoside. In particular embodiments, oligonucleotides comprise a stretch of deoxynucleosides such that the stretch is capable of activating RNase (e.g. RNase H) cleavage of an RNA to which the oligonucleotide is capable of hybridizing. In some embodiments, a stretch of deoxynucleosides capable of activating RNase-mediated cleavage of RNA comprises about 6 to about 16, e.g. about 8 to about 16 consecutive deoxynucleosides.

Oral compositions for administration of non-parenteral oligonucleotide compositions of the present invention may be formulated in various dosage forms such as, but not limited to, tablets, capsules, liquid syrups, soft gels, suppositories, and enemas. The term "alimentary delivery" encompasses e.g. oral, rectal, endoscopic and sublingual/buccal administration. A common requirement for these modes of administration is absorption over some portion or all of the alimentary tract and a need for efficient mucosal penetration of the nucleic acid(s) so administered.

Delivery of a drug via the oral mucosa, as in the case of buccal and sublingual administration, has several desirable features, including, in many instances, a more rapid rise in plasma concentration of the drug than via oral delivery (Harvey, Chapter 35 *In: Remington's Pharmaceutical Sciences,* 18th Ed., Gennaro, ed., Mack Publishing Co., Easton, Pa., 1990, page 711).

Endoscopy may be used for drug delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., *Gan To Kagaku Ryoho,* 1992, 19(10 Suppl.), 1591). Pharmaceutical compositions, including liposomal formulations, can be delivered directly into portions of the alimentary canal, such as, e.g., the duodenum (Somogyi et al., *Pharm. Res.,* 1995, 12, 149) or the gastric submucosa (Akamo et al., *Japanese J. Cancer Res.,* 1994, 85, 652) via endoscopic means. Gastric lavage devices (Inoue et al., *Artif. Organs,* 1997, 21, 28) and percutaneous endoscopic feeding devices (Pennington et al., *Ailment Pharmacol. Ther.,* 1995, 9, 471) can also be used for direct alimentary delivery of pharmaceutical compositions.

In some embodiments, oligonucleotide formulations may be administered through the anus into the rectum or lower intestine. Rectal suppositories, retention enemas or rectal catheters can be used for this purpose and may be preferred when patient compliance might otherwise be difficult to achieve (e.g., in pediatric and geriatric applications, or when the patient is vomiting or unconscious). Rectal administration can result in more prompt and higher blood levels than the oral route. (Harvey, Chapter 35 *In: Remington's Pharmaceutical Sciences,* 18th Ed., Gennaro, ed., Mack Publishing Co., Easton, Pa., 1990, page 711). Because about 50% of the drug that is absorbed from the rectum will bypass the liver, administration by this route significantly reduces the potential for first-pass metabolism (Benet et al., Chapter 1 *In: Goodman & Gilman's The Pharmacological Basis of Therapeutics,* 9th Ed., Hardman et al., eds., McGraw-Hill, New York, N.Y., 1996).

One advantageous method of non-parenteral administration oligonucleotide compositions is oral delivery. Some embodiments employ various penetration enhancers in order to effect transport of oligonucleotides and other nucleic acids across mucosal and epithelial membranes. Penetration enhancers may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Accordingly, some embodiments comprise oral oligonucleotide compositions comprising at least one member of the group consisting of surfactants, fatty acids, bile salts, chelating agents, and non-chelating surfactants. Further embodiments comprise oral oligonucleotide comprising at least one fatty acid, e.g. capric or lauric acid, or combinations or salts thereof. Other embodiments comprise methods of enhancing the oral bioavailability of an oligonucleotide, the method comprising co-administering the oligonucleotide and at least one penetration enhancer.

Other excipients that may be added to oral oligonucleotide compositions include surfactants (or "surface-active agents"), which are chemical entities which, when dissolved in an aqueous solution, reduce the surface tension of the solution or the interfacial tension between the aqueous solution and another liquid, with the result that absorption of oligonucleotides through the alimentary mucosa and other epithelial membranes is enhanced. In addition to bile salts and fatty acids, surfactants include, for example, sodium lauryl sulfate, polyoxyethylene-9-lauryl ether and polyoxyethylene-20-cetyl ether (Lee et al., *Critical Reviews in Therapeutic Drug Carrier Systems*, 1991, page 92); and perfluorohemical emulsions, such as FC-43 (Takahashi et al., *J. Pharm. Phamacol.*, 1988, 40, 252).

Fatty acids and their derivatives which act as penetration enhancers and may be used in compositions of the present invention include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glyceryl 1-monocaprate, 1-dodecylazacycloheptan-2-one, acylcarnitines, acylcholines and mono- and di-glycerides thereof and/or physiologically acceptable salts thereof (i.e., oleate, laurate, caprate, myristate, palmitate, stearate, linoleate, etc.) (Lee et al., *Critical Reviews in Therapeutic Drug Carrier Systems*, 1991, page 92; Muranishi, *Critical Reviews in Therapeutic Drug Carrier Systems*, 1990, 7, 1; El-Hariri et al., *J. Pharm. Pharmacol.*, 1992, 44, 651).

In some embodiments, oligonucleotide compositions for oral delivery comprise at least two discrete phases, which phases may comprise particles, capsules, gel-capsules, microspheres, etc. Each phase may contain one or more oligonucleotides, penetration enhancers, surfactants, bioadhesives, effervescent agents, or other adjuvant, excipient or diluent. In some embodiments, one phase comprises at least one oligonucleotide and at least one penetration enhancer. In some embodiments, a first phase comprises at least one oligonucleotide and at least one penetration enhancer, while a second phase comprises at least one penetration enhancer. In some embodiments, a first phase comprises at least one oligonucleotide and at least one penetration enhancer, while a second phase comprises at least one penetration enhancer and substantially no oligonucleotide. In some embodiments, at least one phase is compounded with at least one degradation retardant, such as a coating or a matrix, which delays release of the contents of that phase. In some embodiments, a first phase comprises at least one oligonucleotide, and at least one penetration enhancer, while a second phase comprises at least one penetration enhancer and a release-retardant. In particular embodiments, an oral oligonucleotide comprises a first phase comprising particles containing an oligonucleotide and a penetration enhancer, and a second phase comprising particles coated with a release-retarding agent and containing penetration enhancer.

A variety of bile salts also function as penetration enhancers to facilitate the uptake and bioavailability of drugs. The physiological roles of bile include the facilitation of dispersion and absorption of lipids and fat-soluble vitamins (Brunton, Chapter 38 In: *Goodman & Gilman's The Pharmacological Basis of Therapeutics*, 9th Ed., Hardman et al., eds., McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (CDCA, sodium chenodeoxycholate), ursodeoxycholic acid (UDCA), sodium tauro-24,25-dihydrofusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782-783; Muranishi, Critical Reviews in Therapeutic Drug Carrier Systems, 1990, 7, 1; Yamamoto et al., *J. Pharm. Exp. Ther.*, 1992, 263, 25; Yamashita et al., *J. Pharm. Sci.*, 1990, 79, 579).

In some embodiments, penetration enhancers useful in some embodiments of present invention are mixtures of penetration enhancing compounds. One such penetration enhancer is a mixture of UDCA (and/or CDCA) with capric and/or lauric acids or salts thereof e.g. sodium. Such mixtures are useful for enhancing the delivery of biologically active substances across mucosal membranes, in particular intestinal mucosa. Other penetration enhancer mixtures comprise about 5-95% of bile acid or salt(s) UDCA and/or CDCA with 5-95% capric and/or lauric acid. Particular penetration enhancers are mixtures of the sodium salts of UDCA, capric acid and lauric acid in a ratio of about 1:2:2 respectively. Another such penetration enhancer is a mixture of capric and lauric acid (or salts thereof) in a 0.01:1 to 1:0.01 ratio (mole basis). In particular embodiments capric acid and lauric acid are present in molar ratios of e.g. about 0.1:1 to about 1:0.1, in particular about 0.5:1 to about 1:0.5.

Other excipients include chelating agents, i.e. compounds that remove metallic ions from solution by forming complexes therewith, with the result that absorption of oligonucleotides through the alimentary and other mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315). Chelating agents of the invention include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems*, 1991, page 92; Muranishi, *Critical Reviews in Therapeutic Drug Carrier Systems*, 1990, 7, 1; Buur et al., *J. Control Rel.*, 1990, 14, 43).

As used herein, non-chelating non-surfactant penetration enhancers may be defined as compounds that demonstrate insignificant activity as chelating agents or as surfactants but that nonetheless enhance absorption of oligonucleotides through the alimentary and other mucosal membranes (Muranishi, *Critical Reviews in Therapeutic Drug Carrier Systems,* 1990, 7, 1). This class of penetration enhancers includes, but is not limited to, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621).

Agents that enhance uptake of oligonucleotides at the cellular level may also be added to the pharmaceutical and other compositions of the present invention. For example, cationic lipids, such as lipofectin (Junichi et al, U.S. Pat. No. 5,705, 188), cationic glycerol derivatives, and polycationic molecules, such as polylysine (Lollo et al., PCT Application WO 97/30731), can be used.

Some oral oligonucleotide compositions also incorporate carrier compounds in the formulation. As used herein, "carrier compound" or "carrier" can refer to a nucleic acid, or analog thereof, which may be inert (i.e., does not possess biological activity per se) or may be necessary for transport, recognition or pathway activation or mediation, or is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'-isothiocyano-stilbene-2,2'-disulfonic acid (Miyao et al., *Antisense Res. Dev.,* 1995, 5, 115; Takakura et al., *Antisense & Nucl. Acid Drug Dev.,* 1996, 6, 177).

A "pharmaceutical carrier" or "excipient" may be a pharmaceutically acceptable solvent, suspending agent or any other pharmacologically inert vehicle for delivering one or more nucleic acids to an animal. The excipient may be liquid or solid, and is selected with the planned manner of administration in mind so as to provide for the desired bulk, consistency, etc., when combined with a nucleic acid and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, EXPLOTAB™ disintegrating agent); and wetting agents (e.g., sodium lauryl sulphate, etc.).

Oral oligonucleotide compositions may additionally contain other adjunct components conventionally found in pharmaceutical compositions, at their art-established usage levels. Thus, for example, the compositions may contain additional, compatible, pharmaceutically-active materials such as, for example, antipuritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the present invention.

Certain embodiments of the invention provide pharmaceutical compositions containing one or more oligomeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethyl-nitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. For example, the first target may be an apolipoprotein(a) target, and the second target may be a region from another nucleotide sequence. Alternatively, compositions of the invention may contain two or more antisense compounds targeted to different regions of the same apolipoprotein(a) nucleic acid target. Numerous examples of antisense compounds are illustrated herein, and others may be selected from among suitable compounds known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, from 0.1 µg to 10 g per kg of body weight, from 1.0 µg to 1 g per kg of body weight, from 10.0 µg to 100 mg per kg of body weight, from 100 µg to 10 mg per kg of body weight, or from 1 mg to 5 mg per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

The effects of treatments with therapeutic compositions can be assessed following collection of tissues or fluids from a patient or subject receiving said treatments. It is known in the art that a biopsy sample can be procured from certain tissues without resulting in detrimental effects to a patient or subject. In certain embodiments, a tissue and its constituent cells comprise, but are not limited to, blood (e.g., hematopoietic cells, such as human hematopoietic progenitor cells, human hematopoietic stem cells, $CD34^+$ cells $CD4^+$ cells), lymphocytes and other blood lineage cells, bone marrow, breast, cervix, colon, esophagus, lymph node, muscle, peripheral blood, oral mucosa and skin. In other embodiments, a fluid and its constituent cells comprise, but are not limited to, blood, urine, semen, synovial fluid, lymphatic fluid and cerebro-spinal fluid. Tissues or fluids procured from patients can be evaluated for expression levels of the target mRNA or protein. Additionally, the mRNA or protein expression levels of other genes known or suspected to be associated with the specific disease state, condition or phenotype can be assessed. mRNA levels can be measured or evaluated by real-time PCR, Northern blot, in situ hybridization or DNA array analysis. Protein levels can be measured or evaluated by ELISA, immunoblotting, quantitative protein assays, protein activity assays (for example, caspase activity assays) immunohistochemistry or immunocytochemistry. Furthermore, the effects of treatment can be assessed by measuring biomarkers associated with the disease or condition in the aforementioned tissues and fluids, collected from a patient or subject receiving treatment, by routine clinical methods known in the art. These biomarkers include but are not limited to: glucose, cholesterol, lipoproteins, triglycerides, free fatty acids and other markers of glucose and lipid metabolism; liver transaminases, bilirubin, albumin, blood urea nitrogen, creatine and other markers of kidney and liver function; interleukins, tumor necrosis factors, intracellular adhesion molecules, C-reactive protein and other markers of inflammation; testosterone, estrogen and other hormones; tumor markers; vitamins, minerals and electrolytes.

While the present invention has been described with specificity in accordance with certain of its preferred embodiments, the following examples serve only to illustrate the invention and are not intended to limit the same. Each of the references, GENBANK® accession numbers, as well as each application from which the present application claims priority, and the like recited in the present application is incorporated herein by reference in its entirety.

EXAMPLES

Example 1

Synthesis of Nucleoside Phosphoramidites

The following compounds, including amidites and their intermediates were prepared as described in U.S. Pat. No. 6,426,220 and International Patent Publication No. WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2', —O-(2-methoxyethyl)-5-methyluridin-3'-O-yl]-2-cyanoethyl-N,N-diisopropylphosphoramidite (MOE T amidite), 5', —O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-$O^2$-2'-anhydro-5-methyluridine, 5', —O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2', —O—[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors, including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or 5,366,878, herein incorporated by reference.

Alkylphosphonothioate oligonucleotides are prepared as described in International Patent Application Nos. PCT/US94/00902 and PCT/US93/06976 (published as International Patent Publication Nos. WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825; 5,386,023; 5,489,677; 5,602,240; and 5,610,289; all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group that has the following important properties. It is stable to the conditions of nucleoside phosphoramidite synthesis and oligonucleotide synthesis. However, after oligonucleotide synthesis the oligonucleotide is treated with methylamine, which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820-11821; Matteucci, M. D. and Caruthers, M. H. *J. Am. Chem. Soc.*, 1981, 103, 3185-3191; Beaucage, S. L. and Caruthers, M. H. *Tetrahedron Lett.*, 1981, 22, 1859-1862; Dahl, B. J., et al., *Acta Chem. Scand.*, 1990, 44, 639-641; Reddy, M. P., et al., *Tetrahedron Lett.*, 1994, 25, 4311-4314; Wincott, F. et al., *Nucleic Acids Res.*, 1995, 23, 2677-2684; Griffin, B. E., et al., *Tetrahedron*, 1967, 23, 2301-2313; Griffin, B. E., et al., *Tetrahedron*, 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 μl of each of the complementary strands of RNA oligonucleotides (50 μM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 4

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligo-nucleotide segments are synthesized using an Applied Biosystems automated DNA synthesizer Model 394, as above. Oligonucleotides are synthesized using the automated synthesizer and 2'-deoxy-5'-dimethoxytrityl-3',—O-phosphoramidite for the DNA portion and 5'-dimethoxy-trityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spectrophotometrically for yield and for purity by capillary electrophoresis and by mass spectrometry).

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl)phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/5 oligonucleosides are synthesized according to U.S. Pat. No. 5,623,065, herein incorporated by reference.

Example 5

Design and Screening of Duplexed Antisense Compounds Targeting Apolipoprotein(a)

In accordance with the present invention, a series of nucleic acid duplexes comprising the antisense compounds of the present invention and their complements can be designed to target apolipoprotein(a). The nucleobase sequence of the antisense strand of the duplex comprises at least an 8-nucleobase portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini. The antisense and sense strands of the duplex comprise from about 17 to 25 nucleotides, or from about 19 to 23 nucleotides. Alternatively, the antisense and sense strands comprise 20, 21 or 22 nucleotides.

For example, a duplex comprising an antisense strand having the sequence CGAGAGGCGGACGGGACCG (SEQ ID NO: 97) and having a two-nucleobase overhang of deoxythymidine(dT) has the following structure (Antisense SEQ ID NO: 98, Complement SEQ ID NO: 99):

```
cgagaggcggacgggaccgTT  Antisense Strand
||||||||||||||||||||
TTgctctccgcctgccctggc  Complement
```

Overhangs can range from 2 to 6 nucleobases and these nucleobases may or may not be complementary to the target nucleic acid. In another embodiment, the duplexes may have an overhang on only one terminus.

In another embodiment, a duplex comprising an antisense strand having the same sequence CGAGAGGCGGACGG-GACCG (SEQ ID NO: 97) is prepared with blunt ends (no single stranded overhang) as shown (Antisense SEQ ID NO: 97, Complement SEQ ID NO: 100):

```
cgagaggcggacgggaccg  Antisense Strand
|||||||||||||||||||
gctctccgcctgccctggc  Complement
```

The RNA duplex can be unimolecular or bimolecular; i.e., the two strands can be part of a single molecule or may be separate molecules.

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 µM. Once diluted, 30 µL of each strand is combined with 15 µL of a 5× solution of annealing buffer. The final concentration of said buffer is 100 mM potassium acetate, 30 mM HEPES-KOH pH 7.4, and 2 mM magnesium acetate. The final volume is 75 µL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 µM. This solution can be stored frozen (−20° C.) and freeze-thawed up to 5 times.

Once prepared, the duplexed antisense compounds are evaluated for their ability to modulate apolipoprotein(a) expression.

When cells reached 80% confluency, they are treated with duplexed antisense compounds of the invention. For cells grown in 96-well plates, wells are washed once with 200 µL OPTI-MEM-1 reduced-serum medium (Gibco BRL) and then treated with 130 µL of OPTI-MEM-1 containing 12 µg/mL LIPOFECTIN™ reagent (Invitrogen Life Technologies, Carlsbad, Calif.) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full-length material. The relative amounts of phosphorothioate and phosphodiester linkages obtained in the synthesis were determined by the ratio of correct molecular weight relative to the −16 amu product (+/−32+/−48). For some studies oligonucleotides were purified by HPLC, as described by Chiang et al., J. Biol. Chem. 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH$_4$OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis-96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ apparatus) or, for individually prepared samples, on a commercial CE apparatus (e.g., Beckman P/ACE™ 5000, ABI 270 apparatus). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effects of antisense compounds on target nucleic acid expression are tested in any of a variety of cell types, provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 μg/mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 μg/mL (Invitrogen Corporation, Carlsbad, Calif.). Cells were routinely passaged by trypsinization and dilution when they reached 90% confluence.

NHDF Cells:

Human neonatal dermal fibroblasts (NHDFs) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Treatment with Antisense Compounds:

When cells reached 65-75% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 medium containing 3.75 μg/mL LIPOFECTIN™ reagent (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCTCAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of Apolipoprotein(a) Expression

Antisense modulation of apolipoprotein(a) expression can be assayed in a variety of ways known in the art. For example, apolipoprotein(a) mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of apolipoprotein(a) can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to apolipoprotein(a) can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays and In Vivo Studies for the Use of Apolipoprotein(a) Inhibitors Phenotypic Assays Once apolipoprotein(a) inhibitors have been identified by the methods disclosed herein, the compounds are further investigated in one or more phenotypic assays, each having measurable endpoints predictive of efficacy in the treatment of a particular disease state or condition. Phenotypic assays, kits and reagents for their use are well known to those skilled in the art and are herein used to investigate the role and/or association of apolipoprotein(a) in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with apolipoprotein(a) inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status, which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the apolipoprotein(a) inhibitors. Hallmark genes, or those genes suspected to be associated with a specific disease state, condition, or phenotype, are measured in both treated and untreated cells.

The cells subjected to the phenotypic assays described herein derive from in vitro cultures or from tissues or fluids isolated from living organisms, both human and non-human. In certain embodiments, a tissue and its constituent cells comprise, but are not limited to, blood (e.g., hematopoietic cells, such as human hematopoietic progenitor cells, human hematopoietic stem cells, CD34$^+$ cells CD4$^+$ cells), lymphocytes and other blood lineage cells, bone marrow, brain, stem cells, blood vessel, liver, lung, bone, breast, cartilage, cervix, colon, cornea, embryonic, endometrium, endothelial, epithelial, esophagus, facia, fibroblast, follicular, ganglion cells, glial cells, goblet cells, kidney, lymph node, muscle, neuron, ovaries, pancreas, peripheral blood, prostate, skin, skin, small intestine, spleen, stomach, testes and fetal tissue. In other embodiments, a fluid and its constituent cells comprise, but is not limited to, blood, urine, synovial fluid, lymphatic fluid and cerebro-spinal fluid. The phenotypic assays may also be performed on tissues treated with apolipoprotein(a) inhibitors ex vivo.

In Vivo Studies

The individual subjects of the in vivo studies described herein are warm-blooded vertebrate animals, including humans.

The clinical trial is subjected to rigorous controls to ensure that individuals are not unnecessarily put at risk and that they are fully informed about their role in the study.

To account for the psychological effects of receiving treatments, volunteers are randomly given placebo or apolipoprotein(a) inhibitor. Furthermore, to prevent the doctors from being biased in treatments, they are not informed as to whether the medication they are administering is a apolipoprotein(a) inhibitor or a placebo. Using this randomization approach, each volunteer has the same chance of being given either the new treatment or the placebo.

Volunteers receive either the apolipoprotein(a) inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding apolipoprotein (a) or apolipoprotein(a) protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and apolipoprotein(a) inhibitor treatment. In general, the volunteers treated with placebo have little or no response to treatment, whereas the volunteers treated with the apolipoprotein(a) inhibitor show positive trends in their disease state or condition index at the conclusion of the study.

Example 12

RNA Isolation

Poly(A)+ mRNA Isolation

Poly(A)+ mRNA was isolated according to Miura et al., (*Clin. Chem.*, 1996, 42, 1758-1764). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY™ 96 kit and buffers purchased from Qiagen, Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY™ 96 well plate attached to a QIAVAC™ manifold fitted with a waste collection tray and attached to a vacuum source. Vacuum was applied for 1 minute. 500 µL of Buffer RW1 was added to each well of the RNEASY™ 96 plate and incubated for 15 minutes and the vacuum was again applied for 1 minute. An additional 500 µL of Buffer RW1 was added to each well of the RNEASY™ 96 plate and the vacuum was applied for 2 minutes. 1 mL of Buffer RPE was then added to each well of the RNEASY™ 96 plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 µL of RNase free water into each well, incubating 1 minute, and then applying the vacuum for 3 minutes.

The repetitive pipetting and elution steps may be automated using a QIAGEN® Bio-Robot™ 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of Apolipoprotein(a) mRNA Levels

Quantitation of apolipoprotein(a) mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

Prior to the real-time PCR, isolated RNA is subjected to a reverse transcriptase (RT) reaction, for the purpose of generating complementary DNA (cDNA), from which the real-time PCR product is amplified. Reverse transcriptase and PCR reagents were obtained from Invitrogen Corporation, (Carlsbad, Calif.). RT, real-time PCR reactions carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNase inhibitor, 1.25 Units PLATINUM® Taq polymerase, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq polymerase, 40 cycles of a two-step PCR protocol were carried out: 95° C. for 15 seconds (denaturation) followed by 60° C. for 1.5 minutes (annealing/extension). The method of obtaining gene target quantities by RT, real-time PCR is herein referred to as real-time PCR.

Gene target quantities obtained by RT, real-time PCR are normalized using either the expression level of GAPDH, a gene whose expression is constant, or by quantifying total RNA using RIBOGREEN™ reagent (Molecular Probes, Inc. Eugene, Oreg.). GAPDH expression is quantified by real-time PCR, by being run simultaneously with the target, multiplexing, or separately. Total RNA is quantified using RIBOGREEN™ RNA quantification reagent (Molecular Probes, Inc. Eugene, Oreg.). Methods of RNA quantification by RIBOGREEN™ reagent are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 apparatus (PE Applied Biosystems) with excitation at 485 nm and emission at 530 nm.

Probes and primers to human apolipoprotein(a) were designed to hybridize to a human apolipoprotein(a) sequence, using published sequence information (GENBANK® accession number NM_005577.1, incorporated herein as SEQ ID NO: 4). For human apolipoprotein(a) the PCR primers were: forward primer: CAGCTCCTTATTGTTATACGAGGGA (SEQ ID NO: 5)
reverse primer: TGCGTCTGAGCATTGCGT (SEQ ID NO: 6) and the PCR probe was: FAM-CCCGGTGTCAGGTGG-GAGTACTGC-TAMRA (SEQ ID NO: 7) where FAM is the fluorescent dye and TAMRA is the quencher dye.

Gene target quantities in mouse cells are tissues are normalized using mouse GAPDH expression. For mouse GAPDH the PCR primers were:
forward primer: GGCAAATTCAACGGCACAGT (SEQ ID NO: 8)
reverse primer: GGGTCTCGCTCCTGGAAGAT (SEQ ID NO: 9) and the PCR probe was: 5' JOE-AAGGC-CGAGAATGGGAAGCTTGTCATC-TAMRA 3' (SEQ ID NO: 10) where JOE is the fluorescent reporter dye and TAMRA is the quencher dye.

Example 14

Northern Blot Analysis of Apolipoprotein(a) mRNA Levels

Eighteen hours after antisense treatment, cell monolayers were washed twice with cold PBS and lysed in 1 mL RNA-ZOL™ reagent (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBONDT™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 apparatus (Stratagene, Inc, La Jolla, Calif.) and then probed using QUICKHYB™ hybridization solution (Stratagene, La Jolla, Calif.) using manufacturer's recommendations for stringent conditions.

To detect human apolipoprotein(a), a human apolipoprotein(a) specific probe was prepared by PCR using the forward primer CAGCTCCTTATTGTTATACGAGGGA (SEQ ID NO: 5) and the reverse primer TGCGTCTGAGCATTGCGT (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ apparatus and IMAGEQUANT™ Software V3.3 (Molecular Dynamics, Sunnyvale, Calif.). Data was normalized to GAPDH levels in untreated controls.

Example 15

Antisense Inhibition of Human Apolipoprotein(a) Expression by Chimeric Phosphorothioate Oligonucleotides Having 2'-MOE Wings and a Deoxy Gap In accordance with the present invention, a series of antisense compounds was designed to target different regions of the human apolipoprotein(a) RNA, using published sequences (GENBANK® accession number NM_005577.1, incorporated herein as SEQ ID NO: 4). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines.

Apolipoprotein(a) is found in humans, nonhuman primates and the European hedgehog, but not in common laboratory animals such as rats and mice. Transgenic mice which express human apolipoprotein(a) have been engineered (Chiesa et al., *J. Biol. Chem.*, 1992, 267, 24369-24374). The use of primary hepatocytes prepared from human apolipoprotein(a) transgenic mice circumvents the issue of variability when testing antisense oligonucleotide activity in primary cells. Accordingly, primary mouse hepatocytes prepared from the human apolipoprotein(a) transgenic mice were used to investigate the effects of antisense oligonucleotides on human apolipoprotein(a) expression. The human apolipoprotein(a) transgenic mice were obtained from Dr. Robert Pitas and Dr. Matthias Schneider in the Gladstone Institute at the University of California, San Francisco. Primary hepatocytes were isolated from these mice and were cultured in DMEM, high glucose (Invitrogen Corporation, Carlsbad, Calif.) supplemented with 10% fetal bovine serum, (Invitrogen Corporation, Carlsbad, Calif.), 100 units per mL penicillin and 100 μg/mL streptomycin (Invitrogen Corporation, Carlsbad, Calif.). For treatment with oligonucleotide, cells were washed once with serum-free DMEM and subsequently transfected with a dose of 150 nM of antisense oligonucleotide using LIPOFECTIN™ reagent (Invitrogen Corporation, Carlsbad, Calif.) as described in other examples herein. The compounds were analyzed for their effect on human apolipoprotein(a) mRNA levels by quantitative real-time PCR as described in other examples herein. Gene target quantities obtained by real time RT-PCR were normalized using mouse GAPDH.

Data are averages from three experiments in which primary transgenic mouse hepatocytes were treated with 150 nM of antisense oligonucleotides targeted to human apolipoprotein (a).

TABLE 1

Inhibition of human apolipoprotein(a) mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 144367 | Coding | 4 | 174 | ggcaggtccttcctgtgaca | 53 | 11 |
| 144368 | Coding | 4 | 352 | tctgcgtctgagcattgcgt | 87 | 12 |
| 144369 | Coding | 4 | 522 | aagcttggcaggttcttcct | 0 | 13 |
| 144370 | Coding | 4 | 1743 | tcggaggcgcgacggcagtc | 40 | 14 |
| 144371 | Coding | 4 | 2768 | cggaggcgcgacggcagtcc | 0 | 15 |
| 144372 | Coding | 4 | 2910 | ggcaggttcttcctgtgaca | 65 | 16 |
| 144373 | Coding | 4 | 3371 | ataacaataaggagctgcca | 50 | 17 |
| 144374 | Coding | 4 | 4972 | gaccaagcttggcaggttct | 62 | 18 |
| 144375 | Coding | 4 | 5080 | taacaataaggagctgccac | 36 | 19 |
| 144376 | Coding | 4 | 5315 | tgaccaagcttggcaggttc | 25 | 20 |
| 144377 | Coding | 4 | 5825 | ttctgcgtctgagcattgcg | 38 | 21 |

TABLE 1-continued

Inhibition of human apolipoprotein(a) mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 144378 | Coding | 4 | 6447 | aacaataaggagctgccaca | 29 | 22 |
| 144379 | Coding | 4 | 7155 | acctgacaccgggatccctc | 79 | 23 |
| 144380 | Coding | 4 | 7185 | ctgagcattgcgtcaggttg | 16 | 24 |
| 144381 | Coding | 4 | 8463 | agtagttcatgatcaagcca | 71 | 25 |
| 144382 | Coding | 4 | 8915 | gacggcagtcccttctgcgt | 34 | 26 |
| 144383 | Coding | 4 | 9066 | ggcaggttcttccagtgaca | 5 | 27 |
| 144384 | Coding | 4 | 10787 | tgaccaagcttggcaagttc | 31 | 28 |
| 144385 | Coding | 4 | 11238 | tataacaccaaggactaatc | 9 | 29 |
| 144386 | Coding | 4 | 11261 | ccatctgacattgggatcca | 66 | 30 |
| 144387 | Coding | 4 | 11461 | tgtggtgtcatagaggacca | 36 | 31 |
| 144388 | Coding | 4 | 11823 | atgggatcctccgatgccaa | 55 | 32 |
| 144389 | Coding | 4 | 11894 | acaccaagggcgaatctcag | 58 | 33 |
| 144390 | Coding | 4 | 11957 | ttctgtcactggacatcgtg | 59 | 34 |
| 144391 | Coding | 4 | 12255 | cacacggatcggttgtgtaa | 58 | 35 |
| 144392 | Coding | 4 | 12461 | acatgtccttcctgtgacag | 51 | 36 |
| 144393 | Coding | 4 | 12699 | cagaaggaggccctaggctt | 33 | 37 |
| 144394 | Coding | 4 | 13354 | ctggcggtgaccatgtagtc | 52 | 38 |
| 144395 | 3'UTR | 4 | 13711 | tctaagtaggttgatgcttc | 68 | 39 |
| 144396 | 3'UTR | 4 | 13731 | tccttacccacgtttcagct | 70 | 40 |
| 144397 | 3'UTR | 4 | 13780 | ggaacagtgtcttcgtttga | 63 | 41 |
| 144398 | 3'UTR | 4 | 13801 | gtttggcatagctggtagct | 44 | 42 |
| 144399 | 3'UTR | 4 | 13841 | accttaaaagcttatacaca | 57 | 43 |
| 144400 | 3'UTR | 4 | 13861 | atacagaatttgtcagtcag | 21 | 44 |
| 144401 | 3'UTR | 4 | 13881 | gtcatagctatgacacctta | 46 | 45 |

As shown in Table 1, SEQ ID NOs 11, 12, 14, 16, 17, 18, 19, 21, 23, 25, 30, 31, 32, 33, 34, 35, 36, 38, 39, 40, 41, 42, 43 and 45 demonstrated at least 35% inhibition of human apolipoprotein(a) expression in this assay and are therefore preferred. More preferred are SEQ ID NOs 23, 12 and 40. The target regions to which these preferred sequences are complementary are herein referred to as "preferred target segments" and are therefore preferred for targeting by compounds of the present invention. These preferred target segments are shown in Table 2. These sequences are shown to contain thymine (T) but one of skill in the art will appreciate that thymine (T) is generally replaced by uracil (U) in RNA sequences. The sequences represent the reverse complement of the preferred antisense compounds shown in Table 1. "Target site" indicates the first (5'-most) nucleotide number on the particular target nucleic acid to which the oligonucleotide binds. Also shown in Table 2 is the species in which each of the preferred target segments was found.

TABLE 2

Sequence and position of preferred target segments identified in apolipoprotein(a).

| TARGET SITE ID | SEQ ID NO | TARGET SITE | SEQUENCE | REV COMP OF SEQ ID | ACTIVE IN | SEQ ID NO |
|---|---|---|---|---|---|---|
| 57364 | 4 | 174 | tgtcacaggaaggacctgcc | 11 | H. sapiens | 46 |
| 57365 | 4 | 352 | acgcaatgctcagacgcaga | 12 | H. sapiens | 47 |
| 57367 | 4 | 1743 | gactgccgtcgcgcctccga | 14 | H. sapiens | 48 |
| 57369 | 4 | 2910 | tgtcacaggaagaacctgcc | 16 | H. sapiens | 49 |
| 57370 | 4 | 3371 | tggcagctccttattgttat | 17 | H. sapiens | 50 |
| 57371 | 4 | 4972 | agaacctgccaagcttggtc | 18 | H. sapiens | 51 |
| 57372 | 4 | 5080 | gtggcagctccttattgtta | 19 | H. sapiens | 52 |
| 57374 | 4 | 5825 | cgcaatgctcagacgcagaa | 21 | H. sapiens | 53 |
| 57376 | 4 | 7155 | gagggatcccggtgtcaggt | 23 | H. sapiens | 54 |
| 57378 | 4 | 8463 | tggcttgatcatgaactact | 25 | H. sapiens | 55 |
| 57383 | 4 | 11261 | tggatcccaatgtcagatgg | 30 | H. sapiens | 56 |
| 57384 | 4 | 11461 | tggtcctctatgacaccaca | 31 | H. sapiens | 57 |

TABLE 2-continued

Sequence and position of preferred target segments identified in apolipoprotein(a).

| SITE ID | TARGET SEQ ID NO | TARGET SITE | SEQUENCE | REV COMP OF SEQ ID | ACTIVE IN | SEQ ID NO |
|---|---|---|---|---|---|---|
| 57385 | 4 | 11823 | ttggcatcggaggatcccat | 32 | H. sapiens | 58 |
| 57386 | 4 | 11894 | ctgagattcgccttggtgt | 33 | H. sapiens | 59 |
| 57387 | 4 | 11957 | cacgatgtccagtgacagaa | 34 | H. sapiens | 60 |
| 57388 | 4 | 12255 | ttacacaaccgatccgtgtg | 35 | H. sapiens | 61 |
| 57389 | 4 | 12461 | ctgtcacaggaaggacatgt | 36 | H. sapiens | 62 |
| 57391 | 4 | 13354 | gactacatggtcaccgccag | 38 | H. sapiens | 63 |
| 57392 | 4 | 13711 | gaagcatcaacctacttaga | 39 | H. sapiens | 64 |
| 57393 | 4 | 13731 | agctgaaacgtgggtaagga | 40 | H. sapiens | 65 |
| 57394 | 4 | 13780 | tcaaacgaagacactgttcc | 41 | H. sapiens | 66 |
| 57395 | 4 | 13801 | agctaccagctatgccaaac | 42 | H. sapiens | 67 |
| 57396 | 4 | 13841 | tgtgtataagcttttaaggt | 43 | H. sapiens | 68 |
| 57398 | 4 | 13881 | taaggtgtcatagctatgac | 45 | H. sapiens | 69 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of apolipoprotein(a).

According to the present invention, antisense compounds include antisense oligomeric compounds, antisense oligonucleotides, siRNAs, external guide sequence (EGS) oligonucleotides, alternate splicers, and other short oligomeric compounds that hybridize to at least a portion of the target nucleic acid.

Example 16

Western Blot Analysis of Apolipoprotein(a) Protein Levels

Western blot analysis (immunoblot analysis) is carried out using standard methods. Cells are harvested 16-20 h after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to apolipoprotein(a) is used, with a radiolabeled or fluorescently labeled secondary antibody directed against the primary antibody species. Bands are visualized using a PHOSPHORIMAGER™ apparatus (Molecular Dynamics, Sunnyvale Calif.).

Example 17

Antisense Inhibition of Human Apolipoprotein(a) in Transgenic Primary Mouse Hepatocytes: Dose Response In accordance with the present invention, antisense oligonucleotides identified as having good activity based on the results in Example 15 were further investigated in dose-response studies. Primary hepatocytes from human apolipoprotein(a) transgenic mice were treated with 10, 50, 150 or 300 nM of ISIS 144396 (SEQ ID NO: 40), ISIS 144368 (SEQ ID NO: 12), ISIS 144379 (SEQ ID NO: 23) or ISIS 113529 (CTCTTACTGTGCTGTGGACA, SEQ ID NO: 70). ISIS 113529, which does not target apolipoprotein(a), was used as a control oligonucleotide and is a chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE)nucleotides. The internucleoside (backbone) linkages are phosphorothioate (P=S) throughout the oligonucleotide. All cytidine residues are 5-methylcytidines.

Following 24 hours of exposure to antisense oligonucleotides, target mRNA expression levels were evaluated by quantitative real-time PCR as described in other examples herein. The results are the average of 4 experiments for apolipoprotein(a) antisense oligonucleotides and the average of 12 experiments for the control oligonucleotide. The data are expressed as percent inhibition of apolipoprotein(a) expression relative to untreated controls and are shown in Table 3.

TABLE 3

Antisense inhibition of human apolipoprotein(a) in transgenic primary mouse hepatocytes: dose response

| Oligonucleotide dose | % Inhibition of transgenic human lipoprotein(a) ISIS # | | | |
|---|---|---|---|---|
| | 144396 | 144368 | 144379 | 113529 |
| 10 nM | 0 | 11 | 55 | N.D. |
| 50 nM | 0 | 26 | 73 | N.D. |
| 150 nM | 0 | 58 | 85 | N.D. |
| 300 nM | 9 | 62 | 89 | 0 |

These data demonstrate that ISIS 144368 and ISIS 144379 inhibited the expression of human apolipoprotein(a) in a dose-dependent fashion.

Example 18

Oil Red O Stain

Hepatic steatosis, or accumulation of lipids in the liver, is assessed by routine histological analysis of frozen liver tissue sections stained with oil red O stain, which is commonly used to visualize lipid deposits, and counterstained with hematoxylin and eosin, to visualize nuclei and cytoplasm, respectively. Tissue is preserved in 10% neutral-buffered formalin, embedded in paraffin, sectioned and stained.

Example 19

Animal Models

In addition to human systems, which express apolipoprotein(a), biological systems of other mammals are also available for studies of expression products of the LPA gene as well as for studies of the Lp(a) particles and their role in physiologic processes.

Transgenic mice which express human apolipoprotein(a) have been engineered (Chiesa et al., *J. Biol. Chem.*, 1992, 267, 24369-24374) and are used as an animal model for the investigation of the in vivo activity of the oligonucleotides of this invention. Although transgenic mice expressing human apolipoprotein(a) exist, they fail to assemble Lp(a) particles because of the inability of human apolipoprotein(a) to associate with mouse apolipoprotein B. When mice expressing human apolipoprotein(a) are bred to mice expressing human apolipoprotein B, the Lp(a) particle is efficiently assembled (Callow et al., *Proc. Natl. Acad. Sci. USA*, 1994, 91, 2130-2134). Accordingly mice expressing both human apolipoprotein(a) and human apolipoprotein B transgenes are used for animal model studies in which the secretion of the Lp(a) particle is evaluated.

Where additional genetic alterations are necessary, mice with either a single human transgene (human apolipoprotein (a) or human apolipoprotein B) or both human transgenes (human apolipoprotein(a) and human apolipoprotein B) are bred to mice with a desired genetic mutation. The offspring with the desired combination of transgene(s) and genetic mutation(s) is selected for use as an animal model. In one nonlimiting example, mice expressing both human apolipoprotein(a) and human apolipoprotein B are bred to mice with a mutation in the leptin gene, yielding offspring producing human Lp(a) particles in an ob/ob model of obesity and diabetes.

ob/ob mice

Leptin is a hormone produced by fat that regulates appetite. Deficiencies in this hormone in both humans and non-human animals leads to obesity. ob/ob mice have a mutation in the leptin gene which results in obesity and hyperglycemia. As such, these mice are a useful model for the investigation of obesity and treatments designed to reduce obesity.

Seven-week old male C57Bl/6J-Lep ob/ob mice (Jackson Laboratory, Bar Harbor, Me.) are fed a diet with a fat content of 10-15% and are subcutaneously injected with oligonucleotides of the present invention or a control oligonucleotide at a dose of 5, 10 or 25 mg/kg two times per week for 4 weeks. Saline-injected animals and leptin wildtype littermates (i.e. lean littermates) serve as controls. After the treatment period, mice are sacrificed and target levels are evaluated in liver, brown adipose tissue (BAT) and white adipose tissue (WAT). RNA isolation and target mRNA expression level quantitation are performed as described by other examples herein.

To assess the physiological effects resulting from antisense inhibition of target apolipoprotein(a) mRNA, the ob/ob mice that receive antisense oligonucleotide treatment are further evaluated at the end of the treatment period for serum lipids, serum apolipoproteins, serum free fatty acids, serum cholesterol (CHOL), liver triglycerides, and fat tissue triglycerides. Serum components are measured on routine clinical diagnostic instruments. Tissue triglycerides are extracted using an acetone extraction technique known in the art, and subsequently measured by ELISA. The presence of the Lp(a) particle in the serum is measured using a commercially available ELISA kit (ALerCHEK Inc., Portland, Me.). Hepatic steatosis, or accumulation of lipids in the liver, is assessed by measuring the liver triglyceride content. Hepatic steatosis is also assessed by routine histological analysis of frozen liver tissue sections stained with oil red O stain, which is commonly used to visualize lipid deposits, and counterstained with hematoxylin and eosin, to visualize nuclei and cytoplasm, respectively.

The effects of apolipoprotein(a) inhibition on glucose and insulin metabolism are also evaluated in the ob/ob mice treated with antisense oligonucleotides of this invention. Plasma glucose is measured at the start of the antisense oligonucleotide treatment and after 2 weeks and 4 weeks of treatment. Plasma insulin is similarly at the beginning to of the treatment, and following 2 weeks and 4 weeks of treatment. Glucose and insulin tolerance tests are also administered in fed and fasted mice. Mice receive intraperitoneal injections of either glucose or insulin, and the blood glucose and insulin levels are measured before the insulin or glucose challenge and at 15, 20 or 30 minute intervals for up to 3 hours.

To assess the metabolic rate of ob/ob mice treated with antisense oligonucleotides of this invention, the respiratory quotient and oxygen consumption of the mice are also measured.

The ob/ob mice that received antisense oligonucleotide treatment are further evaluated at the end of the treatment period for the effects of apolipoprotein(a) inhibition on the expression of genes that participate in lipid metabolism, cholesoterol biosynthesis, fatty acid oxidation, fatty acid storage, gluconeogenesis and glucose metabolism. These genes include, but are not limited to, HMG-CoA reductase, acetyl-CoA carboxylase 1 and acetyl-CoA carboxylase 2, carnitine palmitoyltransferase I and glycogen phosphorylase, glucose-6-phosphatase and phosphoenolpyruvate carboxykinase 1, lipoprotein lipase and hormone sensitive lipase. mRNA levels in liver and white and brown adipose tissue are quantitated by real-time PCR as described in other examples herein, employing primer-probe sets that were generated using published sequences of each gene of interest.

db/db Mice

A deficiency in the leptin hormone receptor mouse also results in obesity and hyperglycemia. These mice are referred to as db/db mice and, like the ob/ob mice, are used as a mouse model of obesity.

Seven-week old male C57Bl/6J-Lepr db/db mice (Jackson Laboratory, Bar Harbor, Me.) are fed a diet with a fat content of 15-20% and are subcutaneously injected with oligonucleotides of this invention or a control oligonucleotide at a dose of 5, 10 or 25 mg/kg two times per week for 4 weeks. Saline-injected animals and leptin receptor wildtype littermates (i.e. lean littermates) serve as controls. After the treatment period, mice are sacrificed and apolipoprotein(a) levels are evaluated in liver, brown adipose tissue (BAT) and white adipose tissue (WAT). RNA isolation and apolipoprotein(a) mRNA expression level quantitation are performed as described by other examples herein.

After the treatment period, mice are sacrificed and apolipoprotein(a) levels are evaluated in liver, brown adipose tissue (BAT) and white adipose tissue (WAT). RNA isolation and apolipoprotein(a) mRNA expression level quantitation are performed as described by other examples herein.

To assess the physiological effects resulting from antisense inhibition of apolipoprotein(a) mRNA, the db/db mice that receive antisense oligonucleotide treatment are further evaluated at the end of the treatment period for serum lipids, serum apolipoproeins, serum free fatty acids, serum cholesterol (CHOL), liver triglycerides, and fat tissue triglycerides. Serum components are measured on routine clinical diagnostic instruments. Tissue triglycerides are extracted using an acetone extraction technique known in the art, and subsequently measured by ELISA. The presence of the Lp(a) particle in the serum is measured using a commercially available ELISA kit (ALerCHEK Inc., Portland, Me.). Hepatic steatosis, or accumulation of lipids in the liver, is assessed by measuring the liver triglyceride content. Hepatic steatosis is also assessed by routine histological analysis of frozen liver tissue sections stained with oil red O stain, which is commonly used to visualize lipid deposits, and counterstained with hematoxylin and eosin, to visualize nuclei and cytoplasm, respectively.

The effects of apolipoprotein(a) inhibition on glucose and insulin metabolism are also evaluated in the db/db mice treated with antisense oligonucleotides. Plasma glucose is measured at the start of the antisense oligonucleotide treatment and after 2 weeks and 4 weeks of treatment. Plasma insulin is similarly at the beginning to of the treatment, and following 2 weeks and 4 weeks of treatment. Glucose and insulin tolerance tests are also administered in fed and fasted mice. Mice receive intraperitoneal injections of either glucose or insulin, and the blood glucose levels are measured before the insulin or glucose challenge and 15, 30, 60, 90 and 120 minutes following the injection.

To assess the metabolic rates of db/db mice treated with antisense oligonucleotides, the respiratory quotients and oxygen consumptions of the mice are also measured.

The db/db mice that received antisense oligonucleotide treatment are further evaluated at the end of the treatment period for the effects of apolipoprotein(a) inhibition on the expression of genes that participate in lipid metabolism, cholesoterol biosynthesis, fatty acid oxidation, fatty acid storage, gluconeogenesis and glucose metabolism. These genes include, but are not limited to, HMG-CoA reductase, acetyl-CoA carboxylase 1 and acetyl-CoA carboxylase 2, carnitine palmitoyltransferase I and glycogen phosphorylase, glucose-6-phosphatase and phosphoenolpyruvate carboxykinase 1, lipoprotein lipase and hormone sensitive lipase. mRNA levels in liver and white and brown adipose tissue are quantitated by real-time PCR as described in other examples herein, employing primer-probe sets that were generated using published sequences of each gene of interest.

Lean Mice

C57Bl/6 mice are maintained on a standard rodent diet and are used as control (lean) animals. Seven-week old male C57Bl/6 mice are fed a diet with a fat content of 4% and are subcutaneously injected with oligonucleotides of this invention or control oligonucleotide at a dose of 5, 10 or 25 mg/kg two times per week for 4 weeks. Saline-injected animals serve as a control. After the treatment period, mice are sacrificed and apolipoprotein(a) levels are evaluated in liver, brown adipose tissue (BAT) and white adipose tissue (WAT). RNA isolation and apolipoprotein(a) mRNA expression level quantitation are performed as described by other examples herein.

To assess the physiological effects resulting from antisense inhibition of apolipoprotein(a) mRNA, the lean mice that receive antisense oligonucleotide treatment are further evaluated at the end of the treatment period for serum lipids, serum free fatty acids, serum cholesterol (CHOL), liver triglycerides, and fat tissue triglycerides. Serum components are measured on routine clinical diagnostic instruments. Tissue triglycerides are extracted using an acetone extraction technique known in the art, and subsequently measured by ELISA. The presence of the Lp(a) particle in the serum is measured using a commercially available ELISA kit (ALerCHEK Inc., Portland, Me.). Hepatic steatosis, i.e. accumulation of lipids in the liver, is assessed by measuring the liver triglyceride content. Hepatic steatosis is also assessed by routine histological analysis of frozen liver tissue sections stained with oil red O stain, which is commonly used to visualize lipid deposits, and counterstained with hematoxylin and eosin, to visualize nuclei and cytoplasm, respectively.

The effects of apolipoprotein(a) inhibition on glucose and insulin metabolism are also evaluated in the lean mice treated with antisense oligonucleotides of this invention. Plasma glucose is measured at the start of the antisense oligonucleotide treatment and after 2 weeks and 4 weeks of treatment. Plasma insulin is similarly at the beginning to of the treatment, and following 2 weeks and 4 weeks of treatment. Glucose and insulin tolerance tests are also administered in fed and fasted mice. Mice receive intraperitoneal injections of either glucose or insulin, and the blood glucose levels are measured before the insulin or glucose challenge and 15, 30, 60, 90 and 120 minutes following the injection.

To assess the metabolic rates of lean mice treated with antisense oligonucleotides of this invention, the respiratory quotients and oxygen consumptions of the mice can also be measured.

The lean mice that received antisense oligonucleotide treatment are further evaluated at the end of the treatment period for the effects of apolipoprotein(a) inhibition on the expression of genes that participate in lipid metabolism, cholesoterol biosynthesis, fatty acid oxidation, fatty acid storage, gluconeogenesis and glucose metabolism. These genes include, but are not limited to, HMG-CoA reductase, acetyl-CoA carboxylase 1 and acetyl-CoA carboxylase 2, carnitine palmitoyltransferase I and glycogen phosphorylase, glucose-5-phosphatase and phosphoenolpyruvate carboxykinase 1, lipoprotein lipase and hormone sensitive lipase. mRNA levels in liver and white and brown adipose tissue are quantitated by real-time PCR as described in other examples herein, employing primer-probe sets that were generated using published sequences of each gene of interest.

Example 20

Antisense Inhibition of Human Apolipoprotein(a) Using Chimeric Phosphorothioate Oligonucleotides Having 2'-MOE Wings and a Deoxy Gap: Primary Human Hepatocytes In a further embodiment, antisense oligonucleotides targeted to human apolipoprotein(a) were tested for their ability to inhibit target expression in primary human hepatocytes. Pre-plated primary human hepatocytes were purchased from InVitro Technologies (Baltimore, Md.). Cells were cultured in high-glucose DMEM (Invitrogen Life Technologies, Carlsbad, Calif.) supplemented with 10% fetal bovine serum, 100 units per mL penicillin, and 100 µg/mL streptomycin (all supplements from Invitrogen Life Technologies, Carlsbad, Calif.). Immediately upon receipt from the vendor, cells were transfected with a dose of 150 nM of antisense oligonucleotide as described in other examples herein.

In this assay, target mRNA expression was measured by real-time PCR. Additional primers and probe to human apolipoprotein(a) were designed using published sequence (GENBANK® accession # NM_005577.1, incorporated herein as SEQ ID NO: 4). The additional PCR primers were:
forward primer: CCACAGTGGCCCCGGT (SEQ ID NO: 71)
reverse primer: ACAGGGCTTTTCTCAGGTGGT (SEQ ID NO: 72) and the additional PCR probe was: FAM-CCAAG-CACAGAGGCTCCTTCTGAACAAG-TAMRA (SEQ ID NO: 73). Gene target quantities were normalized using GAPDH expression levels. For human GAPDH the PCR primers were:
forward primer: GAAGGTGAAGGTCGGAGTC(SEQ ID NO: 74)
reverse primer: GAAGATGGTGATGGGATTTC (SEQ ID NO: 75) and the PCR probe was: 5' JOE-CAAGCTTCCCGT-TCTCAGCC-TAMRA 3' (SEQ ID NO: 76) where JOE is the fluorescent reporter dye and TAMRA is the quencher dye.

Primary human hepatocyes were treated with 150 nM of the compounds shown in Table 4. Untreated cells served as the control to which all data were normalized. Following 24 hours of treatment, apolipoprotein(a) expression levels were measured by real-time PCR as described herein, using the primers and probe described by SEQ ID NOs 71, 72 and 73. The data, shown in Table 4, represent the average of three experiments and are normalized to untreated control cells.

TABLE 4

Antisense inhibition of human apolipoprotein(a) using chimeric phosphorothioate oligonucleotides having 2'-MOE wings and a deoxy gap: primary human hepatocytes

| ISIS # | REGION | TARGET SEQ ID NO | TARGET SITE | % INHIB | SEQ ID NO |
|---|---|---|---|---|---|
| 144367 | Coding | 4 | 174 | 77 | 11 |
| 144368 | Coding | 4 | 352 | 59 | 12 |
| 144369 | Coding | 4 | 522 | 69 | 13 |
| 144370 | Coding | 4 | 1743 | 75 | 14 |
| 144371 | Coding | 4 | 2768 | 57 | 15 |
| 144372 | Coding | 4 | 2910 | 54 | 16 |
| 144373 | Coding | 4 | 3371 | 49 | 17 |
| 144374 | Coding | 4 | 4972 | 80 | 18 |
| 144375 | Coding | 4 | 5080 | 11 | 19 |
| 144376 | Coding | 4 | 5315 | 82 | 20 |
| 144377 | Coding | 4 | 5825 | 72 | 21 |
| 144378 | Coding | 4 | 6447 | 72 | 22 |
| 144379 | Coding | 4 | 7155 | 46 | 23 |
| 144380 | Coding | 4 | 7185 | 78 | 24 |
| 144381 | Coding | 4 | 8463 | 64 | 25 |
| 144382 | Coding | 4 | 8915 | 58 | 26 |
| 144383 | Coding | 4 | 9066 | 79 | 27 |
| 144384 | Coding | 4 | 10787 | 0 | 28 |
| 144385 | Coding | 4 | 11238 | 94 | 29 |
| 144386 | Coding | 4 | 11261 | 61 | 30 |
| 144387 | Coding | 4 | 11461 | 60 | 31 |
| 144388 | Coding | 4 | 11823 | 57 | 32 |
| 144389 | Coding | 4 | 11894 | 39 | 33 |
| 144390 | Coding | 4 | 11957 | 0 | 34 |
| 144391 | Coding | 4 | 12255 | 57 | 35 |
| 144392 | Coding | 4 | 12461 | 50 | 36 |
| 144393 | Coding | 4 | 12699 | 82 | 37 |
| 144394 | Coding | 4 | 13354 | 76 | 38 |
| 144395 | 3'UTR | 4 | 13711 | 84 | 39 |

TABLE 4-continued

Antisense inhibition of human apolipoprotein(a) using chimeric phosphorothioate oligonucleotides having 2'-MOE wings and a deoxy gap: primary human hepatocytes

| ISIS # | REGION | TARGET SEQ ID NO | TARGET SITE | % INHIB | SEQ ID NO |
|---|---|---|---|---|---|
| 144396 | 3'UTR | 4 | 13731 | 72 | 40 |
| 144397 | 3'UTR | 4 | 13780 | 64 | 41 |
| 144398 | 3'UTR | 4 | 13801 | 33 | 42 |
| 144399 | 3'UTR | 4 | 13841 | 44 | 43 |
| 144400 | 3'UTR | 4 | 13861 | 75 | 44 |
| 144401 | 3'UTR | 4 | 13881 | 72 | 45 |

Example 21

Effects of Antisense Oligonucleotides Targeted to Human Apolipoprotein(a) on Human Plasminogen Expression Human apolipoprotein(a) sequence shares a high degree of homology with the human plasminogen sequence. Thus it was of interest to determine if antisense oligonucleotides targeting apolipoprotein(a) would exhibit an inhibitory effect on human plasminogen.

In a further embodiment, compounds designed to target human apolipoprotein(a), shown in Table 1, were tested for their effects on human plasminogen mRNA expression. Preplated primary human hepatocytes were purchased from InVitro Technologies (Baltimore, Md.). Cells were cultured in high-glucose DMEM (Invitrogen Life Technologies, Carlsbad, Calif.) supplemented with 10% fetal bovine serum, 100 units per mL penicillin, and 100 µg/mL streptomycin (all supplements from Invitrogen Life Technologies, Carlsbad, Calif.). Immediately upon receipt from the vendor, cells were transfected with a dose of 150 nM of antisense oligonucleotide as described in other examples herein.

Following 24 hours of exposure to antisense oligonucleotides, human plasminogen mRNA levels were measured by quantitative real-time PCR as described in other examples herein. Probes and primers to human plasminogen were designed to hybridize to a human plasminogen sequence, using published sequence information (GENBANK® accession number NM_000301.1, incorporated herein as SEQ ID NO: 77).

For human plasminogen, the PCR primers were:

forward primer: CGCTGGGAACTTTGTGACATC (SEQ ID NO: 78)

reverse primer: CCCGCTGCACAACACCTCCACC (SEQ ID NO: 79) and the PCR probe was: 5' JOE-CACTGGTAG-GTGGGACCAGAA-TAMRA 3' (SEQ ID NO: 80) where JOE is the fluorescent reporter dye and TAMRA is the quencher dye. Gene target quantities were normalized using GAPDH expression levels.

Data, shown in Table 5, are averages from three experiments in which primary human hepatocytes were treated with antisense oligonucleotides targeted to human apolipoprotein (a).

TABLE 5

Effects of chimeric phosphorothioate oligonucleotides targeted to human apolipoprotein(a) on human plamsinogen expression

| ISIS # | % INHIB | SEQ ID NO |
|---|---|---|
| 144367 | 62 | 11 |
| 144368 | 49 | 12 |
| 144369 | 8 | 13 |
| 144370 | 44 | 14 |
| 144371 | 0 | 15 |
| 144372 | 11 | 16 |
| 144373 | 33 | 17 |
| 144374 | 60 | 18 |
| 144375 | 9 | 19 |
| 144376 | 32 | 20 |
| 144377 | 43 | 21 |
| 144378 | 8 | 22 |
| 144379 | 0 | 23 |
| 144380 | 31 | 24 |
| 144381 | 13 | 25 |
| 144382 | 45 | 26 |
| 144383 | 47 | 27 |
| 144384 | 0 | 28 |
| 144385 | 0 | 29 |
| 144386 | 0 | 30 |
| 144387 | 0 | 31 |
| 144388 | 36 | 32 |
| 144389 | 0 | 33 |
| 144390 | 0 | 34 |
| 144391 | 0 | 35 |
| 144392 | 0 | 36 |
| 144393 | 58 | 37 |
| 144394 | 24 | 38 |
| 144395 | 35 | 39 |
| 144396 | 62 | 40 |
| 144397 | 25 | 41 |
| 144398 | 0 | 42 |
| 144399 | 0 | 43 |
| 144400 | 60 | 44 |
| 144401 | 0 | 45 |

These data illustrate that ISIS 144371, 144379, 144384, 144385, 144386, 144387, 144389, 144390, 144391, 144392, 144398, 144399 and 144401 do not inhibit plasminogen expression. Thus, in this assay, these compounds selectively inhibit apolipoprotein(a) expression. ISIS 144369, 144378 and 144375 demonstrated less than 10% inhibition of plasminogen. The target sites in human apolipoprotein(a) to which ISIS 144379, ISIS 144368 and ISIS 144376 bind share 70%, 70% and 80% nucleotide identity with human plasminogen, respectively.

Example 22

Antisense Inhibition of Human Apolipoprotein(a) In Vivo: Transgenic Mouse Study

Apolipoprotein(a) is found in humans, nonhuman primates and the European hedgehog, but not in common laboratory animals such as rats and mice. Accordingly, mice harboring a human apolipoprotein(a) transgene are required to investigate the effects of antisense oligonucleotides on human apolipoprotein(a) expression.

In a further embodiment, antisense oligonucleotides targeted to human apolipoprotein(a) were tested for their effects in mice transgenic for both human apolipoprotein(a) and human apolipoprotein B, as well as in mice transgenic for human apolipoprotein B alone. The transgenic mice were provided by Dr. Robert Pitas and Dr. Matthias Schneider in the Gladstone Institute at the University of California, San Francisco.

Mice were treated with 25 mg/kg of ISIS 144379 (SEQ ID NO: 23), twice weekly, for a period of 4 weeks. A control group consisting of mice transgenic for both human genes was treated with saline. Each treatment group consisted of 4 animals. At the end of the 4 week treatment period, animals were sacrificed, and apolipoprotein(a) mRNA levels in liver tissue were measured by real-time PCR, as described herein. Apolipoprotein B mRNA was also measured by real-time PCR with probes and primers designed using published sequence information (GENBANK® accession number NM_000384.1, incorporated herein as SEQ ID NO: 81). For human apolipoprotein B the PCR primers were:

forward primer: TGCTAAAGGCACATATGGCCT (SEQ ID NO: 82)

reverse primer: CTCAGGTTGGACTCTCCATTGAG (SEQ ID NO: 83) and the PCR probe was: FAM-CTTGTCA-GAGGGATCCTAACACTGGCCG-TAMRA (SEQ ID NO: 84) where FAM is the fluorescent reporter dye and TAMRA is the quencher dye. Gene target quantities were normalized using mouse GAPDH expression levels, as described herein.

The data, shown in Table 6, represent the average of all animals in each treatment group and are normalized to saline-treated control animals.

TABLE 6

Antisense inhibition of human apolipoprotein(a) in transgenic mice

| Transgene | mRNA expression % control | |
|---|---|---|
| | apoB | apo(a) |
| apolipoprotein B | 101 | 0 |
| apolipoprotein B apolipoprotein(a) | 133 | 61 |

These data illustrate that treatment of mice transgenic for human apolipoprotein(a) and human apolipoprotein B with ISIS 144379 resulted in a decrease in apolipoprotein(a), but not apolipoprotein B, mRNA expression.

Example 23

Antisense Oligonucleotides Targeted to Apolipoprotein(a) Having 2'-MOE Wings and Deoxy Gaps In a further embodiment, and additional series of oligonucleotides was designed to target the human apolipoprotein (a) sequence, using public sequence information (GENBANK® accession # NM_005577.1, incorporated herein as SEQ ID NO: 4). The compounds are shown in Table 7. "Target site" indicates the first (5'-most) nucleotide number on the particular target sequence to which the compound binds. All compounds in Table 7 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines.

TABLE 7

Antisense oligonucleotides targeted to
apolipoprotein(a) having 2'-MOE wings and a
deoxy gap

| ISIS # | REGION | TARGET SEQ ID NO | TARGET SITE | SEQUENCE | SEQ ID NO |
|---|---|---|---|---|---|
| 359474 | 5' UTR | 4 | 11 | cagtgtccagaaagtgtgtc | 85 |
| 359475 | Coding | 4 | 12380 | ggtttgctcagttggtgctg | 86 |
| 359476 | Coding | 4 | 12409 | ttaccatggtagcactgccg | 87 |
| 359477 | Coding | 4 | 12419 | actctggccattaccatggt | 88 |
| 359478 | Coding | 4 | 12449 | tgtgacagtggtggagaatg | 89 |
| 359479 | Coding | 4 | 12669 | tgacagtcggaggagcgacc | 90 |
| 359480 | Coding | 4 | 12839 | tgcccatttatttgtccctg | 91 |
| 359481 | Coding | 4 | 12919 | agttttcttggattcattgt | 92 |
| 359482 | Coding | 4 | 12944 | gagagggatatcacagtagt | 93 |
| 359483 | Coding | 4 | 13359 | cagtcctggcggtgaccatg | 94 |
| 359484 | Coding | 4 | 13466 | cttatagtgattgcacactt | 95 |
| 359485 | Coding | 4 | 13493 | tctggccaaatgctcagcac | 96 |

Example 24

Antisense Inhibition of Apolipoprotein(a) in Human Primary Hepatocytes: Dose Response In a further embodiment, antisense oligonucleotides targeted to human apolipoprotein(a) were selected for dose response studies. Human primary hepatocytes were treated with 25, 50, 150 and 300 nM of ISIS 144367, ISIS 144370, ISIS 144385, ISIS 144393 and ISIS 144395. ISIS 133529 was used as a control oligonucleotide. Untreated cells served as the control to which data were normalized. Following 24 hours of exposure to antisense oligonucleotides, target mRNA expression levels were measured by real-time PCR as described by other examples herein. The results, shown in Table 8, are the average of 3 experiments and are expressed as percent inhibition of apolipoprotein(a) expression relative to untreated control cells. "N.D." indicates not determined.

TABLE 8

Antisense inhibition of apolipoprotein(a) in human
primary hepatocytes: dose response

| | % Inhibition relative to untreated control cells Dose of oligonucleotide | | | |
|---|---|---|---|---|
| ISIS # | 25 | 50 | 150 | 300 |
| 144367 | 57 | 76 | 88 | 87 |
| 144370 | 47 | 62 | 56 | 26 |
| 144385 | 33 | 36 | 59 | 39 |
| 144393 | 23 | 32 | 35 | 30 |
| 144395 | 34 | 35 | 35 | 35 |
| 113529 | N.D. | N.D. | 8 | 21 |

These data demonstrate that ISIS 144367 inhibited apolipoprotein(a) in a dose-dependent manner. The other oligonucleotides tested were able to reduce apolipoprotein(a) expression.

Example 25

Effects of Antisense Inhibition of Apolipoprotein(a) on Plasminogen Expression: Dose Response in Primary Human Hepatocytes In a further embodiment, antisense oligonucleotides targeted to human apolipoprotein(a) were tested for their ability to inhibit human plasminogen expression. Human primary hepatocytes were treated with 25, 50, 150 and 300 nM of ISIS 144367, ISIS 144370, ISIS 144385, ISIS 144393 and ISIS 144395. ISIS 113529 was used as a control oligonucleotide. Untreated cells served as the control to which data were normalized. Following 24 hours of exposure to antisense oligonucleotides, target mRNA expression levels were measured by real-time PCR as described by other examples herein. The results, shown in Table 9, are the average of 3 experiments and are expressed as percent inhibition of apolipoprotein(a) expression relative to untreated control cells. "N.D." indicates not determined.

TABLE 9

Effects of antisense inhibition of apolipoprotein(a) on
plasminogen expression in human primary hepatocytes: dose
response

| | % plasminogen expression relative to untreated control cells Dose of oligonucleotide (nM) | | | |
|---|---|---|---|---|
| ISIS # | 25 | 50 | 150 | 300 |
| 144367 | 0 | 0 | 0 | 0 |
| 144370 | 0 | 6 | 9 | 0 |
| 144385 | 10 | 5 | 12 | 0 |
| 144393 | 10 | 39 | 2 | 0 |
| 144395 | 0 | 0 | 0 | 0 |
| 113529 | N.D. | N.D. | 76 | 89 |

These data demonstrate that ISIS 144367 and ISIS 144395 did not inhibit the expression of plasminogen in this assay and are therefore apolipoprotein(a)-specific antisense oligonucleotides. ISIS 144370 and ISIS 144385 did not result in a considerable reduction in plasminogen expression.

Example 26

Effects of Antisense Inhibition of Apolipoprotein(a) in Cytokine-Induced Cells

Elevated plasma levels of Lp(a), caused by increased expression of apolipoprotein(a), is an independent risk factor for a variety of cardiovascular disorders, including atherosclerosis, hypercholesterolemia, myocardial infarction and thrombosis (Seed et al., *N. Engl. J. Med.*, 1990, 322, 1494-1499; Sandkamp et al., *Clin. Chem.*, 1990, 36, 20-23; Nowak-Gottl et al., *Pediatrics*, 1997, 99, E11). Furthermore, increases in plasma Lp(a) are associated with elevations in several acute-phase proteins, which participate in the acute-phase of the immune response and function to promote inflammation, activate the complement cascade, and stimulate chemotaxis of phagocytes. Thus, Lp(a) is proposed to be an acute-phase reactant and, consequently, responsive to cytokines. The apolipoprotein(a) promoter contains several functional cis-acting elements that are responsive to interleukin-6 (Wade et al., *Proc. natl. Acad. Sci. USA*, 1993, 90, 1369-1373), a major mediator of the acute phase response, further suggesting a link between Lp(a) and the acute phase response. An association between cytokines and Lp(a) was observed in primary monkey hepatocytes, where stimulation of the cells with interleukin-6 resulted in an increase in Lp(a) protein, as well as in apolipoprotein(a) mRNA (Ramharack et al., *Arterioscler. Thromb. Vasc. Biol.,* 1998, 18, 984-990). To date, no direct association between cytokines and apolipoprotein(a) expression has been demonstrated in humans. Thus, it is of interest to determine whether the antisense inhibition of apolipoprotein(a) is affected by cytokine induction.

In a further embodiment, the ability of ISIS 144367 (SEQ ID NO: 11) to inhibit apolipoprotein(a) expression was investigated in primary human hepatocytes which were induced with cytokines. For a period of 24 hours, cells were induced using culture media supplemented with a final concentration of 1 μM dexamethasone, 400 U/ml interleukin-1B and 200 U/ml interleukin-6. At the end of this induction period, cells were treated with oligonucleotide as described herein, for a period of 48 hours. One group of cells was cytokine-induced and treated with 12.5, 25, 50, 100 or 200 nM of ISIS 144367; data from these cells was normalized to data from cells receiving only cytokine treatment. A second group of cells received no cytokine induction and were treated with 12.5, 25, 50, 100 and 200 nM of ISIS 144367; data from these cells was normalized to cells that received neither cytokine nor oligonucleotide treatment. After the 48 oligonucleotide treatment period, cells were harvested and apolipoprotein(a) expression was measured by real-time PCR as described herein. The data, presented in Table 10, are the average of 3 experiments and are normalized to the respective controls as described. Results are shown as percent inhibition of apolipoprotein(a) expression.

TABLE 10

Antisense inhibition of apolipoprotein(a) in cytokine-induced primary human hepatocytes

| Dose of oligonucleotide (nM) | % Inhibition relative to control | |
|---|---|---|
| | No induction | Cytokine induction |
| 12.5 | 37 | 42 |
| 25 | 37 | 37 |

TABLE 10-continued

Antisense inhibition of apolipoprotein(a) in cytokine-induced primary human hepatocytes

| Dose of oligonucleotide (nM) | % Inhibition relative to control | |
|---|---|---|
| | No induction | Cytokine induction |
| 50 | 42 | 62 |
| 100 | 75 | 87 |
| 200 | 65 | 89 |

These data demonstrate a dose-dependent reduction in apolipoprotein(a) expression cytokine-induced cells following treatment with ISIS 144367. In cells receiving no oligonucleotide treatment, the expression of apolipoprotein(a) was similar in cytokine-induced cells relative to cells that were not exposed to cytokines. Furthermore, ISIS 144367 inhibited apolipoprotein(a) expression to a greater extent in cytokine-induced cells relative to cells not exposed to cytokines. Thus, ISIS 144367 is a more effective inhibitor of apolipoprotein(a) expression in cytokine-induced cells. These data demonstrate a link between cytokine stimulation of primary human hepatocytes and the antisense inhibition of apolipoprotein(a) expression.

The expression of plasminogen was also tested in cytokine-induced cells that received ISIS 144367 treatment. Cells were induced and treated as described for the apolipoprotein(a) mRNA expression experiment. Plasminogen mRNA was measured by real-time PCR as described herein. The data, averaged from 3 experiments and normalized to the appropriate controls, demonstrated that in this assay, in unstimulated cells as well as cytokine-induced cells, ISIS 144367 did not inhibit plasminogen. Thus, the effects of ISIS 144367 are specific to apolipoprotein(a) expression both in the presence and absence of cytokines.

What is claimed is:

1. A method of inhibiting the expression of apolipoprotein (a) in a cell or tissue comprising contacting said cell or tissue with a compound 15 to 30 nucleobases in length targeted to a nucleic acid molecule encoding apolipoprotein(a) (SEQ ID NO:4), wherein said compound comprises at least 8 consecutive nucleobases of SEQ ID NO:86 and is at least 70% complementary to said nucleic acid molecule encoding apolipoprotein(a), so that expression of apolipoprotein(a) is inhibited.

2. The method of claim 1, wherein the compound is at least 80%, at least 90%, at least 95% or at least 99% complementary with said nucleic acid molecule encoding apolipoprotein (a).

3. The method of claim 1, wherein the compound has at least one modified internucleoside linkage, sugar moiety, or nucleobase.

4. The method of claim 1, wherein the compound has at least one 2'-O-methoxyethyl sugar moiety, phosphorothioate internucleoside linkage or 5-methylcytosine.

* * * * *